(12) United States Patent
Gooding et al.

(10) Patent No.: US 11,766,294 B1
(45) Date of Patent: Sep. 26, 2023

(54) HOMELAND EXPLOSIVE CONSEQUENCE AND THREAT (HEXCAT) MODELING TOOL

(71) Applicant: The Government of the United States of America, as represented by the Secretary of Homeland Security, Washington, DC (US)

(72) Inventors: Rachel Gooding, Herndon, VA (US); Alexander Dolan, Frederick, MD (US); David Bradley, Bel Air, MD (US); Kevin Wegman, Columbus, OH (US); Patrick Wilson, Dublin, OH (US); Brian Hawkins, Broomfield, CO (US); Timothy Davis, Atlanta, GA (US); Thomas Kirsch, Bethesda, MD (US)

( * ) Notice: Subject to any disclaimer, the term of this patent is extended or adjusted under 35 U.S.C. 154(b) by 0 days.

(21) Appl. No.: 17/576,471

(22) Filed: Jan. 14, 2022

Related U.S. Application Data

(60) Provisional application No. 63/137,344, filed on Jan. 14, 2021.

(51) Int. Cl.
*G06G 7/48* (2006.01)
*A61B 34/10* (2016.01)

(52) U.S. Cl.
CPC ........ *A61B 34/10* (2016.02); *A61B 2034/105* (2016.02)

(58) Field of Classification Search
None
See application file for complete search history.

(56) References Cited

PUBLICATIONS

Zhang, Qingtao, et al. "Risk evaluation and analysis of a gas tank explosion based on a vapor cloud explosion model: A case study." Engineering failure analysis 101 (2019): 22-35.*
Niazi, Usama M., Mohammad S. Nasif, and Masdi Muhammad. "Effect of wind directions on human injury and fatality risk modeling due to vapor cloud explosion in offshore platforms." Process safety progress 39 (2020): e12123.*
Youtube video. Gexcon UK "Dust Explosion Modeling." Feb. 12, 2016. Retrieved from the internet: <http://youtu.be/h9IWRp2N7u8>.*
Valsamos, Georgios, Martin Larcher, and Folco Casadei. "Beirut explosion 2020: A case study for a large-scale urban blast simulation." Safety science 137 (2021): 105190.*
Liu, Zihan, et al. "Damage effect of terrorist attack explosion-induced shock wave in a double-deck island platform metro station." Periodica Polytechnica Civil Engineering 65.1 (2021): 215-228.*
Kim, Eui Soo, et al. "The Study on Evaluation of Human Body Injury by Explosion of Portable Butane Gas Range." Journal of the Korean Society of Safety 31.3 (2016): 60-67.*
Sevim, Barış, and Ahmet Tuğrul Toy. "Blasting response of a two-storey RC building under different charge weight of TNT explosives." Iranian Journal of Science and Technology, Transactions of Civil Engineering 44.2 (2020): 565-577.*
Yin, Yueping, et al. "Mechanism on apparent dip sliding of oblique inclined bedding rockslide at Jiweishan, Chongqing, China." Landslides 8.1 (2011): 49-65.*
Abbasi, Behrooz, D. Russell, and R. Taghavi. "FLAC3D mesh and zone quality." FLAC/DEM Symposium. China: Itasca Consulting Group. 2013.*

* cited by examiner

*Primary Examiner* — Anna Skibinsky
(74) *Attorney, Agent, or Firm* — Lavanya Ratnam; Robert W. Busby; Kelly G. Hyndham

(57) ABSTRACT

A system to estimate consequences of an explosion includes a scenario generator to generate a scenario based on user input and scenario parameters; an explosive device model generator to generate an explosive device model based on the user input and explosive device parameters; a propagation of hazards modeler to model propagation of hazards into the scenario based on the user input and hazard parameters; an injury modeler to model injuries corresponding to modeling propagation of hazards into the scenario based on injury parameters; and an iteration and output generator to iterate by using additional iterative subsets of the parameters to generate the scenario, generate the explosive device model, model propagation of hazards, and model injuries, until parameter spaces of the parameters are covered. The iteration and output generator generates an injury record based injury outcomes from the modeling of injuries corresponding to the iterating.

25 Claims, 38 Drawing Sheets

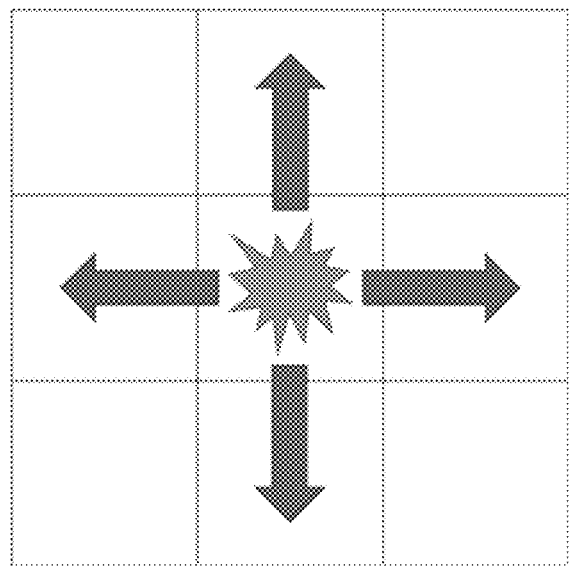
*FIG. 33*
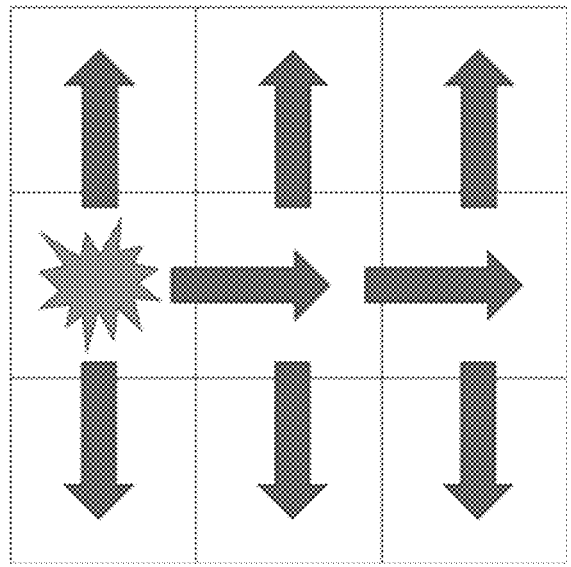 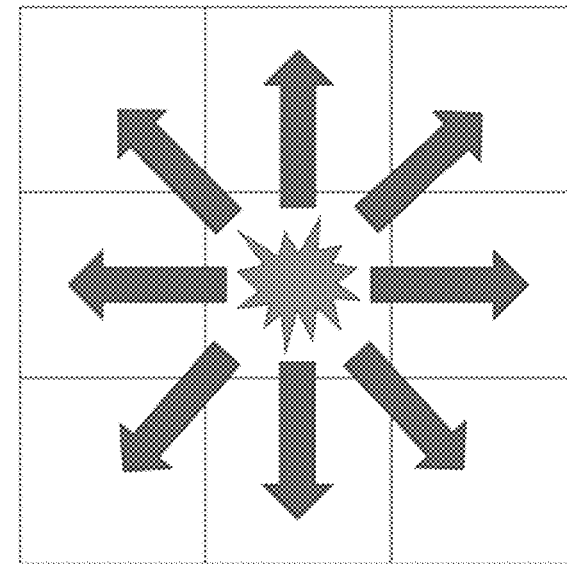
*FIG. 34*      *FIG. 35*

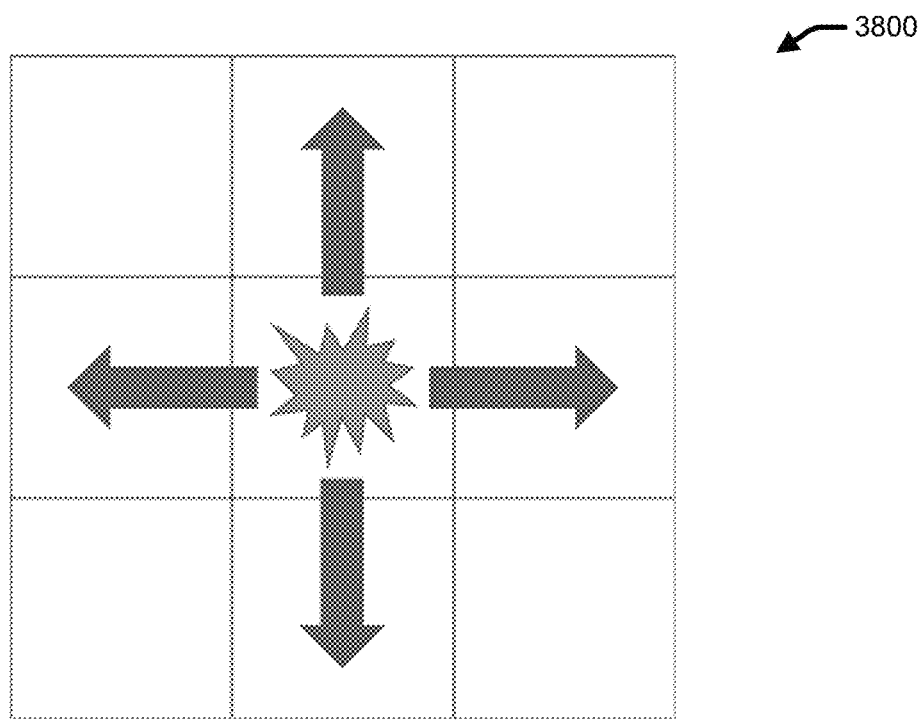
FIG. 38
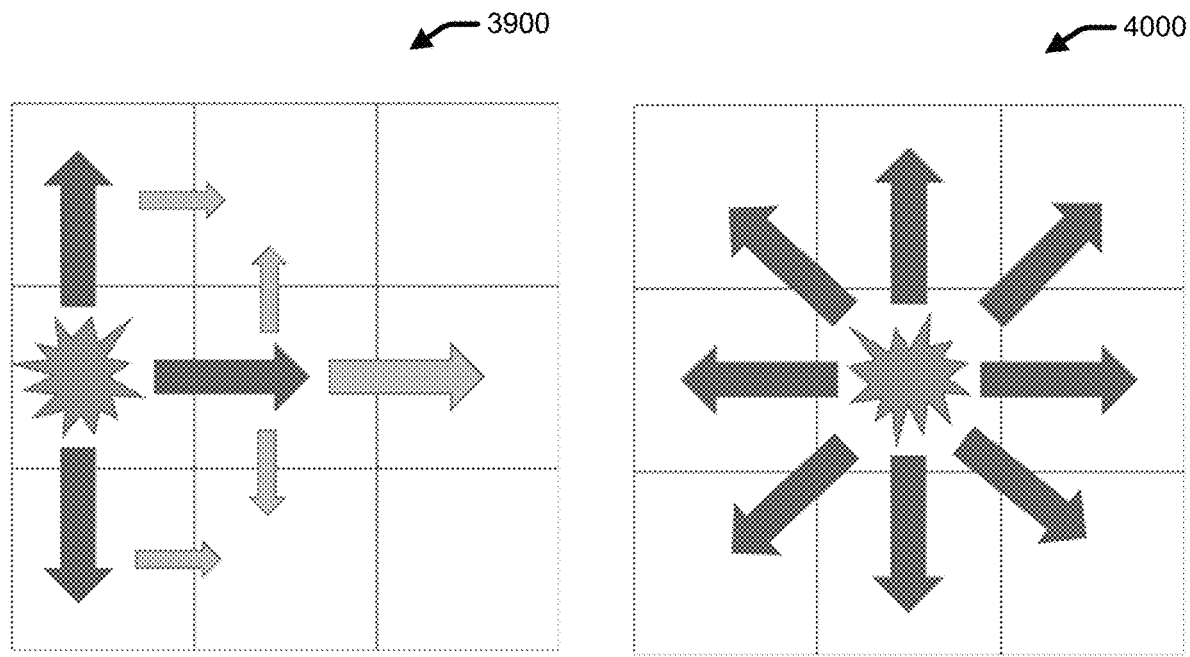
FIG. 39
FIG. 40

Fig. 10: P-I graph for a skull-base fracture.

HOMELAND EXPLOSIVE CONSEQUENCE AND THREAT (HEXCAT) MODELING TOOL

CROSS-REFERENCE TO RELATED APPLICATIONS

This application is a nonprovisional application that claims the benefit of priority from U.S. provisional application 63/137,344 filed on Jan. 14, 2021, entitled "Homeland Explosive Consequence and Threat (HExCAT) Modeling Tool," the disclosure of which is incorporated by reference in its entirety.

STATEMENT OF GOVERNMENT INTEREST

The present invention was made by employees of the United States Department of Homeland Security in the performance of their official duties. The Government has certain rights in the invention.

FIELD

The discussion below relates generally to estimating consequences of explosive attack scenarios and the impacts of mitigating strategies to address the effects of explosive attack scenarios.

BACKGROUND

This section provides a brief introduction to the technical subject matter without distinguishing what aspects of the technology are or are not in the prior art. Nothing in this section amounts to an admission regarding the prior art.

Modeling packages are available to model buildings. However, such modeling packages rely on the collection of enormous datasets to specify buildings to be modeled. Other modeling packages are available to model other objects, but lack coordination with each other to achieve more complex outcomes.

SUMMARY

In an embodiment, a method estimates consequences of an explosion. The method receives user input including parameters for generating and modeling. The method generates a scenario based on the user input indicating indoor or outdoor, and based on an iterative subset of a distribution of scenario parameters. The method generates an explosive device model based on the user input and an iterative subset of a distribution of explosive device parameters. The method models propagation of hazards into the scenario based on the user input and an iterative subset of a distribution of hazard parameters. The hazards correspond to detonation of the explosive device model. The method models injuries, corresponding to modeling propagation of hazards into the scenario, based on an iterative subset of a distribution of injury parameters. The method iterates by using additional iterative subsets of the distribution of scenario parameters, distribution of explosive device parameters, distribution of hazard parameters, and distribution of injury parameters to generate the scenario, generate the explosive device model, model propagation of hazards, and model injuries, until parameter spaces of the distribution of scenario parameters, distribution of explosive device parameters, distribution of hazard parameters, and distribution of injury parameters are covered. The method generates an injury record based on a plurality of injury outcomes from the modeling of injuries corresponding to the iterating.

In another embodiment, a system to estimate consequences of an explosion, comprises a computer system. The computer system includes a processing system having a hardware processor to perform a predefined set of basic operations by loading a predefined native instruction set of codes constituting a set of instructions selectable for execution by the hardware processor. The computer system also includes a memory accessible to the processing system, and a user interface controller under control of the processing system. The system includes user interface logic, stored in the memory, including a sequence of instructions selected from the predefined native instruction set of codes of the hardware processor, adapted to operate with the processing system and the user interface controller to implement a user interface adapted to prompt for user input and receive the user input. The system also includes a communication system, under control of the processing system, adapted to transmit requests for datasets used by logic for generating scenarios, generating explosive device models, modeling propagation of hazards, modeling injuries, and modeling medical mitigation responses, and adapted to receive the datasets. The system further includes explosive device model logic, stored in the memory, comprising a respective sequence of instructions selected from the predefined native instruction set of codes of the hardware processor, adapted to generate an explosive device model based on the user input and an iterative subset of a distribution of explosive device parameters. The system includes propagation of hazards logic, stored in the memory, comprising a respective sequence of instructions selected from the predefined native instruction set of codes of the hardware processor, adapted to model propagation of hazards into the scenario based on the user input and an iterative subset of a distribution of hazard parameters, the hazards corresponding to detonation of the explosive device model. The system also includes injury modeler logic, stored in the memory, comprising a respective sequence of instructions selected from the predefined native instruction set of codes of the hardware processor, adapted to model injuries corresponding to the modeling propagation of hazards into the scenario based on an iterative subset of a distribution of injury parameters. The system further includes iteration logic, stored in the memory, comprising a respective sequence of instructions selected from the predefined native instruction set of codes of the hardware processor, adapted to iterate by using additional iterative subsets of the distribution of scenario parameters, distribution of explosive device parameters, distribution of hazard parameters, and distribution of injury parameters to generate the scenario, generate the explosive device model, model propagation of hazards, and model injuries, until parameter spaces of the distribution of scenario parameters, distribution of explosive device parameters, distribution of hazard parameters, and distribution of injury parameters are covered. The system yet further includes output logic, stored in the memory, comprising a respective sequence of instructions selected from the predefined native instruction set of codes of the hardware processor, adapted to generate an injury record based on a plurality of injury outcomes from the modeling of injuries corresponding to the iterating. The processing system is further configured to output the injury record when iteration is completed.

In yet another embodiment, a tangible non-transitory computer-readable medium having stored thereon computer-executable instructions that, if executed by a computing device, cause the computing device to receive user input including parameters for generating and modeling. The computer-executable instructions, if executed by a computing device, also cause the computing device to generate a scenario based on the user input indicating indoor or outdoor, and based on an iterative subset of a distribution of scenario parameters. The computer-executable instructions, if executed by a computing device, also cause the computing device to generate an explosive device model based on the user input and an iterative subset of a distribution of explosive device parameters. The computer-executable instructions, if executed by a computing device, cause the computing device to model propagation of hazards into the scenario based on the user input and an iterative subset of a distribution of hazard parameters, the hazards corresponding to detonation of the explosive device model. The computer-executable instructions, if executed by a computing device, cause the computing device to model injuries corresponding to modeling propagation of hazards into the scenario based on an iterative subset of a distribution of injury parameters. The computer-executable instructions, if executed by a computing device, also cause the computing device to iterate by using additional iterative subsets of the distribution of scenario parameters, distribution of explosive device parameters, distribution of hazard parameters, and distribution of injury parameters to generate the scenario, generate the explosive device model, model propagation of hazards, and model injuries, until parameter spaces of the distribution of scenario parameters, distribution of explosive device parameters, distribution of hazard parameters, and distribution of injury parameters are covered. The computer-executable instructions, if executed by a computing device, cause the computing device to generate an injury record based on a plurality of injury outcomes from the modeling of injuries corresponding to the iterating.

Other features and aspects of various embodiments will become apparent to those of ordinary skill in the art from the following detailed description which discloses, in conjunction with the accompanying drawings, examples that explain features in accordance with embodiments. This summary is not intended to identify key or essential features, nor is it intended to limit the scope of the invention, which is defined solely by the claims.

BRIEF DESCRIPTION OF THE DRAWINGS

FIG. 33 illustrates Initial Blast Expansion according to an embodiment.

FIG. 34 illustrates Shockwave Propagation Population according to an embodiment.

FIG. 35 illustrates Spherical Shockwave according to an embodiment.

FIG. 38 illustrates Initial Debris Expansion according to an embodiment.

FIG. 39 illustrates Fragment Propagation according to an embodiment.

FIG. 40 illustrates Spherical Propagation according to an embodiment.

DETAILED DESCRIPTION

The HExCAT application is a software tool which provides users with the capability to simulate a wide range of potential explosive events and the corresponding medical response associated with those events. The application includes capability to simulate attacks where explosives are placed interior to a building (e.g., an office building) or in an outdoor space (i.e., car bomb in a city center). The HExCAT explosive models ingest a large amount of data defining the explosive device and the target to generate realistic simulations which propagate the explosive hazards to determine human health effects to the target population as a result of the attack. Default values are provided for most user inputs, dramatically reducing the amount of input required by a user to execute a scenario. The user has the option to modify these default values in cases where higher specificity is required to define the scenario desired.

Figure 1:
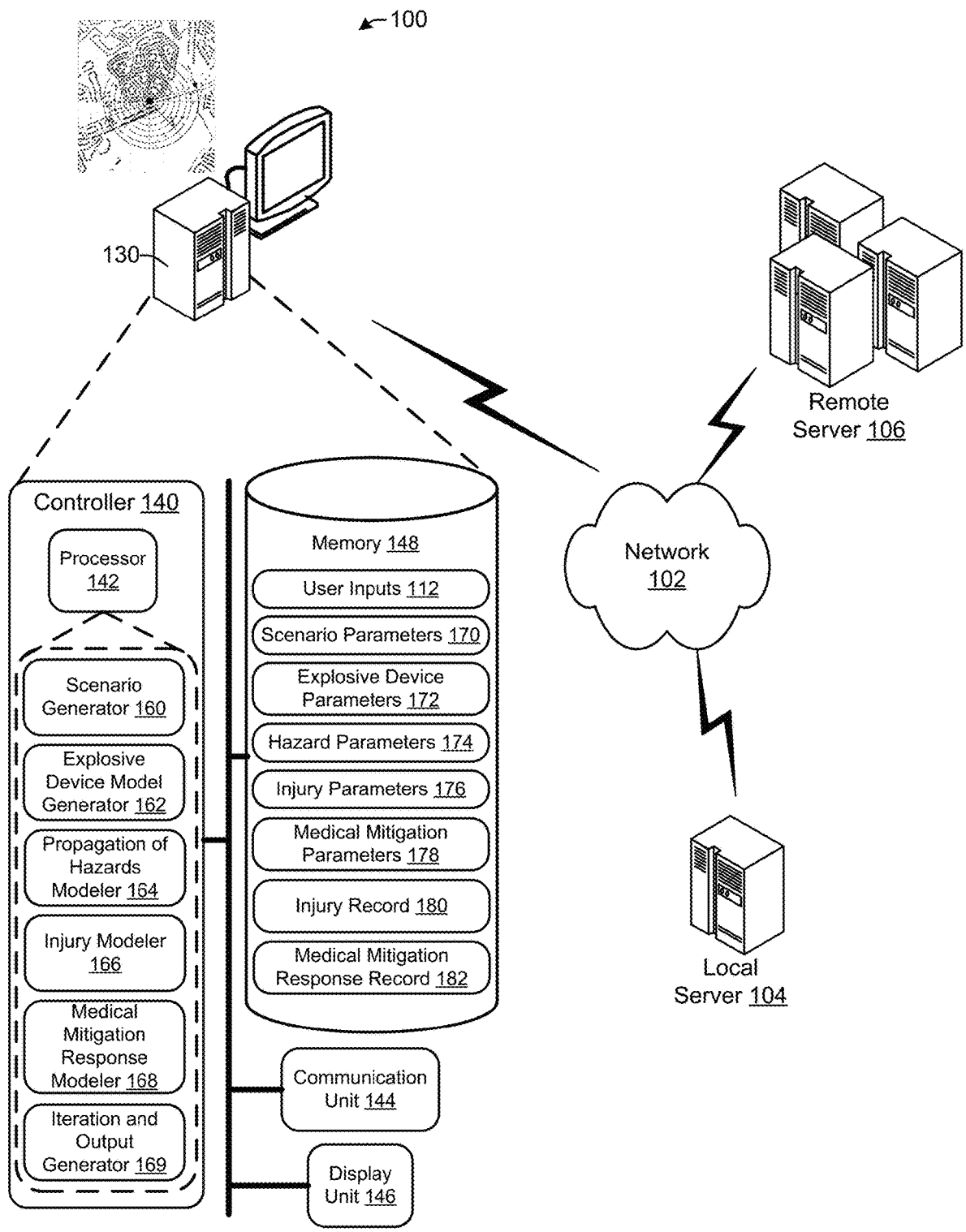
FIG. 1 illustrates a system to estimate consequences of an explosion according to an embodiment.

FIG. 1 illustrates a system 100 to estimate consequences of an explosion according to an embodiment. The system 100 includes a computing system 130, in communication via network 102 with local server 104 and remote server 106. The computing system 130 includes controller 140 coupled via a bus to memory 148, communication unit 144, and display unit 146. The controller 140 includes a processor 142 to execute scenario generator 160, explosive device model generator 162, propagation of hazards modeler 164, injury modeler 166, medical mitigation response modeler 168, and iteration and output generator 169.

The memory 148 is associated with user inputs 112, scenario parameters 170, explosive device parameters 172, hazard parameters 174, injury parameters 176, medical mitigation parameters 178, injury record 180, and medical mitigation response record 182.

The computer system 130 includes one or more communicatively coupled communication units 144, processors 142, and memory 148. The communication unit 144 is representative of one or more devices able to communicate information to or from other devices and components including in instances those included in or external to the system 100. Example communication units 144 include but are not limited to wireless modems (such as an 802.11 compliant unit), wired (e.g., Ethernet-ready) or other such communication interfaces, or a cellular communication transceiver. Example 802.11 compliant modems or cards include but are not limited to those compliant with 802.11n, 802.11ac, 802.11ad, 802.11ah, 802.11aj, 802.11ax, and the like wireless local area network standards promulgated by the Institute of Electrical and Electronics Engineers (IEEE), New York, N.Y.

Although a single processor 142 and memory 148 are shown, the computer system 130 can be constructed with multiple processors and memory. The processor 142 is representative of hardware that is capable of processing computer executable instructions, such as a central processing unit that executes a program of instructions. In embodiments, the processing unit (processor 142) implements an operating system which is a set of instructions that allows the processor to perform specialized instructions according to a program run on the operating system or processor platform.

Local memory 148 is representative of a wide variety and types and combinations of memory suitable for storing information in an electronic format. Example memory includes but is not limited to random access memory (RAM), hard disk memory, removable medium memory, flash storage memory, and other types of computer-readable media including non-transitory data storage.

In embodiments, the controller 140 is representative of hardware or software that is constructed to function as described in this disclosure. For example, the controller 140 is a combination of software (such as a program of instructions that is stored in local memory) that is useable by the processor 142 to provide the described capabilities and functions, such as when the embodied instructions are executed by the processor 142 included in the computer system 130. As illustrated and for ease of understanding, the controller 140 includes the processor 142 and the various illustrated generators and modelers, and other logic or features described herein. While shown and described as individual modules, the supporting hardware or software can be configured as an integrated program of instructions to provide the described functionality, such as through the use of application program interfaces (APIs) that permit individual programs to interface to one or more other programs and provide one or more graphical user interfaces (GUIs)

output on a display unit 146 to a user to access information or exercise control over the computing system 130 including a visual display output.

The computing system 130 executes the various modules associated with processor 142. The scenario generator 160 generates a scenario based on user inputs 112 indicating indoor or outdoor, and an iterative subset of a distribution of scenario parameters 170. The explosive device model generator 162 generates an explosive device model based on the user inputs 112 and an iterative subset of a distribution of explosive device parameters 172. The propagation of hazards modeler 164 models propagation of hazards into the scenario based on the user inputs 112 and an iterative subset of a distribution of hazard parameters 174. The hazards correspond to detonation of the explosive device model from the explosive device model generator 162. The injury modeler 166 models injuries corresponding to the modeling propagation of hazards into the scenario based on an iterative subset of a distribution of injury parameters 176. The medical mitigation response modeler 168 models a medical mitigation response based on the injuries and an iterative subset of a distribution of medical mitigation parameters 178. The iteration and output generator 169 iterates by using additional iterative subsets of the distribution of scenario parameters 170, distribution of explosive device parameters 172, distribution of hazard parameters 174, distribution of injury parameters 176, and distribution of medical mitigation parameters 178 to generate the scenario, generate the explosive device model, model propagation of hazards, model injuries, and model the medical mitigation response until parameter spaces of the distribution of scenario parameters 170, distribution of explosive device parameters 172, distribution of hazard parameters 174, distribution of injury parameters 176, and distribution of medical mitigation parameters 178 are covered. The computer system 130 can generate output including an injury record 180, based on a plurality of injury outcomes from the modeling of injuries corresponding to the iterating, and a medical mitigation response record 182, based on a plurality of medical mitigation response outcomes from the modeling of medical mitigation responses corresponding to the iterating.

The computational models underlying the HExCAT application are Monte-Carlo probabilistic models. Parameters driving the models are defined as distributions quantifying the uncertainty associated with the parameter. When users define a scenario to be generated by the scenario generator 160, they also select a number of simulations to execute (e.g., a number of iterations); a unique set of scenarios corresponding to that number are constructed and executed, with each scenario defined by sampling from the distributions. To generate scenarios or other models or generated results, the computing system 130 can draw source data from databases, whether stored on computing system 130, or retrieved over network 102 from local server 104 or remote server 106.

The outcome from running a scenario is an ensemble of results corresponding to the number of simulations executed. This allows users to observe the range of possible outcomes from the defined scenario. As the user increases specificity of the scenario by reducing uncertainty in the parameters driving the model, the variation of possible outcomes will reduce. This probabilistic approach is very powerful as it allows users to define highly uncertain scenarios with minimal input and identify the worst-case outcomes and potential strategies to mitigate these outcomes. The HExCAT explosive and medical mitigation models are first principal models utilizing engineering assumptions and correlations to reduce model runtime. The models execute on the order of 10 ms per simulation (based on an exemplar COTS computer system 130 having the following characteristics: 1 TB solid state drive, 32 GB RAM, i7 processor, multi-core, greater than 2 Ghz, greater than 6 MB cache); this means that a user can execute 1,000 unique scenarios in approximately 10 s.

Figure 2:
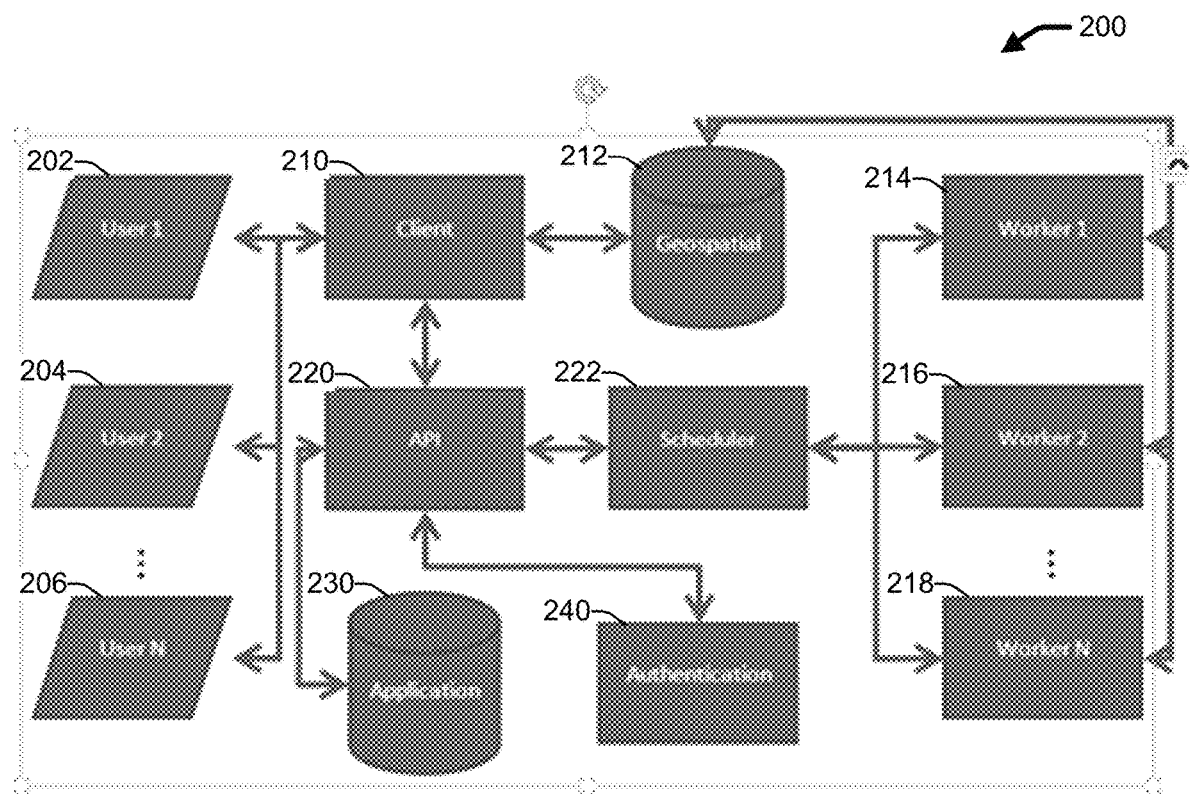
FIG. 2 illustrates an application diagram for HExCAT according to an embodiment.

FIG. 2 illustrates an application diagram 200 for HExCAT. A plurality of users (User1 202, User2 204, . . . , UserN 206) interface with client 210. Client 210 interfaces with geospatial database 212 and API 220. The API 220 interfaces with scheduler 222, application database 230, and authentication database 240. The scheduler interfaces with a plurality of workers (Worker1 214, Worker2 216, . . . , WorkerN 218). The plurality of workers interface with geospatial database 212.

In an embodiment, the HExCAT application consists of three ASP.NET Core Servers, two PostgreSQL database servers, a RabbitMQ scheduler server, and a Keycloak authentication server. The Client 210 server is responsible for handling user requests and routing those requests to the API 220 layer as appropriate. The Client 210 server also interacts with the Geospatial database 212 to gather geospatial resources to display to the users (User1 202, User2 204, . . . , UserN 206), such as maps. This Client 210 server includes a VueJs frontend which facilitates user interactions. The API 220 layer is responsible for interacting with the application database 230 to perform operations such as getting model parameter data, creating new jobs, and the like. The API 220 layer also sends scenario runs to be executed to the Scheduler 222 layer, as well as routes authentication requests to the Authentication 240 layer. The Scheduler 222 is responsible for dividing scenario run requests submitted to users (User1 202, User2 204, . . . , UserN 206) across the Worker layers (Worker1 214, Worker2 216, . . . , WorkerN 218) available and providing results back to the API 220 from the workers (Worker1 214, Worker2 216, . . . , WorkerN 218). The Authentication database 240 is responsible for authenticating user credentials to allow authorized access to the Client 210 and API 220 layers. The Workers (Worker1 214, Worker2 216, . . . , WorkerN 218) are responsible for executing scenario run requests and providing results back to the API 220 through the scheduler 222. The workers (Worker1 214, Worker2 216, . . . , WorkerN 218) interact with the explosive model and medical mitigation model using the defined scenarios to generate these results. The application database 230 stores information about the application, from users (User1 202, User2 204, . . . , UserN 206) and access to model configuration files defining the parameters in the models. The geospatial database 212 contains all geospatial resources utilized in model execution, from hospitals to outdoor populations.

Figure 3:
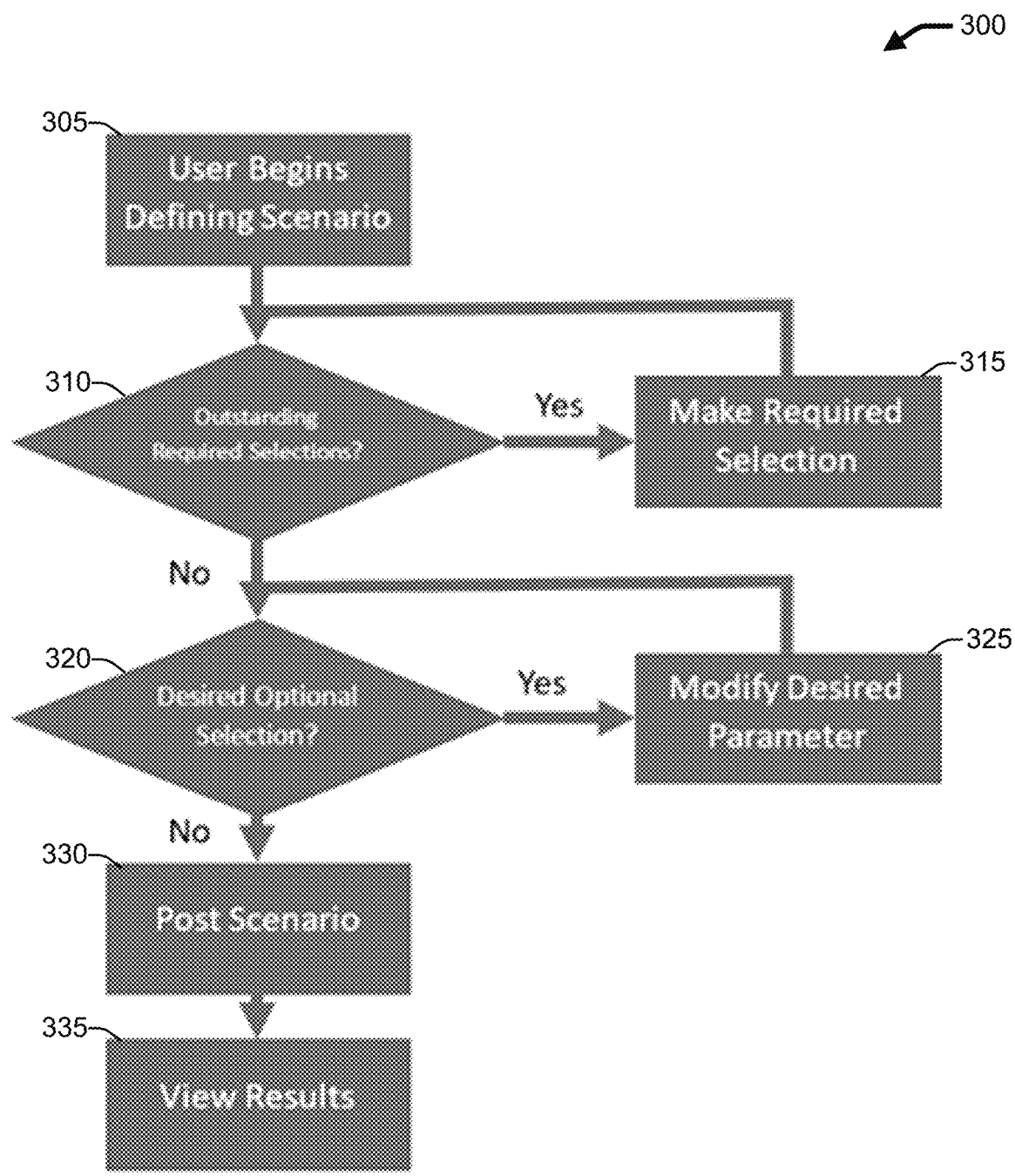
FIG. 3 illustrates a decision diagram which displays a process through which a user interacts with HExCAT to define a scenario, execute that scenario and obtain results according to an embodiment.

FIG. 3 illustrates a decision diagram 300 which displays a process through which a user interacts with HExCAT to define a scenario, execute that scenario and obtain results according to an embodiment. The user begins defining a scenario at 305. At 310, a check for outstanding required selections is performed. If there are outstanding required selections, users make a variety of selections for required parameters at 315. If the required parameters are not selected, the user will not be able to submit jobs and be prompted to make the required selections. The required selections for each model are shown in Table 1 below. To run a scenario, the user must choose either an indoor or an outdoor target. However, the user can choose to not run the medical mitigation model. For an indoor target selection, the target type controls the type of building which will be simulated. For an outdoor location, the target type controls the target location options based on the selection; for example, a selection of Urban Center as the target yields a list of cities, while a selection of Stadium yields a list of stadiums. For both indoor and outdoor attacks, the device must be specified by providing the explosive material and the fuel for that explosive. The medical mitigation model requests a selection in the case of indoor runs because the location of the attack is used to determine the hospitals and population impacting the medical response. The attack location is defined for outdoor attacks based on the Target Location selection. The selections made by the user are included in the work request and utilized by the Worker layer to determine which models to execute and how to execute them. If there are no further outstanding required selections at 310, flow proceeds to 320 to check for desired optional selections.

TABLE 1

Required selections for selected models

| Model | Required Selections |
|---|---|
| Indoor | 1. Model Type (Indoor or Outdoor) |
| | 2. Target Type (e.g., Shopping Mall) |
| | 3. Explosive Material (e.g., Ammonium Nitrate) |
| | 4. Explosive Fuel (e.g., Diesel) |
| Outdoor | 1. Model Type (Indoor or Outdoor) |
| | 2. Target Type (e.g., Urban Center) |
| | 3. Target Location (e.g., Columbus Ohio) |
| | 4. Explosive Material (e.g., Ammonium Nitrate) |
| | 5. Explosive Fuel (e.g., Diesel) |
| Medical Mitigation | 1. Attack Location (for indoor attacks only) |

In addition to selecting the required parameters, users also can modify optional or desired parameters at 325 to provide greater specificity for the scenario they are defining. The baseline for each parameter is intended to represent the distribution of values expected across the United States. Parameters described in the subsequent sections of this document can be modified by users when defining scenarios. Where applicable, parameters are defined as distributions, allowing users to best represent the uncertainty of the scenario that they are simulating. Changes made by users to optional parameters are included in the scenario run sent to the worker, and the details of the changes are used by the worker to modify the model configuration files prior to executing the simulations.

After desired parameters have been defined and no desired optional selections are outstanding, flow proceeds from 320 to 330. The user can run the scenario with a variety of input settings. As the underlying explosive model and medical mitigation model are pseudo-random probabilistic models; seeds are used to control repeatability of results from the models. The user has the option to modify the input seeds if desired; the same user selections with the same seeds will also generate identical results. In addition to the seeds, the user is also able to select the number of simulations to run. In cases where a high amount of uncertainty is present in the underlying parameters, a higher number of simulations are required to fully define the potential parameter outcomes. Users may also choose the number of simulations to run based on time requirements; additional simulations will take more time to execute the scenario and provide results. After the desired settings are set, users can click a button to post the scenario 330 to the API layer, which will store the requisite information in the database and pass the scenario to the scheduler.

After a job has been posted 330 and the simulation has been completed, results will be provided back to the user via the API. This will allow the users to navigate to a new page to view the results 335. In an embodiment, results from the application are a point value for a set of information per simulation. For example, if a user selects to run 1,000 simulations for a selected scenario, then 1,000 outputs of life-threatening injuries will be in the outputs corresponding to the 1,000 unique simulations executed as part of the scenario run. Life threatening injuries would be one example of many of the set of 1000 outputs which can be displayed. Other outputs include sublethal injuries, fraction saved, medical resources consumed, and so on.

Figure 4:
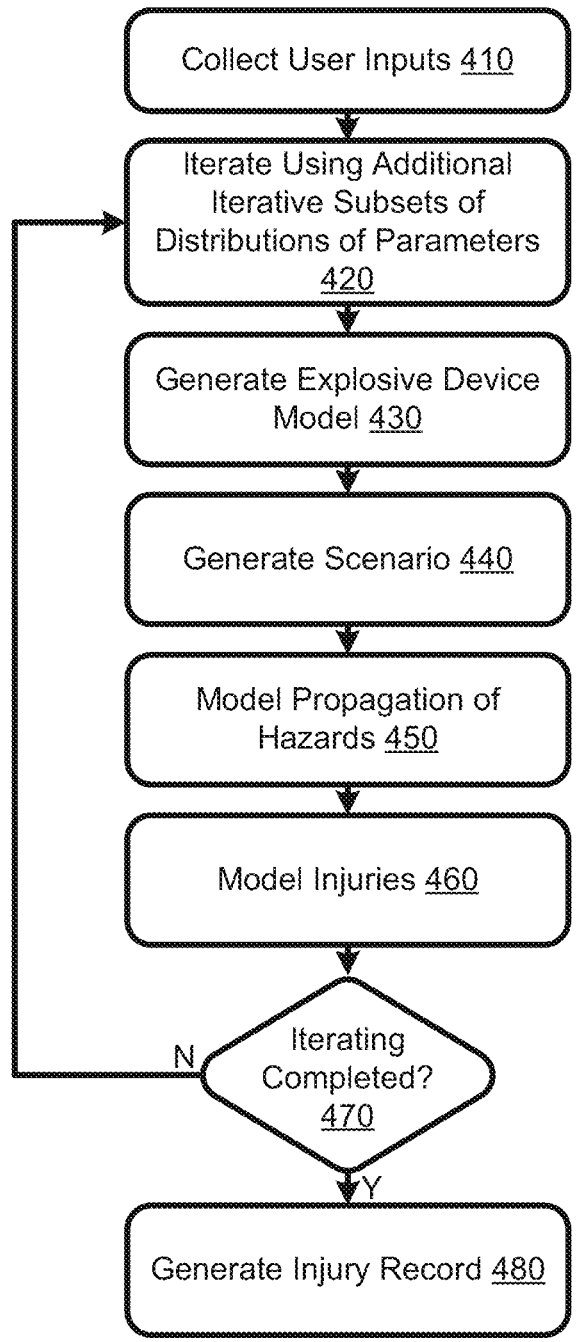
FIG. 4 illustrates a flowchart to generate an injury record according to an embodiment.

FIG. 4 illustrates a flowchart 400 to generate an injury record according to an embodiment. The illustrated process allows for defining a scenario in terms of target type, the representative target and location, whether an outdoor target is selected, and so on as shown at 410, at which the computer system collects user inputs. For example, the user can provide required information, such as whether the scenario is indoor or outdoor, and optional information, such as a specific type of building to model. The user then opts to sample from the full set of distributions defining the target, or a subset from those distributions at 420, at which the computer system iterates using additional iterative subsets of distributions of parameters. For example, the computer system uses a pseudo random approach to select which of a range of parameters to use for a given iteration. A given iteration may involve modeling an explosive device having a mass of 5 kg, whereas another iteration may involve modeling an explosive device having a mass of 10 kg, where the user specified user inputs indicating the mass of the explosive device can range from 5-20 kg. The user then selects the explosive material, charge mass or range, casing, and presence of thermal or fragmentation enhancements to define the explosive device at 430, at which the computing system generates an explosive device model. For example, the computing system models a device of a given mass, material type, and fuel type. At 440, the computer system generates a scenario. For example, the computing system models several blocks of buildings forming an entire cityscape. With the target and device defined in this manner, the model can then propagate the hazard generated by that device in that target, sampling a single value per iteration from each of the parameter distributions to compute a unique hazard at 450, at which the computing system models propagation of hazards. For example, the computing device simulates multiple ways that detonation of the explosive device model would affect the various buildings and simulated populations in those buildings of the simulated cityscape. The physical phenomena from the hazard propagation are then translated into expected injuries based on overpressure, fragmentation, thermal effects and building collapse at 460, at which the computer system models injuries. For example, the computer system applies more severe injuries to populations located closer to the device location. This is repeated, drawing new values from the distributions for each parameter for each new simulation, at 470 at which the computer system checks whether iteration has completed. For example, the computer system uses a Monte-Carlo probabilistic analysis to determine whether a sufficient subset of possible permutations of parameters have been simulated to cover the parameter space while also avoiding skewing the coverage. If iterating is not complete, flow loops back from 470 to 420, to iterate by repeating 420, 230,

440, 450, and 460. If iterating is complete, flow proceeds from 470 to 480. When the last simulation is completed, the injury record is returned and can be displayed or tabulated in a variety of ways at 480, at which the computer system generates an injury record. For example, the computing system outputs a list of victims, along with their injuries and the injury severities.

Figure 5:
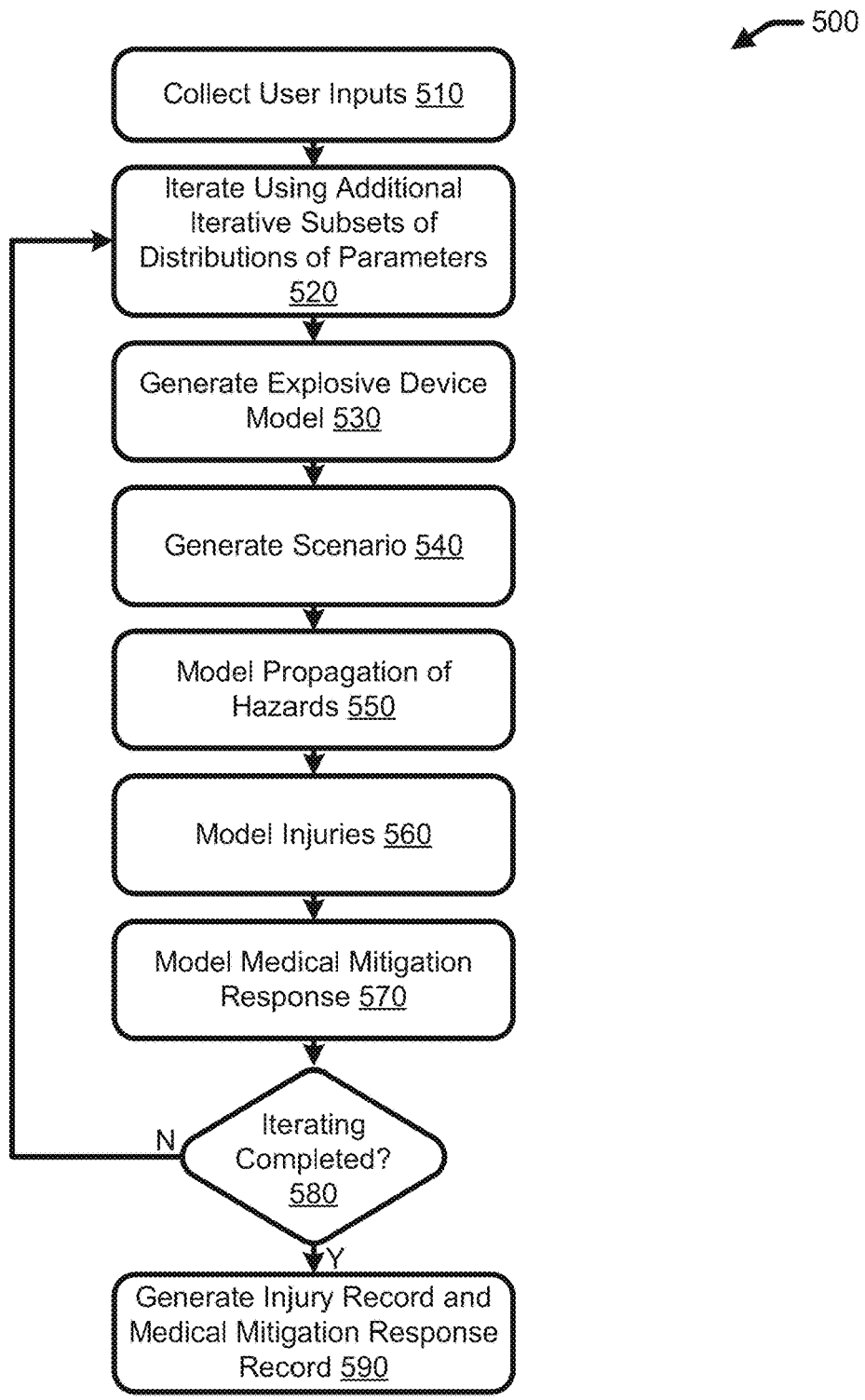
FIG. 5 illustrates a flowchart to generate an injury record and a medical mitigation response record according to an embodiment.

FIG. 5 illustrates a flowchart 500 to generate an injury record and a medical mitigation response record according to an embodiment. Procedures illustrated in FIG. 5 can be similar to those described above with respect to FIG. 4. At 510, the computer system collects user inputs. At 520, the computer system iterates using additional iterative subsets of distributions of parameters. At 530, the computing system generates an explosive device model. At 540, the computer system generates a scenario. At 550, the computing system models propagation of hazards. At 560, the computer system models injuries. At 570, the computer system models medical mitigation responses 570. For example, the computing system determines how many victims can receive medical assistance, how long it takes to receive care, how many victims are benefitted, and so on. The expected injuries and associated symptomatic timelines are passed to the medical mitigation model where the on-scene, in-transport and at-hospital triage and care are modeled based on resource, timing and efficacy parameters characterized by distributions. At 580, the computer system checks whether iteration has completed. If iterating is not complete, flow loops back from 580 to 520, to iterate by repeating 520, 530, 540, 550, 560, and 570. If iterating is complete, flow proceeds from 580 to 590. At 590, the computer system generates an injury record and a medical mitigation response record. For example, the computer system outputs a list of victims, along with their injuries and the injury severities, and how many victims benefit from medical response and how long until they receive care.

Scenario Generation

The HEXCAT tool enables the user to select an interior or exterior scenario, indicating the placement of the device inside a structure, or exterior to structures. A representative target type reflecting different types of structures for an interior scenario (e.g. museums, subway stations, airports) or a representative space for exterior scenarios (e.g. city centers, outdoor special events (e.g. festivals, New Year's Eve celebrations), sports stadia) is selected, as well as device characteristics (explosive material, charge weight range, casing, thermal or fragmentation enhancements), and location ranges for the device (e.g., Interior: anywhere in a building, first floor only, perimeter of the building; Exterior scenarios: location at a specific latitude, longitude coordinate in a city, or randomly placed within a specified radius or sector around a point location). Based on this initial selection, a user specified number of scenarios (N) are probabilistically generated based on random draws (Monte Carlo sampling) from input distributions representing parameters such as building materials, size and shape of structures, (supplemented by city shape files where available), population density of the building or area, location of the device based on an initial range. Each scenario is unique based on these drawn values, and provide the basis with which to calculate the impact of an explosion using standard equations governing shock wave propagation, generation and venting of combustion gases, barrier failure, fragmentation from device casing, enhancements, barrier failure (size and velocity bins of fragments) and fragmentation propagation. Additionally, a number of parameters governing the response to an explosion including treatment regimens and efficacy, medical response system/resources and the Concept of Operations (CONOPS) of the response are included as distributions with a random draw from each distribution.

The scenario is thus defined by a combination of user determined parameters (e.g. representative target type, gross location (for exterior scenario), explosive type, casing and presence or absence of thermal or fragmentation enhancements) parameters drawn from established databases (e.g. city population density) and parameters drawn from baseline distributions (e.g. treatment and resource efficacy and availability). These parameters collectively define a scenario and allow the calculation of the human health and structural damage and the current ability of the health care system (on-scene, transportation and hospital) to respond using the appropriate interior or exterior consequence model and medical mitigation model described in detail in subsequent sections.

Figure 6:
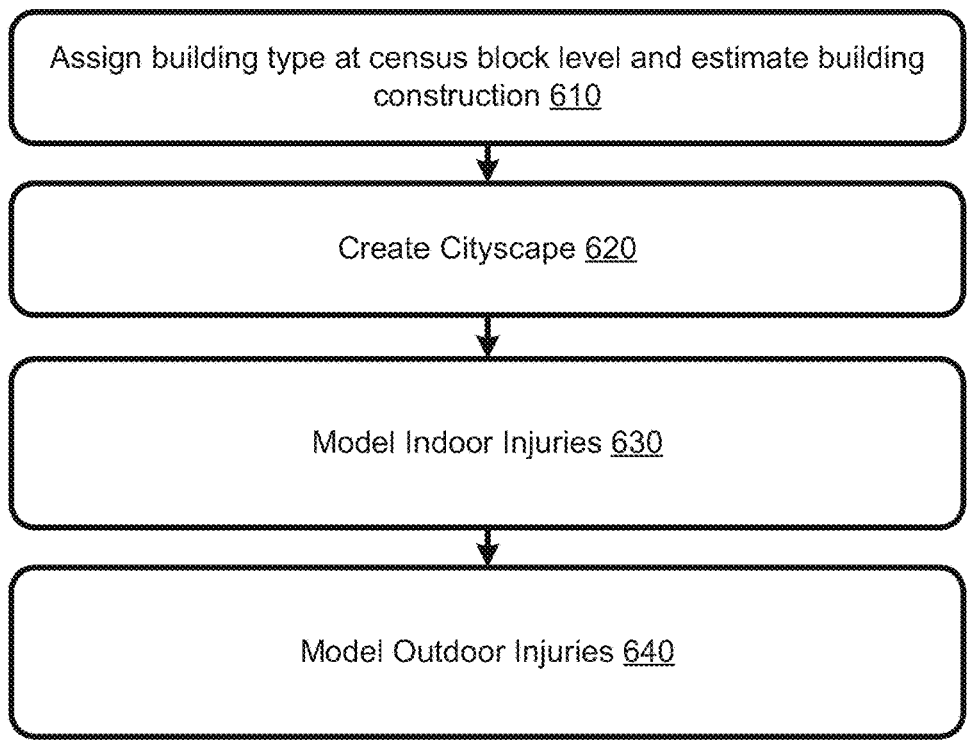
FIG. 6 illustrates a flowchart to model injuries according to an embodiment.

FIG. 6 illustrates a flowchart 600 to model injuries according to an embodiment. The computer system can apply cityscape generation to the exterior explosive module for both Fully Defined and Partially Defined cityscapes. Building size and type are randomly generated based on Hazus data by census block at 610, at which the computer system assigns building type at census block level and estimates building construction. For example, the computer system generates approximate cityscapes of multiple buildings without needing specific user inputs or detailed building model information. The collection of random buildings and types, governed by total area and use, is used to generate a unique cityscape for each simulation at 620, at which the computing system creates a cityscape. For example, the computing system access a database of general city and building information for a given location, and generates buildings of random characteristics that accurately reflect the general area of the given location. The impact of the exterior device on the occupants of the buildings is calculated at 630, at which the computer system models indoor injuries. For example, the computer system determines the injuries to populations inside buildings based on damage to the buildings involving fragmentation or building collapse. The hazard from the blast is propagated and the injuries calculated in the exterior space at 640, at which the computer system models outdoor injuries. For example, the computer system determines the injuries to populations outside buildings based on outdoor shockwaves and fireballs caused by detonation of the explosive device.

Indoor Scenario Generation

If an indoor scenario is selected, the user is queried for the type of interior space from the following list of representative targets:

Cruise Ship
Hospital
Office Building
Museum
Educational Institution
Airport Terminal
Shopping Mall
Religious Building
Theater
Hotel
Subway
Legislative Building
Arenas The target data are used to probabilistically generate the building parameters. For the Indoor Explosive Model (IEM), the Federal Emergency Management Administration's (FEMA) Hazus data (Hazus tool available at the FEMA government website) is sufficient to determine material and population information for the given targets.

The basic component unit of a building within the IEM is the grid cell, a singular rectangular prism of user-specified width, depth, and height. These dimensions effectively control the resolution of the IEM. Each grid tracks the local physical conditions—i.e., temperature, pressure, and impulse—as well as the relative location of all adjacent barriers and grids. Structural supports and the explosive device or devices are placed at specific coordinates within a grid. Additionally, each grid cell is assigned a population.

Physical hazards such as shockwave, debris, combustion gas, and building collapse are inherently continuous, as is the distribution of population throughout the building. Gridding the building into finite-sized distances allows the interior model to represent continuous phenomena in a tractable manner, while balancing runtime against fidelity.

Injury calculation is performed on the same grid framework with the key assumption that all individuals within a grid will experience a similar degree of exposure to each hazard. This assumption holds if the grid resolution—length and width—is kept small enough to reasonably approximate continuity. Typically, each grid dimension was specified in meters. The default size is 4 meters by 4 meters.

The gridding of the building allows calculations to be performed block by block to control blast effect propagation and injury assignment.

Barriers

Barriers are implemented to model interior and exterior walls, floors, and ceilings. When present, barriers are required to be located on the border between two adjacent grids. The barrier is constructed with a specified height and width that cannot exceed the corresponding dimensions of the adjacent grids.

Each barrier is composed of well-defined percentages of unique building materials where each material has its own structural properties. For instance, an external wall with a window may be represented within the IEM as a two-meter by two-meter barrier composed of 70% reinforced concrete slab and 30% double-pane glass. Due to the nature of grid discretization, it is unnecessary to further locate each material within the barrier. The overall thickness and strength of each barrier is derived from the thickness and strength of each component material.

Structural supports are a special type of barrier placed within grids to model load-bearing columns and spans. Like barriers, supports are composed of one or more component material, each with its own physical properties and failure curves. Unlike barriers, support dimensions are not tied to grid dimensions; a structural support could exceed the grid height and is not required to possess the same width as the grid.

Each structural support is constructed in such a way that it is responsible for supporting a specified number of grids above it. Building collapse is applied to the supported grids when a structural support fails due to debris, applied pressure and impulse, or venting.

Building Generators

A target building within the IEM is described as a discretized (or gridded) three-dimensional space at a specified resolution in each dimension. Each target contains barriers and structural supports that consist of material combinations specific to the building type selected. Each building has a unique cartesian location to place it relative to other buildings. Though this functionality is not fully utilized within the interior model, it is included for the HExCAT Exterior Consequence Model.

Each building was generated probabilistically within the model based on input distributions of several characterization parameters including:

The target building structure type;

The materials of construction;

The minimum barrier distance (as informed by the smallest room size);

The total surface area of the building;

The total number of floors in the building; and

The aspect ratio of the building.

Each target type considered in the IEM had a distribution of potential materials of construction, as extracted using the FEMA's Hazus dataset in combination with the International Building Codes. FEMA's Hazus methodology provided a nationally applicable standardized methodology for estimating losses due to natural disasters. One of Hazus's core functions is to estimate physical damage to residential and commercial buildings, as well as schools and other infrastructure.

For each structure, the number of floors and the population are determined from the surface area. Furthermore, building aspect ratio, room size, and room aspect ratio are input as a distribution. Parametrizing the scenario in this way ensures unique building layouts for each realization, thus allowing the IEM to capture the variability in consequences resulting from attacks on the full spectrum of possible target buildings. These parameters are passed to a "Compartmentalized" room generator to create a building with multiple similarly sized rooms connected by hallways.

Although this approach works for many buildings, it does not account for the unique considerations required when modeling certain buildings, such as shopping malls or airport terminals which cannot be characterized in the same way as an office building. For these cases, a specialized building generator was developed.

Compartmentalized

All compartmentalized buildings use the same generator functions, only with varied parameter values. Compartmentalized buildings are generated probabilistically within the model based on the following inputs:

The target building structure type;

The materials of construction;

Distribution of widths of rooms and hallways;

Distributions of aspect ratios for rooms and hallways;

The total surface area of the building;

The total number of floors in the building;

The aspect ratio of the building, and;

Population of the building.

For each structure, the number of floors and the population are determined with a dependency on the surface area. Furthermore, building aspect ratio, room size, and room aspect ratio are input as a distribution. Parametrizing the scenario in this way ensures unique building layouts for each realization, thus allowing the IEM to capture the variability in consequences resulting from attacks on the full spectrum of possible target buildings. These parameters are passed to the compartmentalized room generator to create a building with multiple similarly sized rooms connected by hallways. The exact parameters used for each of the building types are outlined in the following subsections.

Educational Institution

TABLE 2

Educational Institution Generator Parameters

Figure 7:
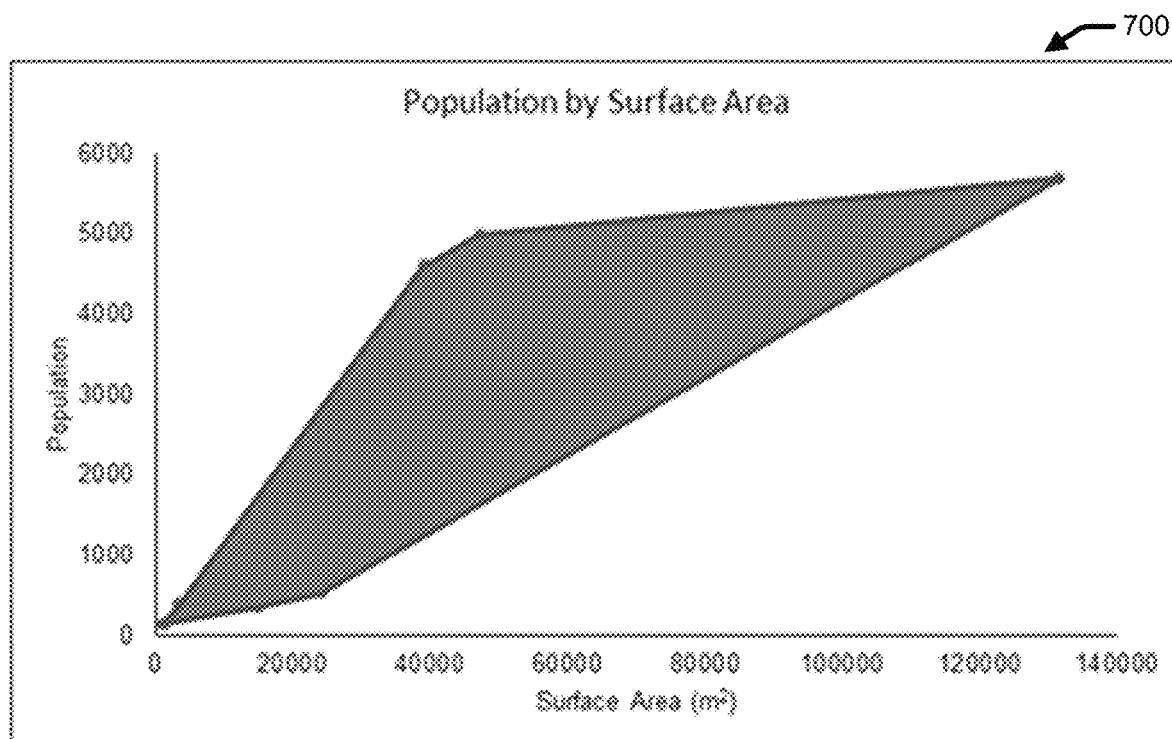
FIG. 7 illustrates Uniform Shape Distribution for Educational Institution Population according to an embodiment.

| Parameter | Description | Distribution | Values |
|---|---|---|---|
| Room Size | Width of a room | BetaPERT | Min: 4.0 m<br>Max: 25.0 m<br>Mode: 5.0 m<br>Weight: 0.8 m |
| Hallway Size | Width of a hallway | BetaPERT | Min: 2.0 m<br>Max: 8.0 m<br>Mode: 3.0 m<br>Weight: 0.2 m |
| Room Aspect Ratio | Width to length for a room | BetaPERT | Min: 1.0<br>Max: 4.0<br>Mode: 2.0<br>Weight: 0.8 |
| Hallway Aspect Ratio | Width to length for a hallway | BetaPERT | Min: 4.0<br>Max: 12.0<br>Mode: 10.0<br>Weight: 0.2 |
| Aspect Ratio | Aspect ratio of the whole building | BetaPERT | Min: 1.313<br>Max: 4.754<br>Mode: 2.630<br>Weight: 4.0 |
| Population by Surface Area | Population of the building as determined from the surface area | Uniform Shape | FIG 7. Uniform Shape Distribution for Population |
| Floor Count by Surface Area | Floor count as determined from the surface area | Uniform Shape Integer | FIG. 8. Uniform Integer Shape Distribution for Floor Count |

FIG. 7 illustrates a chart 700 of Uniform Shape Distribution for Educational Institution Population according to an embodiment.

Figure 8:
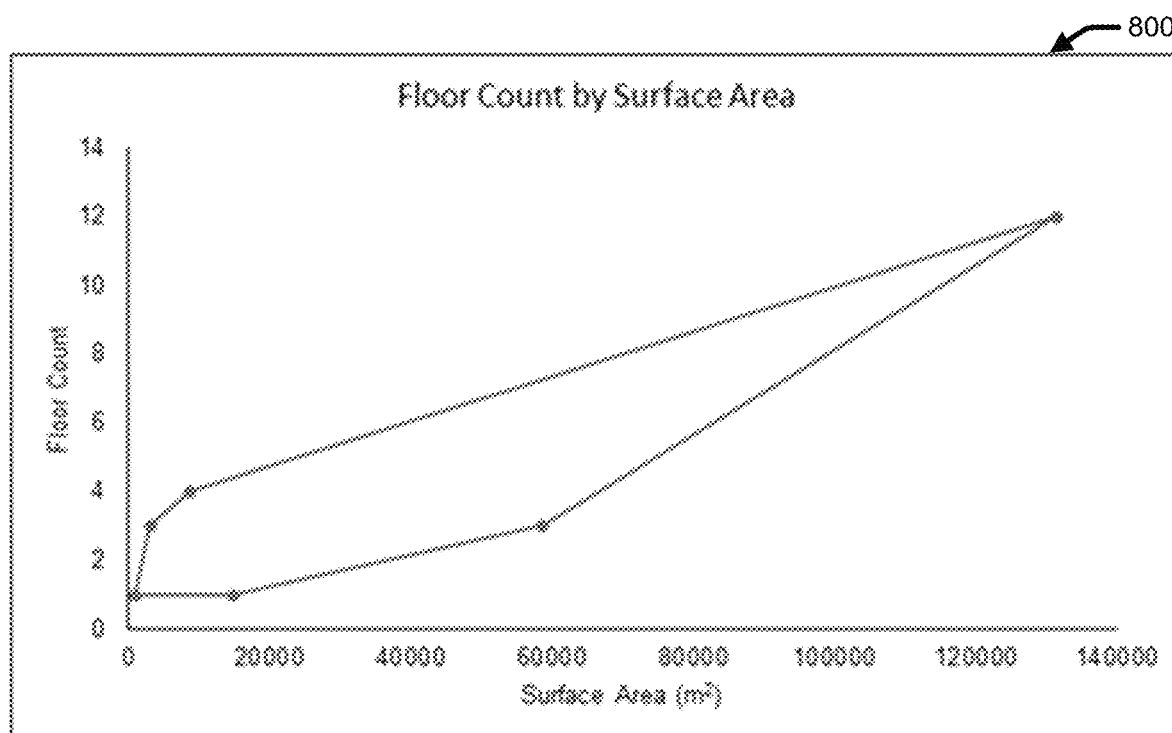
FIG. 8 illustrates Uniform Shape Integer Distribution for Educational Institution Floor Count.

FIG. 8 illustrates a chart 800 of Uniform Shape Integer Distribution for Educational Institution Floor Count according to an embodiment.

Materials of construction for Educational Institutions consist of wood, steel, masonry, and concrete. The materials of construction are an average taken from the Hazus designated building type EDU1. Table 3 has the material parameter weights listed.

TABLE 3

Educational Institution Material Distribution

| Material | Weight |
|---|---|
| Wood | 0.1075 |
| Steel | 0.4086 |
| Masonry | 0.2588 |
| Concrete | 0.2251 |

Hospital

TABLE 4

Hospital Generator Parameters

Figure 9:
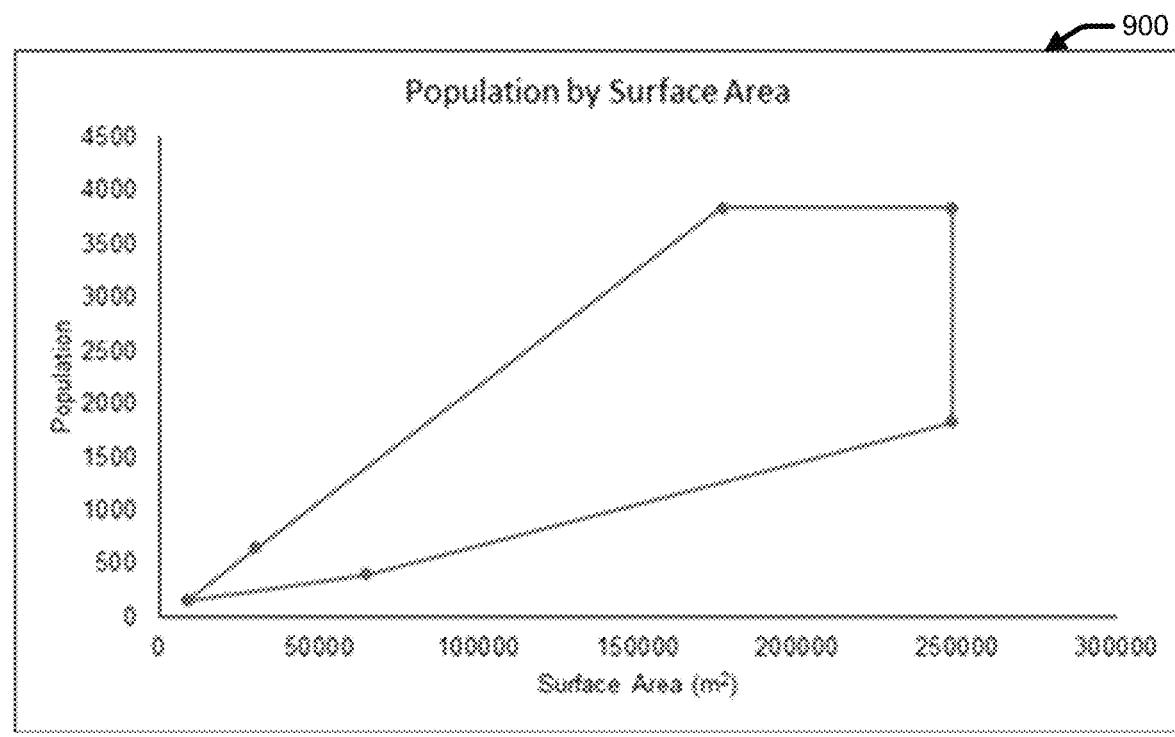
FIG. 9 illustrates Uniform Shape Distribution for Hospital Population according to an embodiment.

| Parameter | Description | Distribution | Values |
|---|---|---|---|
| Room Size | Width of a room | BetaPERT | Min: 4.0 m<br>Max: 25.0 m<br>Mode: 10.0 m<br>Weight: 0.8 m |
| Hallway Size | Width of a hallway | BetaPERT | Min: 2.0 m<br>Max: 8.0 m<br>Mode: 3.0 m<br>Weight: 0.2 m |
| Room Aspect Ratio | Width to length for a room | BetaPERT | Min: 1.0<br>Max: 4.0<br>Mode: 2.0<br>Weight: 0.8 |
| Hallway Aspect Ratio | Width to length for a hallway | BetaPERT | Min: 4.0<br>Max: 12.0<br>Mode: 10.0<br>Weight: 0.2 |
| Aspect Ratio | Aspect ratio of the whole building | BetaPERT | Min: 1.1<br>Max: 2.96<br>Mode: 1.776<br>Weight: 4.0 |
| Population by Surface Area | Population of the building as determined from the surface area | Uniform Shape | FIG. 9. Uniform Shape Distribution for Hospital Population |
| Floor Count by Surface Area | Floor count as determined from the surface area | Uniform Shape Integer | FIG. 10. Uniform Integer Shape Distribution for Hospital Floor Count |

FIG. 9 illustrates a chart 900 of Uniform Shape Distribution for Hospital Population according to an embodiment.

Figure 10:
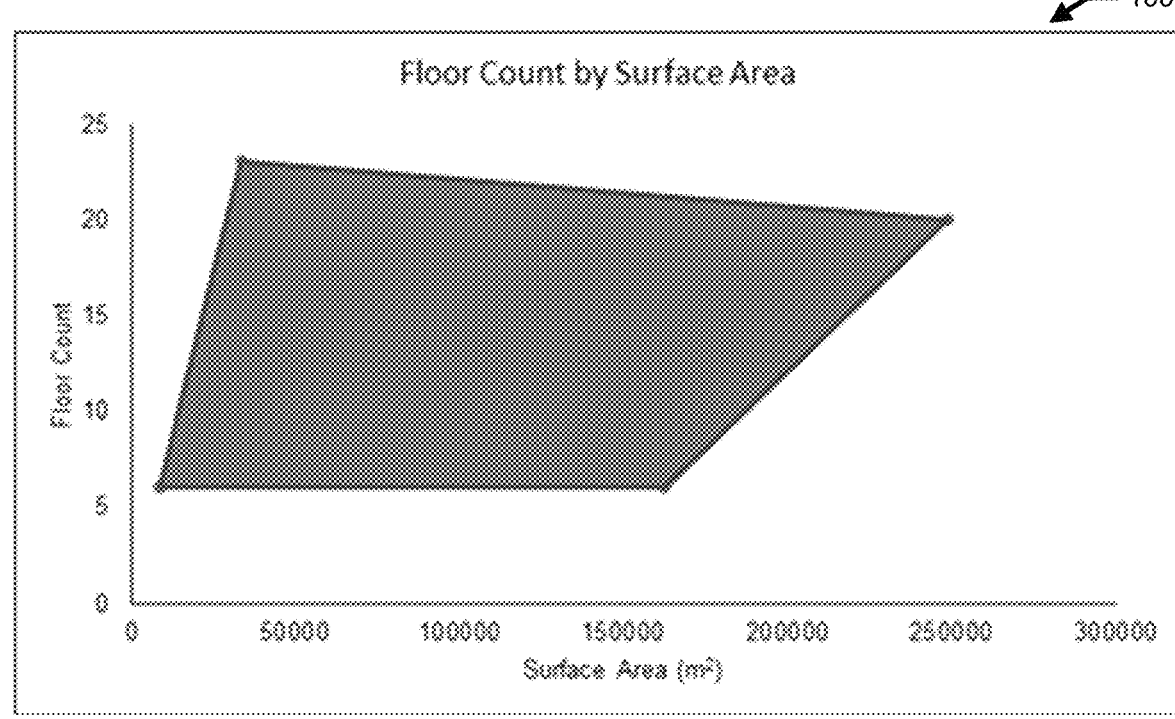
FIG. 10 illustrates Uniform Shape Integer Distribution for Hospital Floor Count according to an embodiment.

FIG. 10 illustrates a chart 1000 of Uniform Shape Integer Distribution for Hospital Floor Count according to an embodiment.

Materials of construction for Hospitals consist of wood, steel, masonry, and concrete. The materials of construction are an average taken from the Hazus designated building type COM6. Table 5 has the material parameter weights listed.

TABLE 5

Hospital Material Distribution

| Material | Weight |
|---|---|
| Wood | 0.1129 |
| Steel | 0.2557 |
| Masonry | 0.2284 |
| Concrete | 0.4032 |

Hotel

TABLE 6

Hotel Generator Parameters

| Parameter | Description | Distribution | Values |
|---|---|---|---|
| Room Size | Width of a room | BetaPERT | Min: 4.0 m<br>Max: 25.0 m<br>Mode: 5.0 m<br>Weight: 0.8 m |
| Hallway Size | Width of a hallway | BetaPERT | Min: 2.0 m<br>Max: 8.0 m<br>Mode: 3.0 m<br>Weight: 0.2 m |
| Room Aspect Ratio | Width to length for a room | BetaPERT | Min: 1.0<br>Max: 4.0<br>Mode: 2.0<br>Weight: 0.8 |
| Hallway Aspect Ratio | Width to length for a hallway | BetaPERT | Min: 4.0<br>Max: 12.0<br>Mode: 10.0<br>Weight: 0.2 |

TABLE 6-continued

Hotel Generator Parameters

Figure 11:
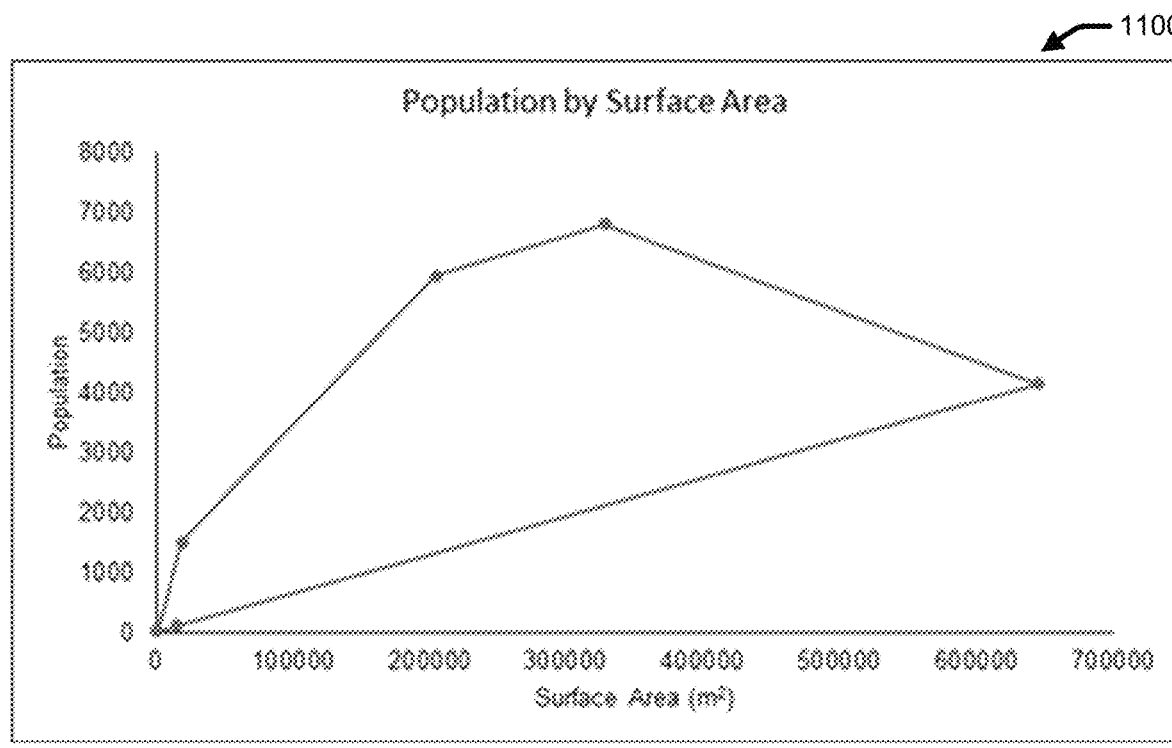
FIG. 11 illustrates Uniform Shape Distribution for Hotel Population according to an embodiment.

| Parameter | Description | Distribution | Values |
|---|---|---|---|
| Aspect Ratio | Aspect ratio of the whole building | BetaPERT | Min: 1.0<br>Max: 12.0<br>Mode: 2.7488<br>Weight: 4.0 |
| Population by Surface Area | Population of the building as determined from the surface area | Uniform Shape | FIG. 11. Uniform Shape Distribution for Hotel Population |
| Floor Count by Surface Area | Floor count as determined from the surface area | Uniform Shape Integer | FIG. 12. Uniform Shape Integer Distribution for Hotel Floor Count |

FIG. 11 illustrates a chart 1100 of Uniform Shape Distribution for Hotel Population according to an embodiment.

Figure 12:
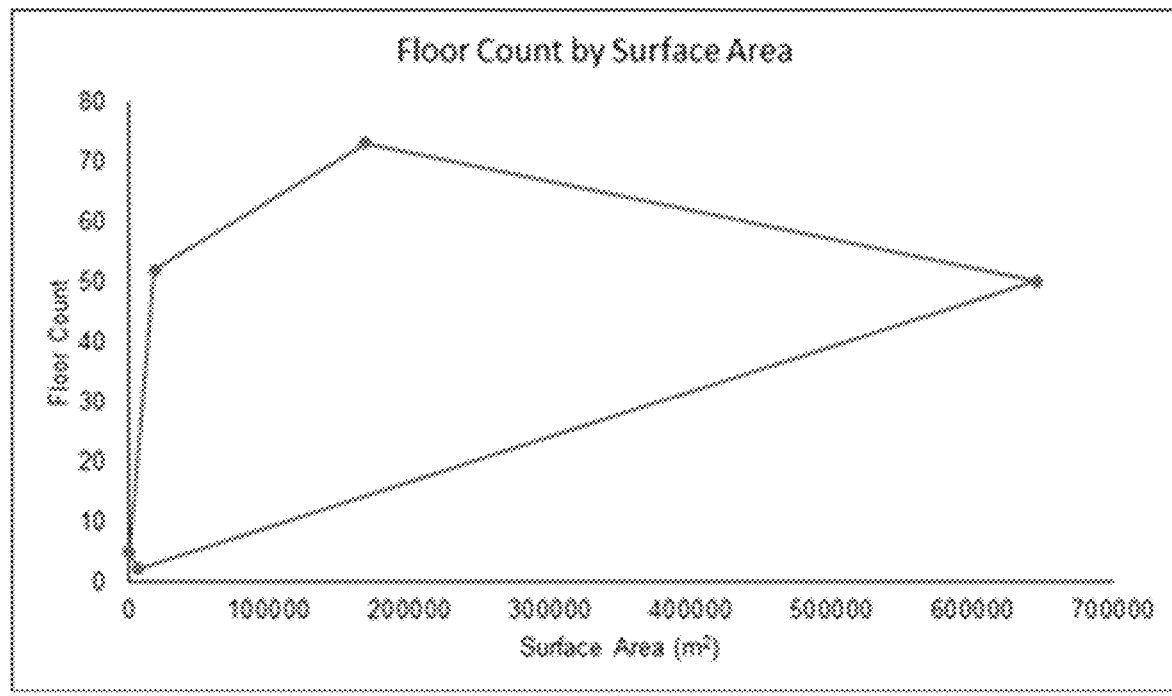
FIG. 12 illustrates Uniform Shape Integer Distribution for Hotel Floor Count according to an embodiment.

FIG. 12 illustrates a chart 1200 of Uniform Shape Integer Distribution for Hotel Floor Count according to an embodiment.

Materials of construction for Hotels consist of wood, steel, masonry, and concrete. The materials of construction are an average taken from the Hazus designated building type RES4. Table 7 has the material parameter weights listed.

TABLE 7

Hotel Material Distribution

| Material | Weight |
|---|---|
| Wood | 0.5055 |
| Steel | 0.0686 |
| Masonry | 0.3131 |
| Concrete | 0.1228 |

Museum

TABLE 8

Museum Generator Parameters

Figure 13:
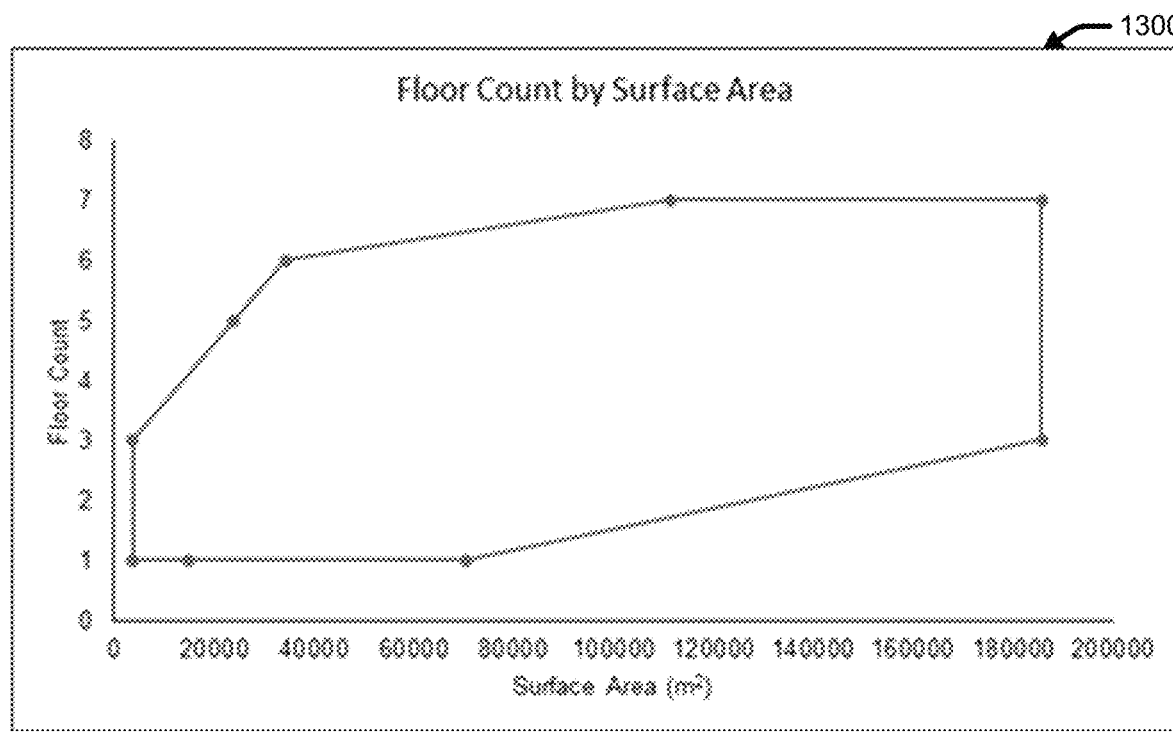
FIG. 13 illustrates Uniform Shape Distribution for Museum Population according to an embodiment.

| Parameter | Description | Distribution | Values |
|---|---|---|---|
| Room Size | Width of a room | BetaPERT | Min: 4.0 m<br>Max: 25.0 m<br>Mode: 10.0 m<br>Weight: 0.8 m |
| Hallway Size | Width of a hallway | BetaPERT | Min: 2.0 m<br>Max: 8.0 m<br>Mode: 3.0 m<br>Weight: 0.2 m |
| Room Aspect Ratio | Width to length for a room | BetaPERT | Min: 1.0<br>Max: 4.0<br>Mode: 2.0<br>Weight: 0.8 |
| Hallway Aspect Ratio | Width to length for a hallway | BetaPERT | Min: 4.0<br>Max: 12.0<br>Mode: 10.0<br>Weight: 0.2 |
| Aspect Ratio | Aspect ratio of the whole building | BetaPERT | Min: 1.07<br>Max: 7.1<br>Mode: 2.223<br>Weight: 4.0 |
| Population by Surface Area | Population of the building as determined from the surface area | Uniform Shape | FIG. 13. Uniform Shape Distribution for Museum Population |
| Floor Count by Surface Area | Floor count as determined from the surface area | Uniform Shape Integer | FIG. 14. Uniform Shape Integer Distribution for Museum Floor Count |

FIG. 13 illustrates a chart 1300 of Uniform Shape Distribution for Museum Population according to an embodiment.

Figure 14:
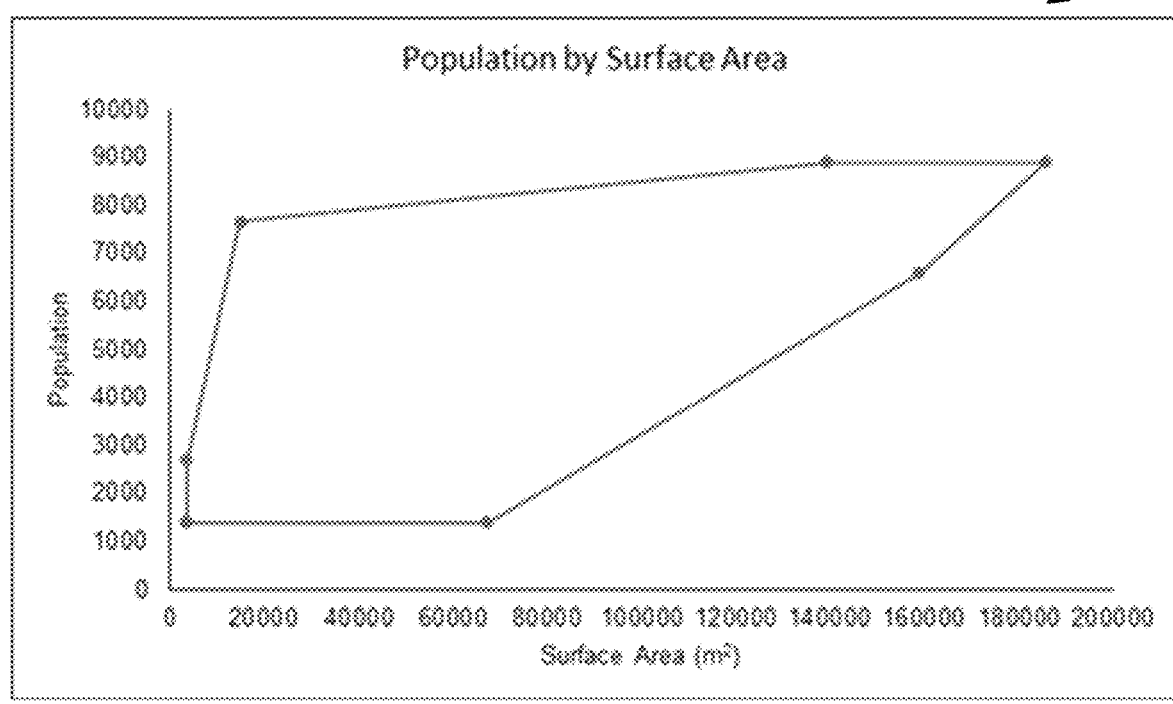
FIG. 14 illustrates Uniform Shape Integer Distribution for Museum Floor Count according to an embodiment.

FIG. 14 illustrates a chart 1400 of Uniform Shape Integer Distribution for Museum Floor Count according to an embodiment.

Materials of construction for Museums consist of wood, steel, masonry, and concrete. The materials of construction are an average taken from the Hazus designated building type RES4. Table 9 has the material parameter weights listed.

TABLE 9

Museum Material Distribution

| Material | Weight |
|---|---|
| Wood | 0.1787 |
| Steel | 0.3871 |
| Masonry | 0.3013 |
| Concrete | 0.1329 |

Cruise Ship

TABLE 10

Cruise Ship Generator Parameters

Figure 15:
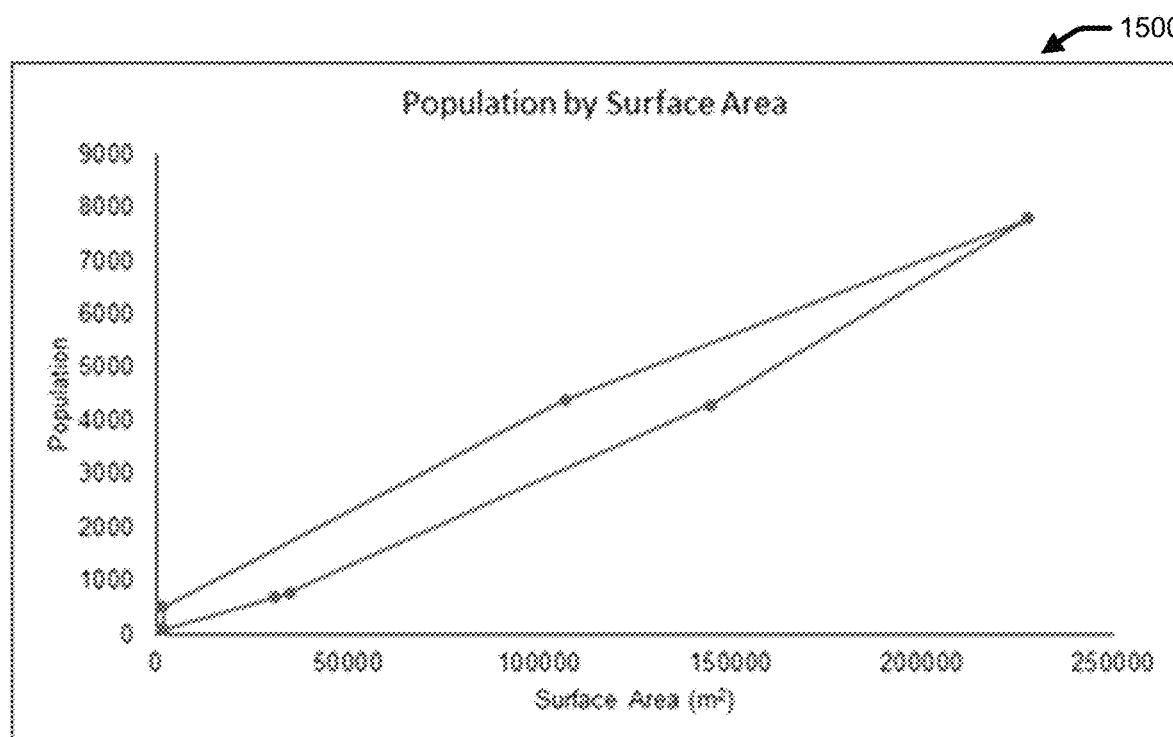
FIG. 15 illustrates Uniform Shape Distribution for Cruise Ship Population according to an embodiment.

| Parameter | Description | Distribution | Values |
|---|---|---|---|
| Room Size | Width of a room | BetaPERT | Min: 2.0 m<br>Max: 25.0 m<br>Mode: 5.0 m<br>Weight: 0.8 m |
| Hallway Size | Width of a hallway | BetaPERT | Min: 2.0 m<br>Max: 8.0 m<br>Mode: 3.0 m<br>Weight: 0.2 m |
| Room Aspect Ratio | Width to length for a room | BetaPERT | Min: 1.0<br>Max: 4.0<br>Mode: 2.0<br>Weight: 0.8 |
| Hallway Aspect Ratio | Width to length for a hallway | BetaPERT | Min: 4.0<br>Max: 12.0<br>Mode: 10.0<br>Weight: 0.2 |
| Aspect Ratio | Aspect ratio of the whole building | BetaPERT | Min: 3.303<br>Max: 9.191<br>Mode: 7.58<br>Weight: 4.0 |
| Population by Surface Area | Population of the building as determined from the surface area | Uniform Shape | FIG. 15. Uniform Shape Distribution for Cruise Ship Population |
| Floor Count by Surface Area | Floor count as determined from the surface area | Uniform Shape Integer | FIG. 16. Uniform Shape Integer Distribution for Cruise Ship Floor Count |

FIG. 15 illustrates a chart 1500 of Uniform Shape Distribution for Cruise Ship Population according to an embodiment.

Figure 16:
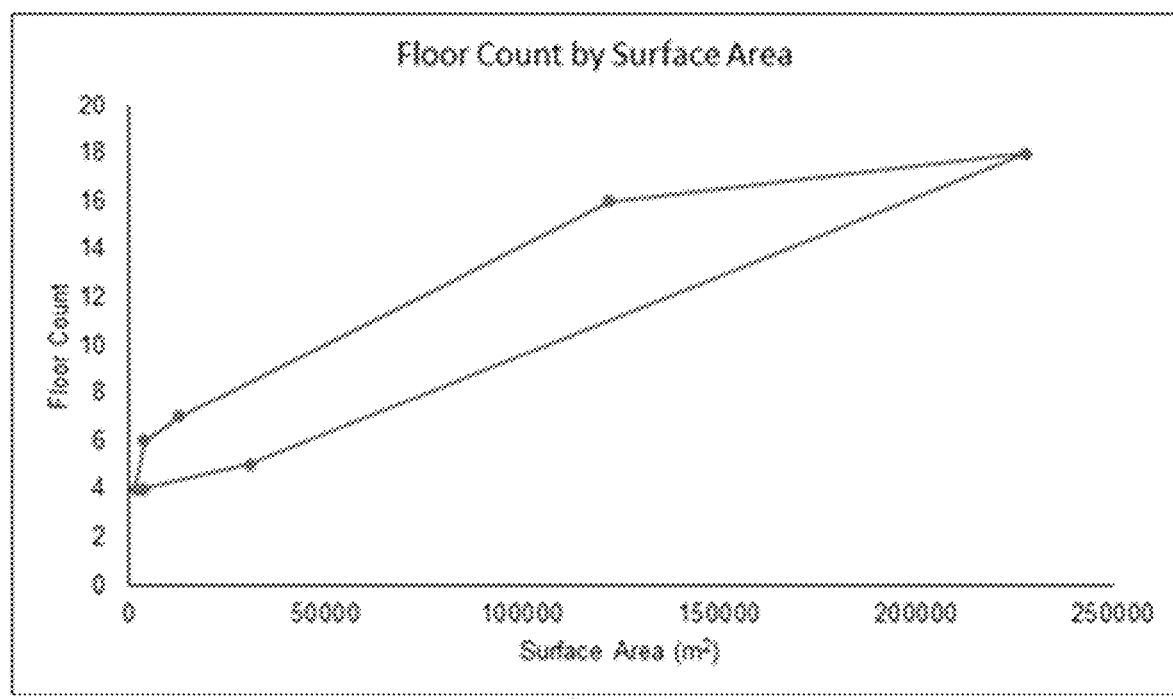
FIG. 16 illustrates Uniform Shape Integer Distribution for Cruise Ship Floor Count according to an embodiment.

FIG. 16 illustrates a chart 1600 of Uniform Shape Integer Distribution for Cruise Ship Floor Count according to an embodiment.

Materials of construction for Cruise Ships consist of wood and steel. Cruise ships do not have a building type in Hazus, though COM8 is used as a reasonable analogue. The material parameter weights listed are listed below.

TABLE 11

Cruise Ship Material Distribution

| Material | Weight |
|---|---|
| Wood | 0.25 |
| Steel | 0.75 |

Office Building

TABLE 12

Office Building Generator Parameters

Figure 17:
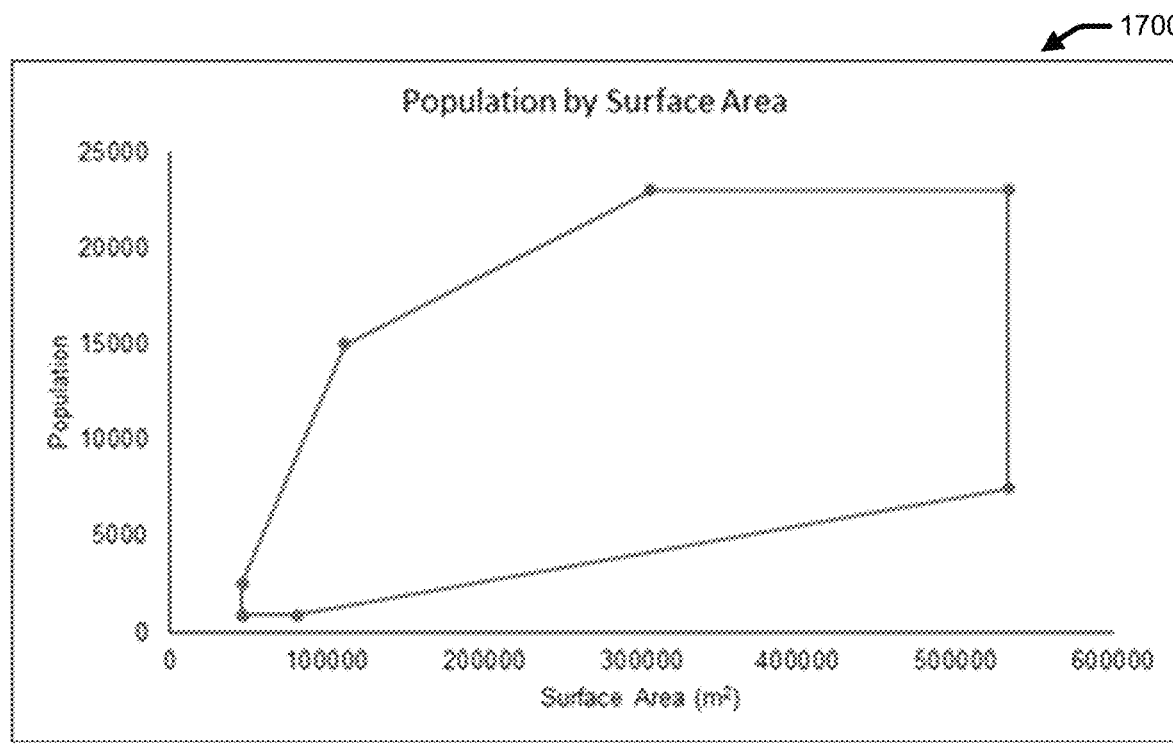
FIG. 17 illustrates Uniform Shape Distribution for Office Building Population according to an embodiment.

| Parameter | Description | Distribution | Values |
|---|---|---|---|
| Room Size | Width of a room | BetaPERT | Min: 4.0 m<br>Max: 25.0 m<br>Mode: 5.0 m<br>Weight: 0.8 m |
| Hallway Size | Width of a hallway | BetaPERT | Min: 2.0 m<br>Max: 8.0 m<br>Mode: 3.0 m<br>Weight: 0.2 m |
| Room Aspect Ratio | Width to length for a room | BetaPERT | Min: 1.0<br>Max: 4.0<br>Mode: 2.0<br>Weight: 0.8 |
| Hallway Aspect Ratio | Width to length for a hallway | BetaPERT | Min: 4.0<br>Max: 12.0<br>Mode: 10.0<br>Weight: 0.2 |
| Aspect Ratio | Aspect ratio of the whole building | BetaPERT | Min: 1.0<br>Max: 4.744<br>Mode: 1.857<br>Weight: 4.0 |
| Population by Surface Area | Population of the building as determined from the surface area | Uniform Shape | FIG. 17. Uniform Shape Distribution for Office Building Population |
| Floor Count by Surface Area | Floor count as determined from the surface area | Uniform Shape Integer | FIG. 18. Uniform Shape Integer Distribution for Office Building Floor Count |

FIG. 17 illustrates a chart 1700 of Uniform Shape Distribution for Office Building Population according to an embodiment.

Figure 18:
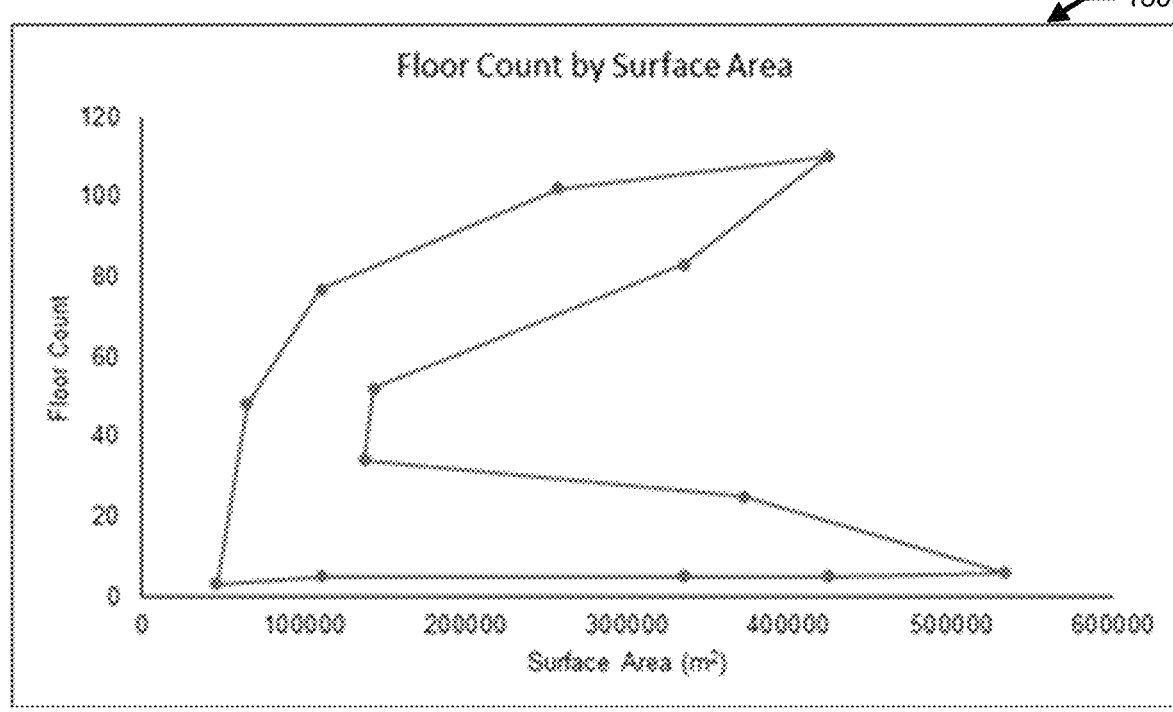
FIG. 18 illustrates Uniform Shape Integer Distribution for Office Building Floor Count according to an embodiment.

FIG. 18 illustrates a chart 1800 of Uniform Shape Integer Distribution for Office Building Floor Count according to an embodiment.

Materials of construction for Office Buildings consist of wood, steel, masonry, and concrete. The materials of construction are an average taken from the Hazus designated building type COM4. Table 13 has the material parameter weights listed.

TABLE 13

Office Building Material Distribution

| Material | Weight |
|---|---|
| Wood | 0.3059 |
| Steel | 0.2351 |
| Masonry | 0.2951 |
| Concrete | 0.1685 |

Open Buildings

Although the compartmentalized approach works for many buildings, each open building has some level of unique considerations which cannot be captured by a compartmentalized building generator. Seven of the 13 representative targets considered in the IEM are treated as open buildings (Airport terminal, Arena, Legislative Building, Religious Building, Shopping Mall, Subway and Theater). Every building generator used for open buildings has a unique set of input parameters required. As such, the list of each building's parameters is accompanied by a short description, outlining why these buildings require specialized generators.

Airport Terminal

An airport terminal is characterized by a large, high ceiling walkway down the center of the building with small shops along the sides. The airport terminal generator requires, in addition to the standard inputs, terminal width, terminal height, and terminal enclosure. Terminal height, unlike number of floors in other generators, does not add more floors but raises the ceiling reducing reflections from above. Terminal enclosure is used to model partially enclosed structures and may either be fully enclosed or no exterior walls. Notably, exterior walls which are part of stores are still generated. A breakdown of the parameters and their distributions can be found in Table 14.

TABLE 14

Airport Terminal Generator Parameters

| Parameter | Description | Distribution | Values |
|---|---|---|---|
| Terminal Width | The overall width of the terminal | Truncated Log Normal | Min: 19.0 m<br>Max: 141.0 m<br>Mean: 44.86 m<br>Stdev: 21.07 m |
| Terminal Height | Height of the terminal | Constant | 15 m |
| Terminal Enclosure | Type of exterior wall and ceiling enclosure for the airport terminal | Discrete Uniform | Full |
| Store Area | Surface area per store | Uniform | Min: 65.03 m<br>Max: 130.0 m |
| Store Aspect Ratio | Ratio of Width to Length | Uniform | Min: 1.0<br>Max: 4.0 |
| Residence Time | The time spent on average in a store | Truncated Log Normal | Min: 0.08 hours<br>Max: 5.0 hours<br>Mean: 0.88 hours<br>Stdev: 0.91 hours |

Materials of construction for the Airport Terminal consist of wood, steel, masonry, and concrete. The materials of construction are an average taken from the Hazus designated building type COM4. Table 15 has the material parameter weights listed.

TABLE 15

Airport Terminal Material Distribution

| Material | Weight |
|---|---|
| Wood | 0.3059 |
| Steel | 0.2351 |
| Masonry | 0.2950 |
| Concrete | 0.1638 |

Arena

An arena is any empty court surrounded by upward sloping stands. The arena generator also creates a mezzanine level of stands above the lower stands. The arena generator requires court length and court aspect ratio with both the population and height of the arena based on the total surface area. In Table 16. Arena Generator Parameters the specific values and parameter distributions are outlined.

TABLE 16

Arena Generator Parameters

Figure 19:
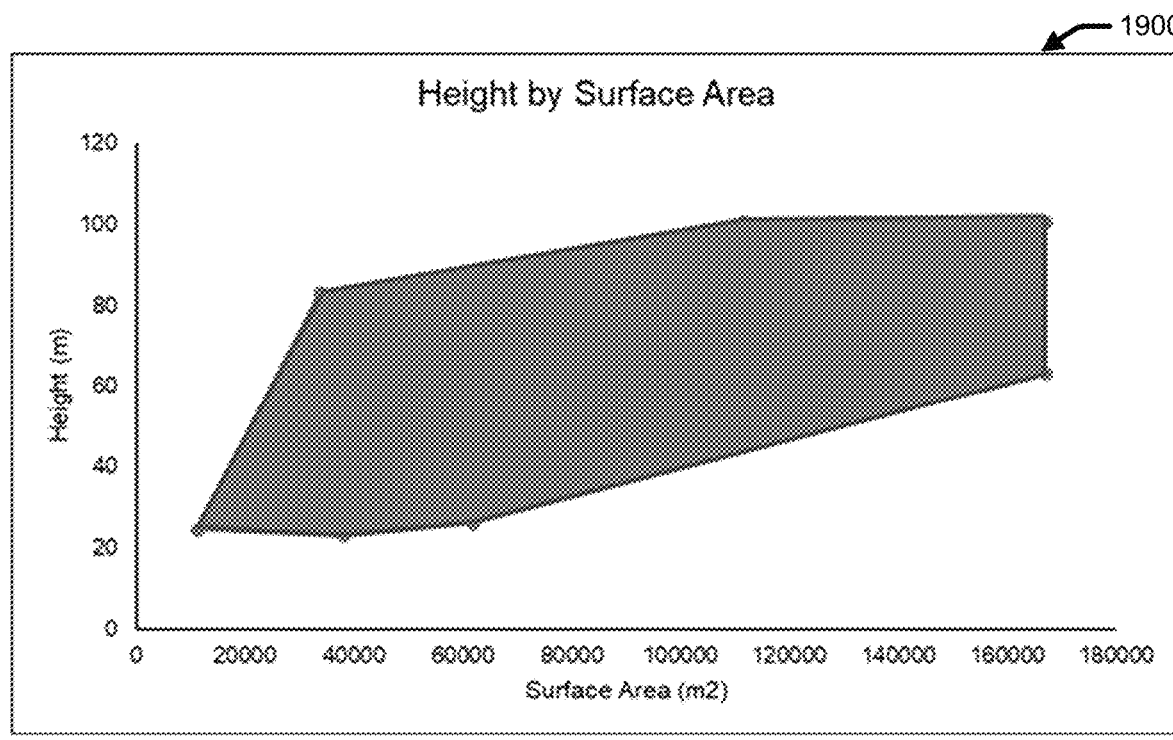
FIG. 19 illustrates Uniform Shape Distribution for Arena Height according to an embodiment.

| Parameter | Description | Distribution | Values |
|---|---|---|---|
| Court Length | Length of the court in the center of the arena | BetaPERT | Min: 30.48 m<br>Max: 121.9 m<br>Mode: 60.96 m |
| Court Aspect Ratio | Length:Width | BetaPERT | Min: 1.0<br>Max: 2.0<br>Mode: 1.22 |
| Height by Surface Area | Arena height as determined by the total surface area | Uniform Shape | FIG. 19. Uniform Shape Distribution for Arena Height |
| Population by Surface Area | Arena population per hour as determined by the total surface area | Uniform Shape | FIG. 20. Uniform Shape Distribution for Arena Population |

FIG. 19 illustrates a chart 1900 of Uniform Shape Distribution for Arena Height according to an embodiment.

Figure 20:
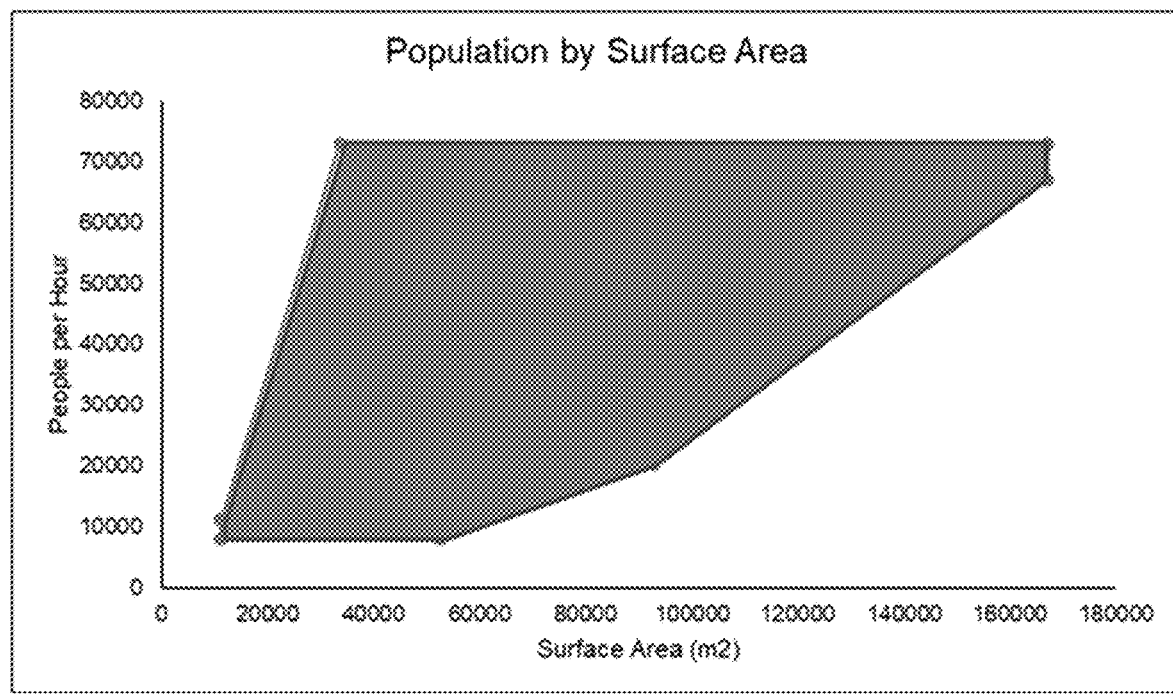
FIG. 20 illustrates Uniform Shape Distribution for Arena Population according to an embodiment.

FIG. 20 illustrates a chart 2000 of Uniform Shape Distribution for Arena Population according to an embodiment.

Materials of construction for the Arena consist of wood, steel, masonry, and concrete. The materials of construction are an average taken from the Hazus designated building type COM8. Table 17 has the material parameter weights listed.

TABLE 17

Arena Terminal Material Distribution

| Material | Weight |
|---|---|
| Wood | 0.1787 |
| Steel | 0.3870 |
| Masonry | 0.3013 |
| Concrete | 0.1328 |

Legislative Building

This style of building consists of a single large room with no interior walls. This is the simplest of all generators requiring only population, surface area, height, and aspect ratio. The parameter breakdown is shown in Table 18.

TABLE 18

Legislative/Religious Building Generator Parameters

Figure 21:
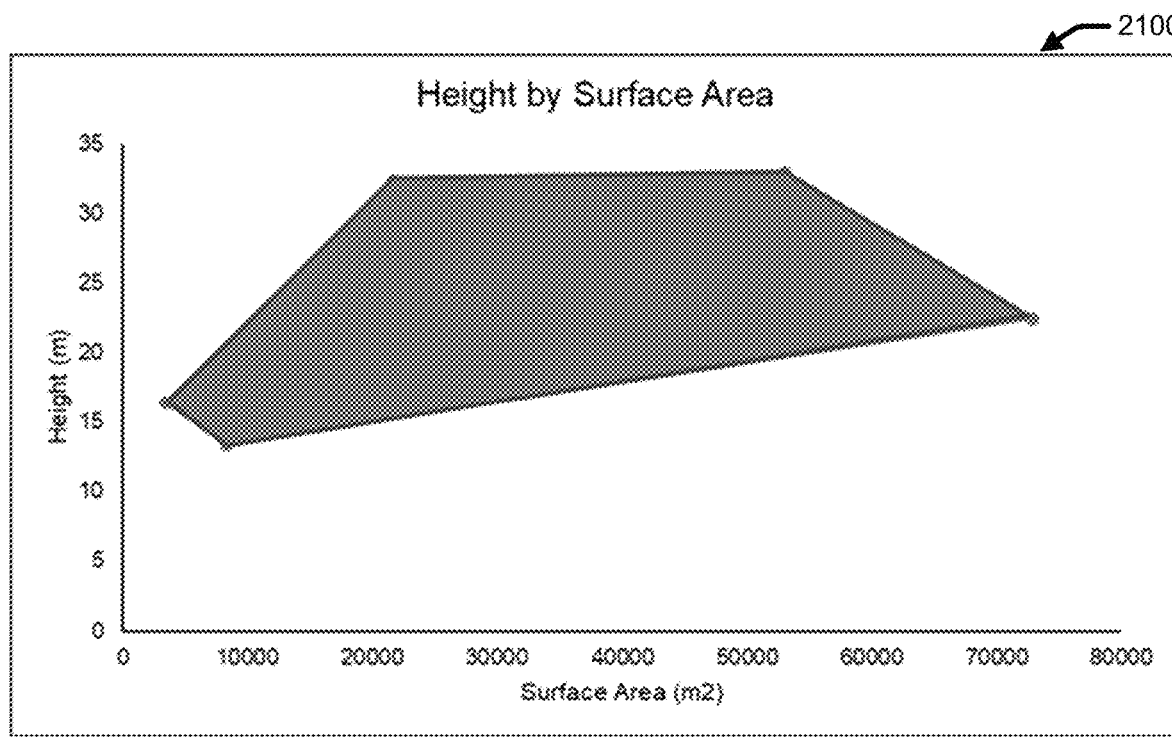
FIG. 21 illustrates Uniform Shape Distribution for Legislative/Religious Building Height according to an embodiment.

| Parameter | Description | Distribution | Values |
|---|---|---|---|
| Aspect Ratio | Width:Length | BetaPERT | Min: 1.0<br>Max: 3.0<br>Mode: 1.87 |
| Height by Surface Area | Legislative/Religious Building height as determined by the total surface area | Uniform Shape | FIG. 21. Uniform Shape Distribution for Legislative/Religious Building Height |
| Population by Surface Area | Legislative/Religious Building population per hour as determined by the total surface area | Uniform Shape | FIG. 22. Uniform Shape Distribution for Legislative/Religious Building Population |

FIG. 21 illustrates a chart 2100 of Uniform Shape Distribution for Legislative/Religious Building Height according to an embodiment.

Figure 22:
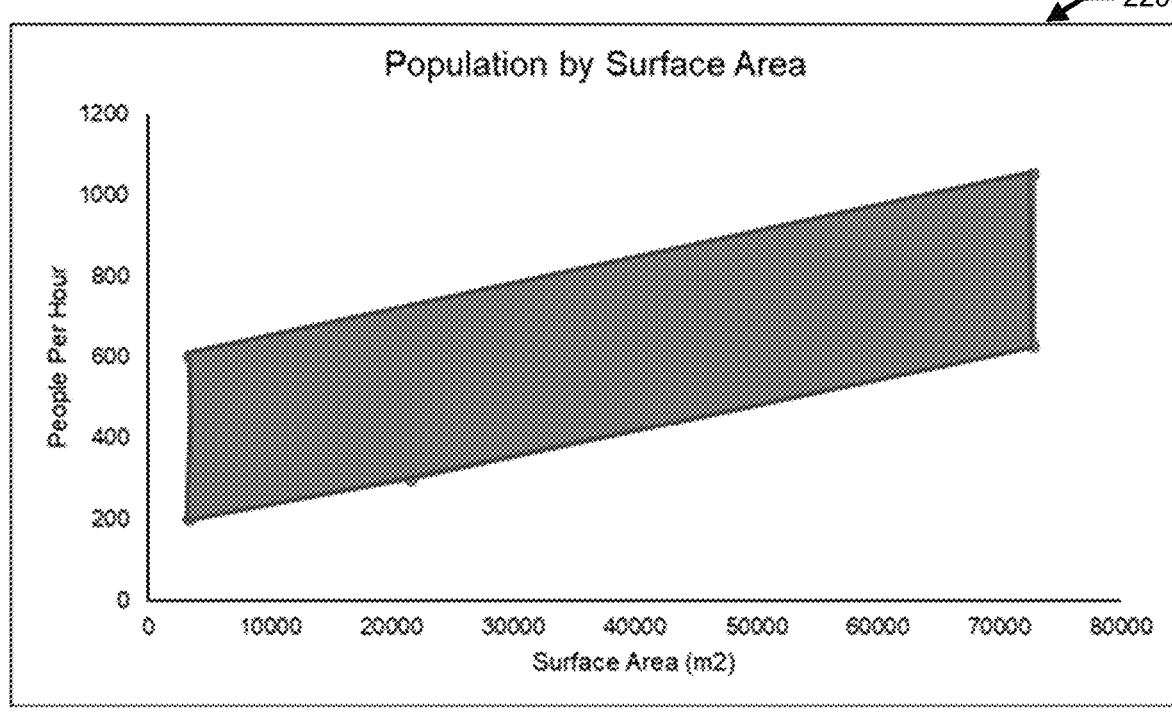
FIG. 22 illustrates Uniform Shape Distribution for Legislative/Religious Building Population according to an embodiment.

FIG. 22 illustrates a chart 2200 of Uniform Shape Distribution for Legislative/Religious Building Population according to an embodiment.

Materials of construction for the Legislative/religious Building consist of wood, steel, masonry, and concrete. The materials of construction are an average taken from the Hazus designated building type GOV1/REL1 Table 19 has the material parameter weights listed.

TABLE 19

Legislative/Religious Building Material Distribution

| Material | Weight (Legislative/Religious) |
|---|---|
| Wood | 0.1527/0.2940 |
| Steel | 0.2630/0.1623 |
| Masonry | 0.4013/0.3887 |
| Concrete | 0.1782/0.1549 |

Shopping Mall

The shopping mall buildings are characterized by a large, multi-level hallway surrounded on each floor by a unique layout of two distinct store types: small stores and anchor stores. The Shopping mall generator requires population, surface area, number of anchor stores, number of small stores, number of floors, ratio of anchor store area to small store area, anchor store aspect ratio, hallway width and the ratio of storage space to public space. The parameter details can be found in Table 20.

TABLE 20

Shopping Mall Generator Parameters

| Parameter | Description | Distribution | Values |
|---|---|---|---|
| Anchor Aspect Ratio | Anchor store aspect ratio (Width:Length) | Uniform | Min: 1.0<br>Max: 2.5 |

TABLE 20-continued

Shopping Mall Generator Parameters

Figure 23:
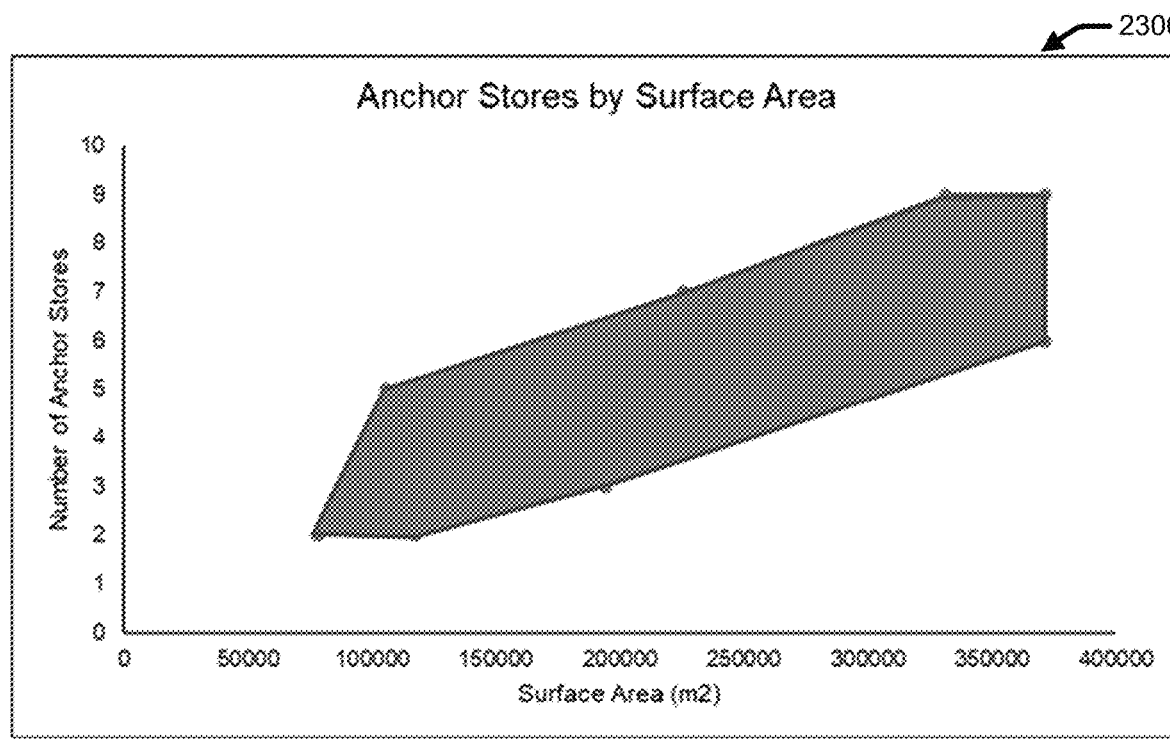
FIG. 23 illustrates Uniform Shape Distribution for the Number of Anchor Stores by Surface Area according to an embodiment.

| Parameter | Description | Distribution | Values |
|---|---|---|---|
| Hallway Width | The ratio of the hallway width to the total width of the building | BetaPERT | Min: 0.03<br>Max: 0.25<br>Mode: 0.1 |
| Residence Time | The time spent on average in a store | Truncated Log Normal | Min: 1.0 hour<br>Max: 4.0 hours<br>Mean: 1.31 hours<br>Stdev: 0.633 hours |
| Store Storage Space | The ratio of storage area to total area | BetaPERT | Min: 0.05<br>Max: 0.5<br>Mode: 0.2 |
| Number of Floors | Number of floors in the building | Discrete Uniform | (number of floors, probability)<br>(1, 0.185)<br>(2, 0.556)<br>(3, 0.185)<br>(4, 0.074) |
| Anchor Stores by Surface Area | The number of anchor stores in the mall based on the total surface area | Uniform Shape Integer | FIG. 23. Uniform Shape Distribution for the Number of Anchor Stores by Surface Area |
| Small Stores by Surface Area | The number of small stores in the mall based on the total surface area | Uniform Shape Integer | FIG. 24. Uniform Shape Distribution for the Number of Small Stores by Surface Area |
| Anchor Proportion by Small Store Proportion | The percentage area of small stores based on the percentage of anchor stores | Uniform Shape | FIG. 25. Uniform Shape Distribution for the Percentage of Anchor and Small Stores in a Mall |
| Population by Surface Area | Arena population per hour as determined by the total surface area | Uniform Shape | FIG. 26. Uniform Shape Distribution for Mall Population |

FIG. 23 illustrates a chart 2300 of Uniform Shape Distribution for the Number of Anchor Stores by Surface Area according to an embodiment.

Figure 24:
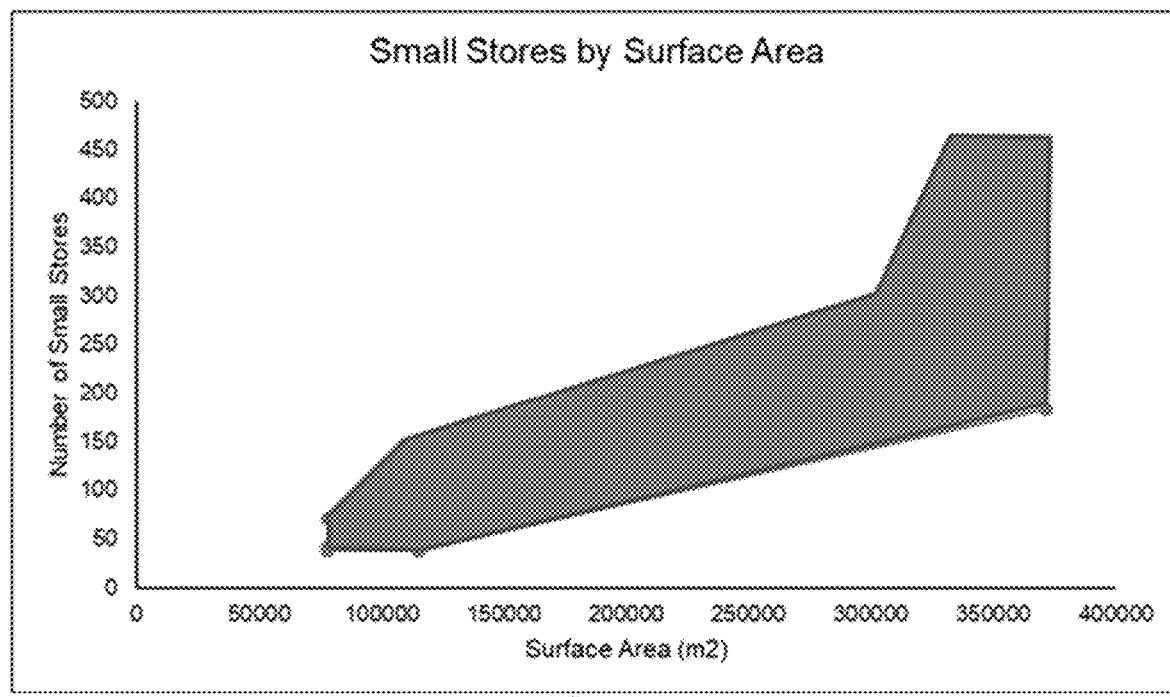
FIG. 24 illustrates Uniform Shape Distribution for the Number of Small Stores by Surface Area according to an embodiment.

FIG. 24 illustrates a chart 2400 of Uniform Shape Distribution for the Number of Small Stores by Surface Area according to an embodiment.

Figure 25:
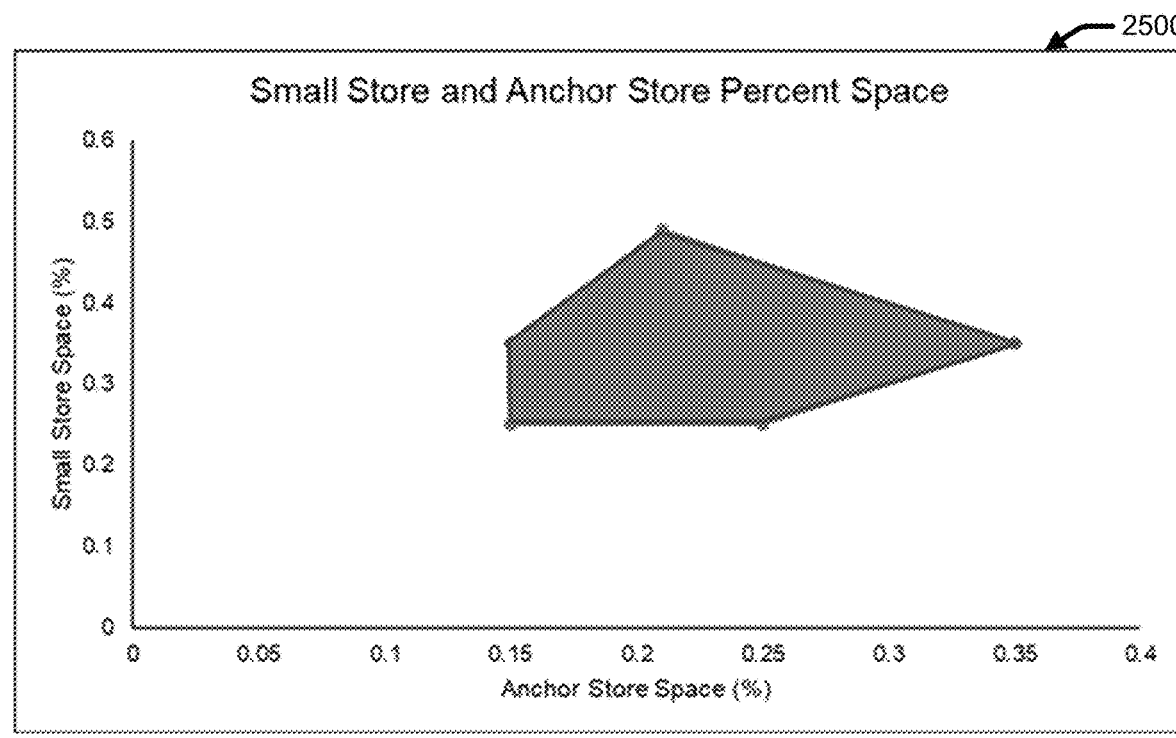
FIG. 25 illustrates Uniform Shape Distribution for the Percentage of Anchor and Small Stores in a Mall according to an embodiment
Figure 26:
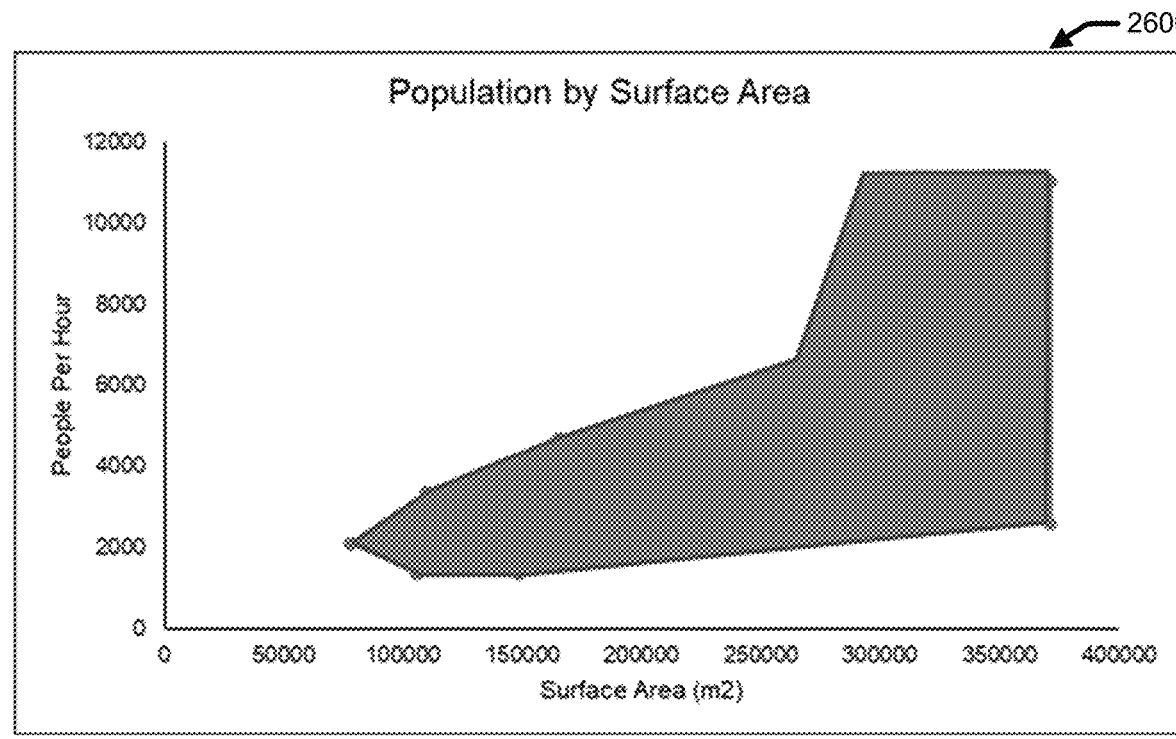
FIG. 26 illustrates Uniform Shape Distribution for Mall Population according to an embodiment.

FIG. 25 illustrates a chart 2500 of Uniform Shape Distribution for the Percentage of Anchor and Small Stores in a Mall according to an embodiment FIG. 26 illustrates a chart 2600 of Uniform Shape Distribution for Mall Population according to an embodiment.

Materials of construction for the Shopping Mall consists of wood, steel, masonry, and concrete. The materials of construction are an average taken from the Hazus designated building types(weight) COM1 (0.5) and COM2(0.5). Table 21 has the material parameter weights listed.

TABLE 21

Shopping Mall Material Distribution

| Material | Weight |
|---|---|
| Wood | 0.1659 |
| Steel | 0.3241 |
| Masonry | 0.2566 |
| Concrete | 0.2533 |

Subway

The IEM models subway stations in two main parts, the platform and surrounding station walls, and the subway trains. The platform may either be an "island" platform, with a subway car on either side, or a "side" platform, with a platform on each side of the building and two subway trains in the middle. Additionally, the platform location can either be "below" ground with indestructible exterior walls preventing venting, or "above" ground and not enclosed. In addition to platform type and location, the subway generator requires platform length, width and height, number of subway cars, and train population. Table 22 has a detailed parameter breakdown.

TABLE 22

Subway Generator Parameters

| Parameter | Description | Distribution | Values |
|---|---|---|---|
| Platform Type | The type of subway platform | Discrete Uniform | Type, Weight<br>(Island, 0.5)<br>(Side, 0.5) |
| Platform Location | Whether or not the platform is located above or below ground | Discrete Uniform | Type, Weight<br>(Above, 0.356)<br>(Below, 0.644) |
| Platform Width | Width of the Subway platform | Uniform | Min: 3.048 m<br>Max: 6.096 m |
| Length | Platform length | Constant | 55.74 m |
| Height | Platform height | Constant | 2.787 m |
| Number of Cars | The number of subway cars | Constant | 10 cars |
| Train Population | The number of people | Uniform | Min: 50 people<br>Max: 20000 people |

Materials of construction for the Subway consists of wood, steel, masonry, and concrete. The materials of construction are an average taken from the Hazus designated building types COM4. Table 23 has the material parameter weights listed.

TABLE 23

Subway Material Distribution

| Material | Weight |
|---|---|
| Wood | 0.3059 |
| Steel | 0.2351 |
| Masonry | 0.2950 |
| Concrete | 0.1638 |

Theater

A theater consists of an empty stage on the side of the building with rows of seating sloping upwards away from the stage. A mezzanine is generated above the ground level seating. The required inputs are, population, surface area, height, stage length, stage depth, and building aspect ratio. A more detailed breakdown is found in Table 24.

TABLE 24

Theater Generator Parameters

Figure 27:
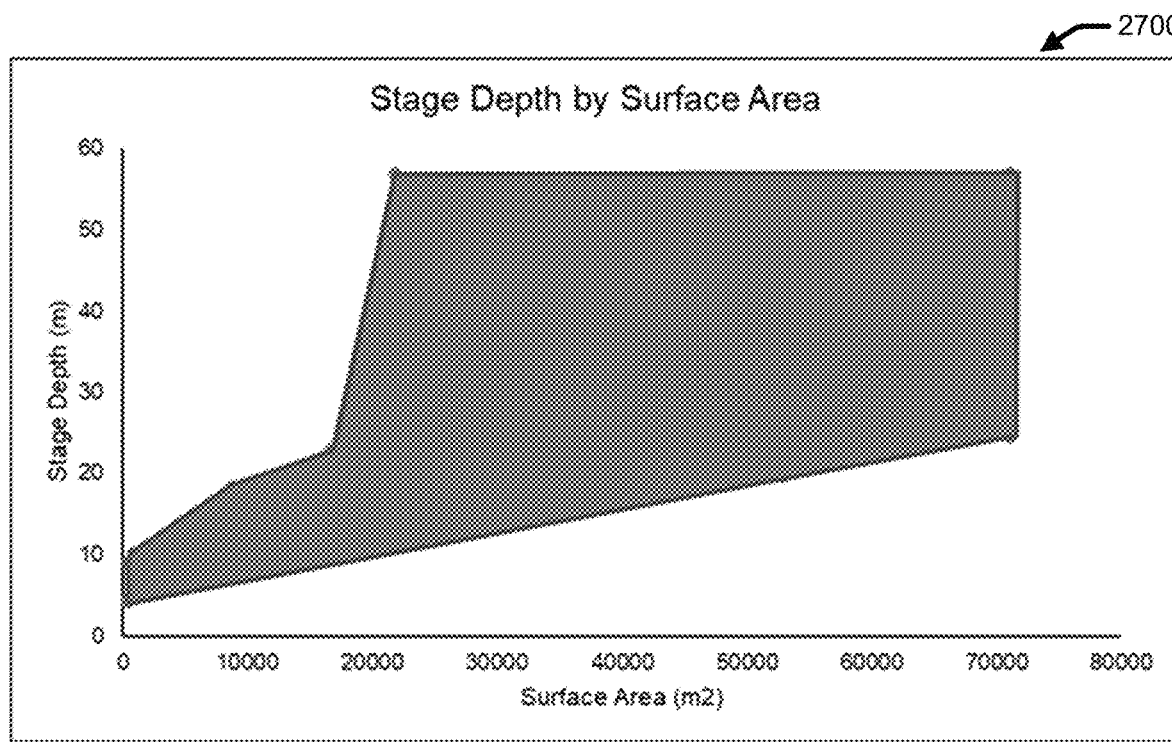
FIG. 27 illustrates Uniform Shape Distribution of Theater Stage Depth according to an embodiment.
Figure 28:
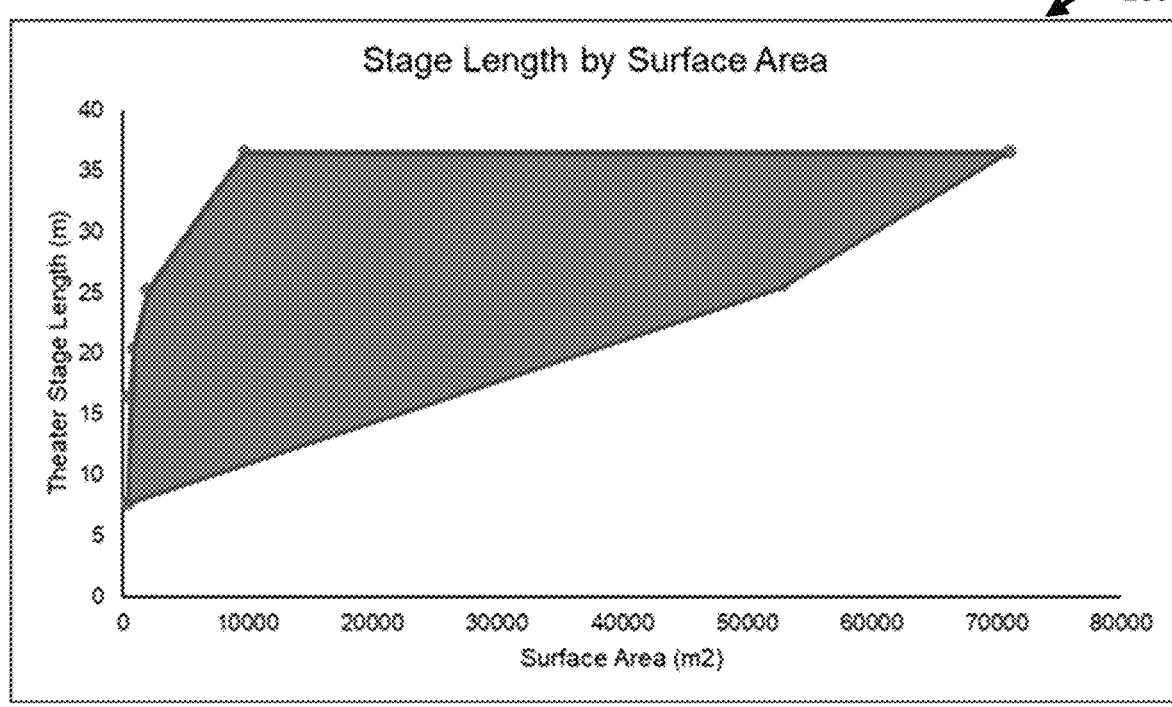
FIG. 28 illustrates Uniform Shape Distribution of Theater Stage Length according to an embodiment.
Figure 29:
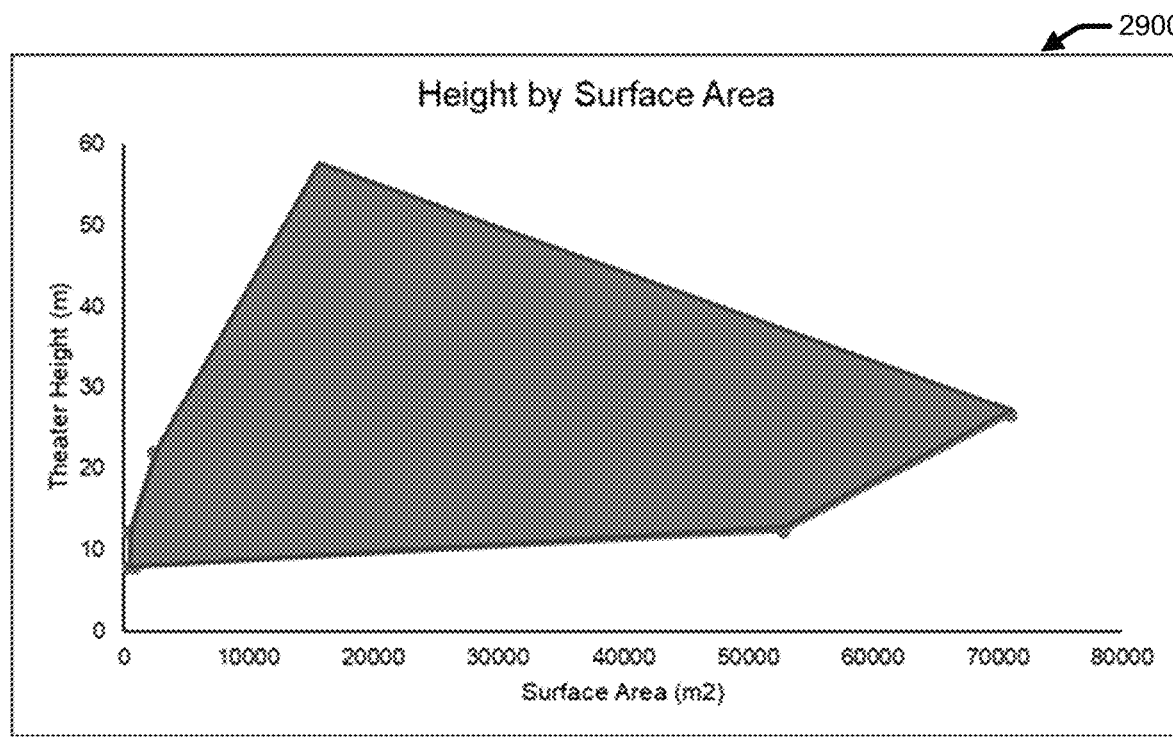
FIG. 29 illustrates Uniform Shape Distribution for Theater Height according to an embodiment.
Figure 30:
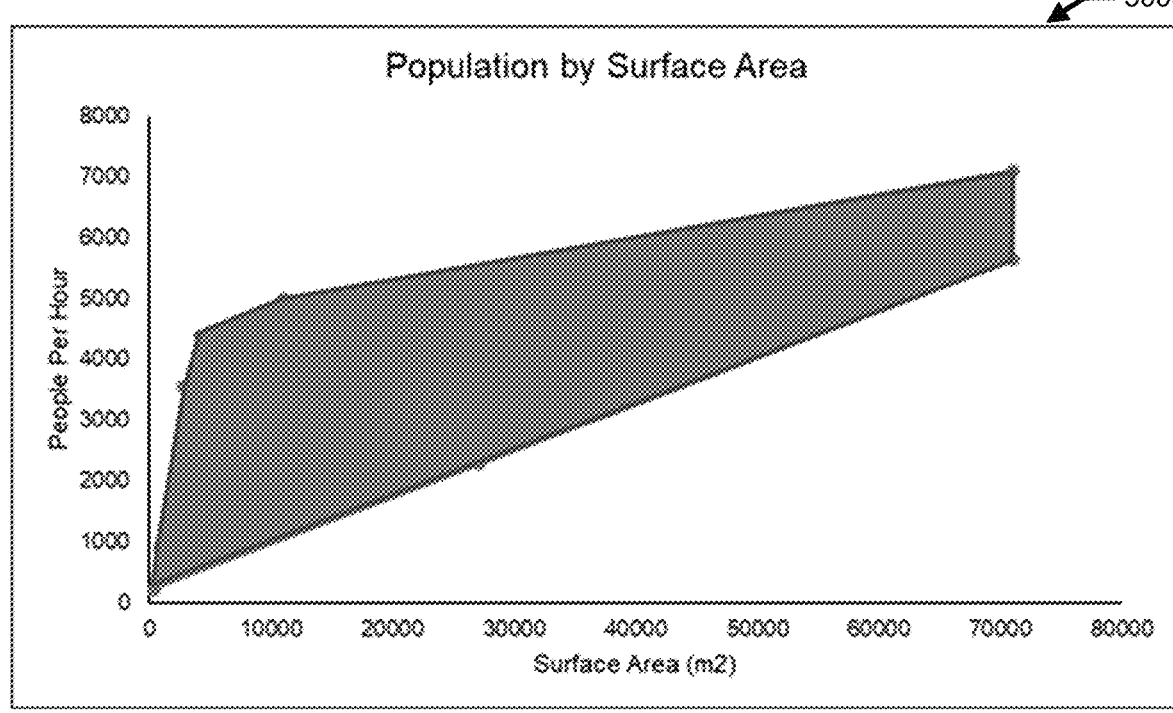
FIG. 30 illustrates Uniform Shape Distribution for Theater Population according to an embodiment.

| Parameter | Description | Distribution | Values |
|---|---|---|---|
| Aspect Ratio | The stage depth | BetaPERT | Min: 1.0<br>Max: 3.0<br>Mode: 1.63 |
| Stage Depth by Surface Area | The depth of the stage based on theater surface area | Uniform Shape | FIG. 27.<br>Uniform Shape Distribution of Theater Stage Depth |
| Stage Length by Surface Area | The length of the stage based on theater surface area | Uniform Shape | FIG. 28.<br>Uniform Shape Distribution of Theater Length |
| Height by Surface Area | Theater height based on surface area | Uniform Shape | FIG. 29.<br>Uniform Shape Distribution for Theater Height |
| Population by Surface Area | Theater population per hour based on surface area | Uniform Shape | FIG. 30.<br>Uniform Shape Distribution for Theater Population |

FIG. 27 illustrates a chart 2700 of Uniform Shape Distribution of Theater Stage Depth according to an embodiment.

FIG. 28 illustrates a chart 2800 of Uniform Shape Distribution of Theater Stage Length according to an embodiment.

FIG. 29 illustrates a chart 2900 of Uniform Shape Distribution for Theater Height according to an embodiment.

FIG. 30 illustrates a chart 3000 of Uniform Shape Distribution for Theater Population according to an embodiment.

Materials of construction for the Theater consists of wood, steel, masonry, and concrete. The materials of construction are an average taken from the Hazus designated building types COM9. Table 25 has the material parameter weights listed.

TABLE 25

Theater Material Distribution

| Material | Weight |
|---|---|
| Wood | 0.0389 |
| Steel | 0.4891 |
| Masonry | 0.2132 |
| Concrete | 0.2586 |

Device Location

In each realization the device location is determined based on a required user selected input. The specific location is identified as a fractional location in building units.

Outdoor Scenario Generation

The scenario inputs include the latitude and longitude of the explosive device, and a radius of attack within which the explosive can be placed anywhere. This differs slightly from the Interior Model, which just requires dimensions and type for the single building that is targeted. The scenario parameters and descriptions are in Table 26.

TABLE 26

Scenario Parameters

| Input | Description |
|---|---|
| Target Location | The city that the device is detonated in |
| | The target latitude and longitude |
| Radius | The radius around the target latitude and longitude within which the device can be placed. If the location is not specified, a location within the radius will be randomly selected |

Because the Explosives Exterior Model (EEM) modeled the damage and injuries in larger spaces potentially encompassing multiple buildings, it is necessary to characterize the surrounding buildings and population from the release point. This is done through the use of Cityscape Generation, which identifies some of the important parameters when modeling a larger scale scenario, and characterizes the type and occupancy of surrounding buildings, using various datasets including the HSIP population dataset, the GRiD database, and HAZUS census block level information.

Cityscape Generation is divided into two categories: Fully Defined and Partially Defined. Fully Defined areas possessed sufficient data to create definitive shapefiles that describe the precise location and dimensions of buildings (e.g., areas characterized by GRiD based on lidar data). Partially Defined areas only possessed sufficient data to create probabilistic shapefiles that describe the approximate location and dimensions of buildings (e.g., areas characterized by census block data from HAZUS). For Partially Defined areas each consequence simulation will generate a realization of potential buildings (e.g., different building footprints and heights to match a total square footage).

For both Fully Defined and Partially Defined cityscapes, HAZUS data is used in a probabilistic fashion to assign the type of building at a census block level and estimate the building construction. Each consequence simulation in the Exterior Model generates a realization of potential building types and construction (e.g., masonry religious building, wood commercial building or reinforced concrete industrial building). Once more information about the blast is ascertained, the cityscape can be generated and used in further calculations.

Since the Explosives Exterior Model (EEM) models the damage and injuries in larger spaces potentially encompassing multiple buildings, it is necessary to characterize the surrounding buildings and population from the release point. This is done through the use of Cityscape Generation, which identifies some of the important parameters when modeling a larger scale scenario, and characterizes the type and occupancy of surrounding buildings, using various datasets including the Homeland Infrastructure Foundation-Level Data (HIFLD) population dataset, the National Geospatial Agency's Geospatial Repository and Data Management System (GRiD) database, and HAZUS census block level information.

Defined buildings are those which are included in the (GRiD) database and can be queried based on census blocks. If heights are not available for these buildings, then randomized heights are generated based on the total surface areas in the block.

For some locations, there are no defined buildings. In these areas, buildings are generated probabilistically by dividing the census block into parcels based on the ratios of surface area for each building type. The buildings are then placed in the center of each parcel, and the number of floors is sampled from a correlation distribution generated from fully defined areas.

Once all the buildings in the simulation have been defined, building types are assigned based on the total surface area and building count within their census block. The assigned building type determines the materials used for its construction, based on the given region provided by HAZUS. Based on the assigned building type, an appropriate interior building layout is generated for each building.

Device Generation

Once the scenario/target has been defined/parameterized, the next step is to define the hazard for subsequent calculations. This consists of two parts—defining the explosive device used for the event and initializing the main physical phenomena that drive injuries and damage. The explosive device has several main parameters, as well as additional, optional enhancements including casing, fragments, and thermal enhancements.

The order of initialization and hazard propagation is as follows: 1) shockwave initialization, 2) combustion gas initialization, and finally 3) debris initialization. Shockwaves are the result of the area of pressure expanding outward (supersonically) from the explosive core, and thus are the first phenomenon to be considered. Combustion also occurs at a very rapid rate but not at the supersonic rate that shockwaves occur and thus trail the shockwave. Finally, the debris propagation is dependent on the forces and energy generated from combustion and the shockwave and is the last phenomenon to be initialized.

The device and phenomena initialization are described and parameterized in the following sections.

Device Characteristics

An explosive device is specified by the mass of explosive materials it contains, the fuel and material combination, the location within the building where it is placed, and the mass and type of thermal, casing, or fragmentation enhancements added to it. The device parameters are listed in, along with brief descriptions. Explosive devices are generated using probability distributions of the parameters mentioned, which are also listed in the table below, and detailed in corresponding sections.

TABLE 27

Device Inputs

| Parameter | Description | Distribution Type |
|---|---|---|
| Mass | The mass of the explosive material in the scenario. | Uniform |
| Location | The location within the building that the device is placed. Has x, y, z component corresponding to grid and floor placement | Discrete |
| Explosive Material | The Explosive material used in the explosive device. | N/A |
| Fuel (Optional) | The fuel used in the device. This is only valid for certain explosive materials. | N/A |
| Casing Enhancement | Any enhancements used to case the device (e.g., PCV cylinders) | See 0 |
| Fragmentation Enhancement | Fragments that may be included within the device to increase damage (e.g., nails) | See 0 |
| Thermal Enhancement | Materials that alter the device by increasing the total amount of energy available for release at detonation | See 0 |

The explosive materials are fully detailed by their chemical and applied properties including the heat of formation and TNT equivalence. This procedure allows the HExCAT the flexibility of considering pure materials, e.g., RDX, as well as combinations of materials, e.g., Ammonium Nitrate (AN) with Nitromethane. Any combination of optional thermal, casing, or fragmentation enhancements can also be added to the device.

Explosive Material

Twenty-six explosive materials, shown in Table 28, are included in initial HExCAT library.

TABLE 28

Explosive Materials Used
Explosive Materials

Ammonium Nitrate 250 um
Ammonium Nitrate EG Prill
Ammonium Nitrate FG Prill
Black Powder
Dynamite
Erythritol Tetranitrate (ETN)
Ethylene Glycol Dinitrate (EGDN)
HMTD
Hydrogen Peroxide
Nitric Acid
Nitrocellulose Low Density
Nitrocellulose Mid Density
Nitrocellulose High Density
Nitroglycerin
Nitromethane-sensitized
Pentaerythritol tetranitrate (PETN)
Picric Acid
Potassium Chlorate
Potassium Perchlorate
Potassium Permanganate
RDX (as C-4)
Sodium Chlorate
Tetryl (2,4,6 tetranitro-N-methylaniline)
Triacetonetriperoxide (TATP)
Urea Nitrate
Pentolite Explosive materials were parameterized with a series of metrics, tabulated below in Table 29.

TABLE 29

Material Inputs

| Parameter | Description | Distribution Type |
|---|---|---|
| Molecular Formula | The molecular formula of the material, given in number of different elements (e.g., 6 carbons, 4 hydrogens). | Discrete |
| Theoretical Density | The density of the material ($kg/m^3$). | Constant |
| State | The state of the material (solid, liquid, gas) | N/A |
| Fuel Selection (Optional) | The fuel used in the device. This is only valid for certain explosive materials. | N/A |
| Gurney Velocity | The Gurney Velocity, used for fragmentation calculations (m/s). | Constant |
| Heat Of Formation | The amount of heat absorbed or evolved when one mole of the material is formed from its constituent elements | Constant |

TABLE 29-continued

Material Inputs

| Parameter | Description | Distribution Type |
| --- | --- | --- |
| TNT Equivalence | Measure for the energy released in the explosion (unitless). | Constant |

Some of the oxidizers in Table 29 need a fuel to form an explosive. The same parameters are tabulated for fuels as the explosive materials. A list of fuels is shown in below, in Table 30. While a discrete number of materials have been included in the initial HEXCAT library, there is an option to expand the library with user defined materials.

TABLE 30

List of Fuels
Fuels Incorporated

Diesel
Nitromethane
Nitrobenzene
Aluminum Swarf Small
Aluminum 63u
Aluminum Flake or Powder
Aluminum Paint Grade
Aluminum Powder or Dust
Aluminum 44u
Water
Acetone
Tang
Black Pepper
Cumin
Flour
Ethanol
Methyl Ethyl Ketone
Lampblack
Paraffin
Sulfur
Icing sugar
Aluminum
Nitrobenzene
Wood Meal
Kerosene
Vaseline
Naptha
Magnesium
Sugar
TNT

Casing Enhancement

Casing enhancements are specified by the geometric dimensions and material density of the casing. They cover a wide range of materials used to contain and deliver improvised explosive devices. Devices range from PVC cylinders as utilized by the typical pipe bombs to steel spheres approximating the full enclosure of pressure cookers.

The casing parameters are tabulated below, along with the default ranges used for each parameter:

TABLE 31

List of Casing Parameters

| Parameter | Description | Distribution Type | Range |
| --- | --- | --- | --- |
| Shape | The shape of the casing enhancement. | N/A | Planar, Cylindrical, Spherical |

TABLE 31-continued

List of Casing Parameters

| Parameter | Description | Distribution Type | Range |
| --- | --- | --- | --- |
| Width to Height Ratio | Geometric Dimensions, only valid for planar casing. | Uniform | 0.1-10 |
| Depth to Height Ratio | Geometric Dimensions, only valid for planar casing. | Uniform | 0.1-10 |
| Radius to Height Ratio | Geometric Dimensions, only valid for cylindrical casing. | Uniform | 0.1-10 |
| Percent Volume Void | Percent of empty space in the container holding the explosive material. | Uniform | 0.01-0.1 |
| Thickness | The thickness of the casing (m). | Uniform | Planar, Spherical: 0.002-0.007 Cylindrical: 0.001-0.1 |
| Material | The material used for the device casing. | N/A | Steel, Aluminum, Tungsten, Copper |

Fragmentation Enhancement

Fragmentation enhancements are specified through the density, mass, and aspect ratio of added fragments. These properties are chosen to best approximate the relevant physical properties for a range of commonly used fragmentation enhancements, such as nails or ball bearings. Both casing and fragmentation enhancements are propagated by the mechanisms for general debris propagation, discussed below. The parameters are listed in Table 32.

TABLE 32

List of Fragmentation Parameters

| Parameter | Description | Distribution Type | Range |
| --- | --- | --- | --- |
| Fragmentation Enhancement Type | The type of fragmentation added to the device. | N/A | Nails, Ball Bearing |
| Mass | The total mass of fragmentation. | Uniform | 9.07-27.21 kg |
| Single Fragment Volume | Volume of a single fragment (e.g., a single nail, one ball bearing) | Nails: Truncated Uniform | Nails: Min: 0.2E-6 kg Max: 1.878E-6 kg Mean: 0.6E-6 Standard Deviation: 1E-6 |
| | | Ball Bearings: Uniform | Ball Bearings: 0.2E-6-1.878E-6 kg |
| Aspect Ratio | | Uniform | Nails: 2.5-8 |
| | | Constant | Ball Bearings: 1 |
| Material | The material of the fragment | N/A | Steel, Aluminum, Tungsten, Copper |

Thermal Enhancements

Thermal enhancements are specified by the chemical properties—formulae, heats of formation, and overall mass—of any added materials, and alter the device by increasing the total amount of energy available for release at detonation. Common examples of thermal enhancement for an explosive device include fuels, such as propane or gasoline, or fuel powders, such as aluminum powder. The initial library for HExCAT includes gasoline and aluminum powder.

Thermal enhancements are parameterized by the same material metrics:
The molecular formula of the material
The density of the material (kg/m³)
The state of the material (solid, liquid, gas)
Gurney Velocity
Heat Of Formation
TNT Equivalence Shockwave Initialization Hot air and gases from device detonation create an air blast that expands at high speed. This shockwave phenomenon travelling through air at supersonic speeds is assumed to be the earliest driver of hazard propagation due to an explosion. The model currently does not account for incendiary effects and assumes that the release of extremely flammable material (magnesium, white phosphorus, gelled fuel mixes, etc.) is negligible. Approximately one third of the chemical potential energy available in most high explosives is released immediately in the detonation process through the shockwave mechanism. The remaining two thirds of potential energy available is released gradually as the detonation products mix with air and burn. This is assumed to have little effect on the initial blast wave due to the dramatic difference in timescales.

Conventionally, shockwave phenomena are well characterized by the complex Kingery-Bulmash equations and empirically compiled from a high-mass TNT air blast data set. For computational efficiency, the IEM implements Swisdack's simplified Kingery equation set. Swisdack et al. approximated the Kingery-Bulmash curves to a high-order polynomial form that was accurate to within one percent of the original equations. The Swisdack equation also incorporated data from a subsequent Kingery-Pannill study which extended the incident pressure curves to lower levels.

The general form of the equation used to describe shockwave time of arrival, incident pressure, incident impulse, reflected impulse, and positive phase duration is of the form $$F(Z)=\mathrm{Exp}(A+B\cdot\ln(Z)+C\cdot\ln^2(Z)+D\cdot\ln^3(Z)+E\cdot\ln^4(Z)+F\cdot\ln^5(Z)+G\cdot\ln^6(Z))$$

Equation 1: Shockwave Formulation

Where:
Parameters A through G are derived by Swisdack's curve fits to the Kingery data,
Parameter Z is the mass-scaled range, the distance from the explosive device divided by the cube root mass of the explosive material.
Function F(Z) is a placeholder for the corresponding quantity, as presented in Table 33.

Table 33 through Table 37 provide fit parameters for each of the aforementioned quantities broken up piecewise for the appropriate Z ranges.

TABLE 33

Time of Arrival (minutes)

| Z | A | B | C | D | E | F | G |
|---|---|---|---|---|---|---|---|
| 1.5-40 | −0.7604 | 1.8058 | 0.1257 | −0.0437 | −0.031 | −0.00669 | 0 |
| 40+ | −0.7137 | 1.5732 | 0.5561 | −0.4213 | 0.1054 | −0.00929 | 0 |

TABLE 34

Incident Pressure (Pa)

| Z | A | B | C | D | E | F | G |
|---|---|---|---|---|---|---|---|
| 2.9-23.8 | 7.2106 | −2.1069 | −0.3229 | 0.1117 | 0.068+ | 0 | 0 |
| 23.8-198.5 | 7.5938 | −3.0523 | 0.40977 | 0.0261 | −0.0126 | 0 | 0 |
| 198.5+ | 6.0536 | −1.4066 | 0 | 0 | 0 | 0 | 0 |

TABLE 35

Incident Impulse (Pa * N)

| Z | A | B | C | D | E | F | G |
|---|---|---|---|---|---|---|---|
| 0.96-2.38 | 5.522 | 1.117 | 0.6 | −0.292 | −0.087 | 0 | 0 |
| 2.38-33.7 | 5.465 | −0.308 | −1.464 | 1.362 | −0.432 | 0 | 0 |
| 33.7-158.7 | 5.2749 | −0.4677 | −0.2499 | 0.0588 | −0.00554 | 0 | 0 |
| 158.7+ | 5.9825 | −1.062 | 0 | 0 | 0 | 0 | 0 |

TABLE 36

Reflected Impulse (Pa * N)

| Z | A | B | C | D | E | F | G |
|---|---|---|---|---|---|---|---|
| 40+ | 6.7853 | −1.3466 | 0.101 | −0.01123 | 0 | 0 | 0 |

TABLE 37

Positive Phase Duration (minutes)

| Z | A | B | C | D | E | F | G |
|---|---|---|---|---|---|---|---|
| 1.02-2.8 | 0.5426 | 3.2299 | −1.5931 | −5.9667 | −4.0815 | −0.9149 | 0 |
| 2.8-40 | 0.544 | 2.7082 | −9.7354 | 14.3425 | −9.7791 | 2.8535 | 0 |
| 40+ | −2.4608 | 7.1639 | −5.6215 | 2.2711 | −0.44994 | 0.0348 | 0 |

A dynamic pressure approach was used to calculate peak pressure reflected from a rigid surface, as described by $$R(P_i) = \frac{2P_i(4P_i + 7P_{STP})}{P_i + 7P_{STP}} \quad \text{Equation 2}$$

Where:
R is the reflected pressure.
$P_i$ is the incident pressure.
$P_{STP}$ is the standard pressure at 20 C at sea level.

Combustion Gas Initialization

Thermal Hazards are determined through a two-stage process with information from BlastX. The burning stage first calculates a series of prioritized combustion reactions based on the composition and heat of formation of the device materials.

The IEM burn model considers combustion reactions in the following order:

$4AL(s)+3O_2(g) \rightarrow 2Al_2O_3(s);$  Equation 3: Aluminum reacts with oxygen to form aluminum oxide $H_2(g)+Cl_2(g) \rightarrow 2HCl(g);$  Equation 4: Hydrogen gas reacts with chlorine gas to form gaseous hydrogen chlorine $2C(s)+O_2(g) \rightarrow 2CO(g);$  Equation 5: Carbon reacts with oxygen gas to form carbon monoxide $\{0.48X\}CO+F_2 \rightarrow CF_2O;$  Equation 6: Fluorine reacts with 48 percent of the carbon monoxide present to form carbonyl fluoride $2C+H_2+3F_2 \rightarrow 2CHF_3;$  Equation 7:) Leftover fluorine reacts with carbon and hydrogen gas to form fluoroform gas $H_2+F_2 \rightarrow 2HF;$  Equation 8: Excess fluorine reacts with hydrogen gas to form hydrogen fluoride $2H_2+\{0.95X\}O_2 \rightarrow 2H_2O$  Equation 9: Hydrogen reacts with 95 percent of the remaining oxygen to form water $2CO+\{0.65X\}O_2 \rightarrow 2CO_2$  Equation 10: 65 percent of the remaining oxygen reacts with carbon monoxide to form carbon dioxide If the materials necessary for a reaction to occur are not present, the reaction is skipped. As additional materials are introduced to the reaction—e.g., venting into a room with additional oxygen present—the reaction continues. Once all the reactions are simulated, the released energy is calculated and used to determine the pressure and temperature within the grid containing the explosive device.

Debris Initialization

Debris hazards are generated through a variety of sources. Debris fragments are defined by different physical properties and obtain initial velocities based on the mechanism through which they are generated. Once debris is generated, it is subject to the same physics regardless of source for the remainder of its lifespan. The equations for debris propagation are based on standard approaches in the literature.

Detonation of an explosive device with a casing results in the generation of debris due to casing fragmentation. The fragment sizes are distributed according to Mott's distribution and have an initial velocity derived from the explosive device properties using Equation 11. Material density is assumed to be the density of the specified casing.

$$v_i = \frac{G}{\sqrt{\frac{m_{casing}}{m_{explosive}} + \frac{s}{s+2}}} \quad \text{Equation 11}$$

Initial Velocity Derviation

Where:
$v_i$ is the initial velocity.
$m_{casing}$ is the mass of the device casing.
$m_{explosive}$ is the mass of the explosive material.
G is the Gurney characteristic velocity of the explosive material.
s is a shape factor representing the geometry of the device, where:
For a planar geometry, s=1;
For a cylindrical geometry, s=2;
For a spherical geometry, s=3.

Debris can also be generated through enhancements to the explosive device. Fragmentation enhancements are defined by a material density and user-input distributions for individual fragment mass, total fragment mass, and fragment aspect ratio. These fragments are accelerated by the air blast, and their initial velocities are determined by application of the impulse-momentum theorem as:

$$v_i = \frac{I}{m_{fragment} \cdot a_{exposed}} \quad \text{Equation 12}$$

Initial Velocity Determination

Where:
$v_i$ is the initial velocity.
$m_{fragment}$ is the mass of the fragment.
I is the initial impulse applied to the fragment.
$a_{exposed}$ is the surface area of the fragment exposed to the driving pressure wave.

The final mechanism for debris generation is through barrier destruction. When a barrier is destroyed by an applied pressure wave, the remaining incident energy after the minimal energy for component failure is used to determine the fragment mass distribution. Like the casing fragmentation, the barrier fragment masses are well described by an application of Mott's distribution. Acceleration for barrier fragments is also determined by the impulse-momentum theorem in the equation below:

$a_{fragment} = m_{fragment}/F$  Equation 13: Acceleration Determination

Where:
F is the average net force.
m is the mass of the fragment.
$v_i$ is the initial velocity.

As debris travels through air, it loses velocity due to drag. Since the coefficient of drag varies with the geometry and speed of a projectile, it is calculated dynamically as the debris propagates. At each instant during propagation, the Reynolds number—the ratio of inertial to viscous forces within a fluid, as in Equation 14—is calculated for each fragment. This Reynolds number is used as input into an empirical correlation to determine the coefficient of drag for the fragment. With the coefficient of drag, the decay constant and then velocity decay are computed.

Decay Constant and Velocity Calculation          Equation 14

$$Re = \frac{\rho u L}{\mu}$$

$$C_d = \frac{24}{Re} + \frac{2.6\left(\frac{Re}{5.0}\right)}{1+\left(\frac{Re}{5.0}\right)^{1.52}} + \frac{0.411\left(\frac{Re}{2.63\cdot 10^5}\right)^{-7.94}}{1+\left(\frac{Re}{2.63\cdot 10^5}\right)^{-8.0}} + \frac{2.5\left(\frac{Re}{10^6}\right)}{1+\left(\frac{Re}{10^6}\right)}$$

$$k_v = \frac{\sigma}{m_f}\rho \cdot C_d$$

$$v_f = v_i \cdot e^{-12 \cdot k_v \cdot d}$$

Where:

Re is the Reynolds number of the fragment in fluid.

ρ is the density of fluid—for air, 1.2754 kg/m³.

μ is the dynamic viscosity of fluid—for air, 18.6 μPa·s.

u is the flow rate (velocity relative to medium, taken as the velocity) in m/s.

L is the characteristic linear dimension, taken as diameter (in) for a sphere.

$C_d$ is the coefficient of drag of a fragment at specified velocity.

$m_f$ is the mass of the fragment.

σ is the cross-sectional surface area of the fragment.

$k_v$ is the decay constant of a particular fragment at a specified velocity.

$v_i$ is the initial velocity of a fragment before application of drag forces.

$v_f$ is the final velocity of a fragment after application of drag forces.

d is the distance traveled by a fragment.

It is necessary to account for the increased resistance a fragment would encounter when it contacts a human body. Since the IEM calculates injuries following hazard propagation, this condition could not be imposed discretely. Instead, it was necessary to modify debris travel velocity statistically based on the population per grid. It is assumed that the density and dynamic viscosity of the human body were approximated by those of water, and that the volume of the average human was approximated as 70 L. The velocity decay is then calculated using an average density and dynamic viscosity weighted by the fraction of the grid volume that is human biomass.

Hazard Propagation

The hazard propagation methodology is determined by the initial user selection of interior or exterior placement of an explosive device.

Figure 31:
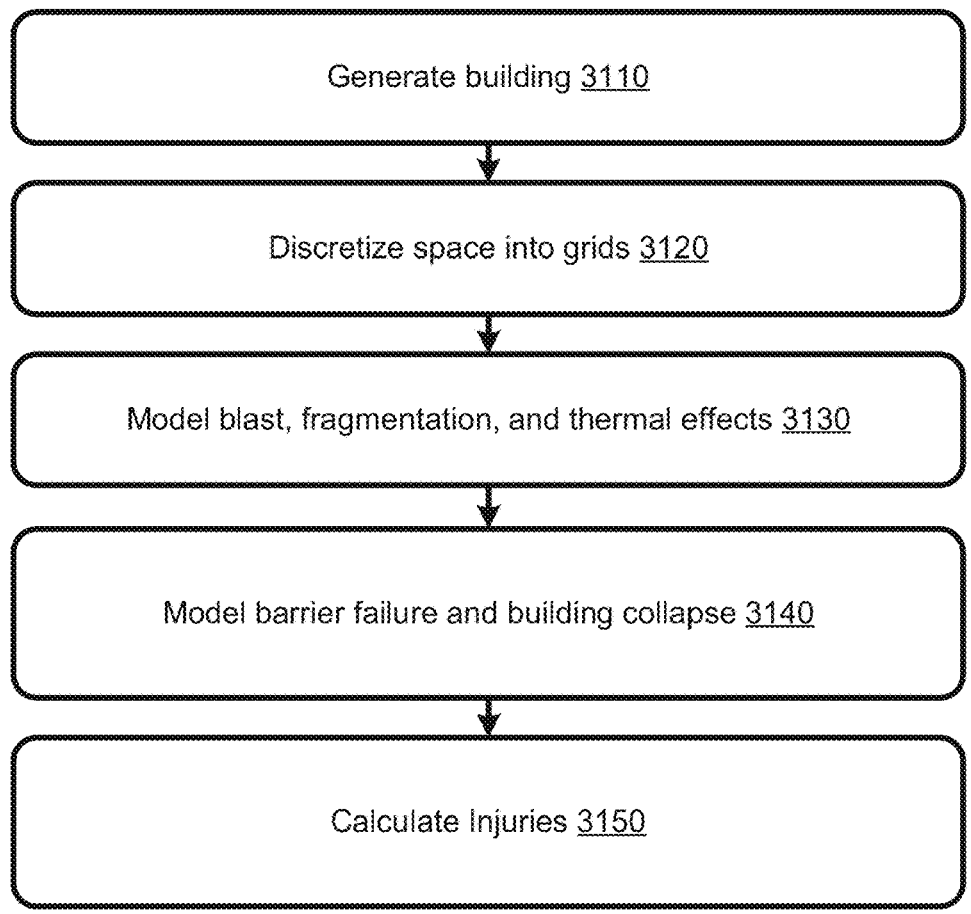
FIG. 31 illustrates a flowchart to calculate indoor injuries according to an embodiment.

FIG. 31 illustrates a flowchart 3100 to calculate indoor injuries according to an embodiment. Calculating injuries in this embodiment is based on an explosive device placed inside a building. The building is generated based on target type, which is further defined based on parameters associated with compartmentalized or open buildings and drawn from distributions for such things as materials of construction, surface area, number of floors, aspect ratios, population at 3110, at which the computer system generates buildings. For example, the computer system accesses a database of building information and census information to randomly generate a building of an average size for that location. The building is discretized into a three-dimensional grid at 3120, at which the computer system discretizes spaces into grids. For example, each building is modeled as a plurality of grids including barriers and supports that can be damaged by an explosive device. Hazards are propagated based on the priority order of hazards at 3130 and 3140. At 3130, the computer system models blast, fragmentation, and thermal effects. For example, the computer system executes models to address multiple different effects on the grids of the building caused by detonation of the explosive device. At 3140, the computer system models barrier failure and building collapse. For example, the computer system determines whether detonation of the explosive device damages the grid of barriers and supports to determine the extent of barrier failure or support failure resulting in building collapse. The physical phenomena calculated from the blast are used to calculate life threatening and sub-lethal injuries using standard probit expressions at 3150, at which the computer system calculates injuries. For example, the computer system propagates the hazards (blast, fragmentation, and thermal effects) through the building and determines how those hazards cause injuries to a population distribution in the building, whether directly (e.g., burns) or indirectly (injured from building collapse).

Figure 32:
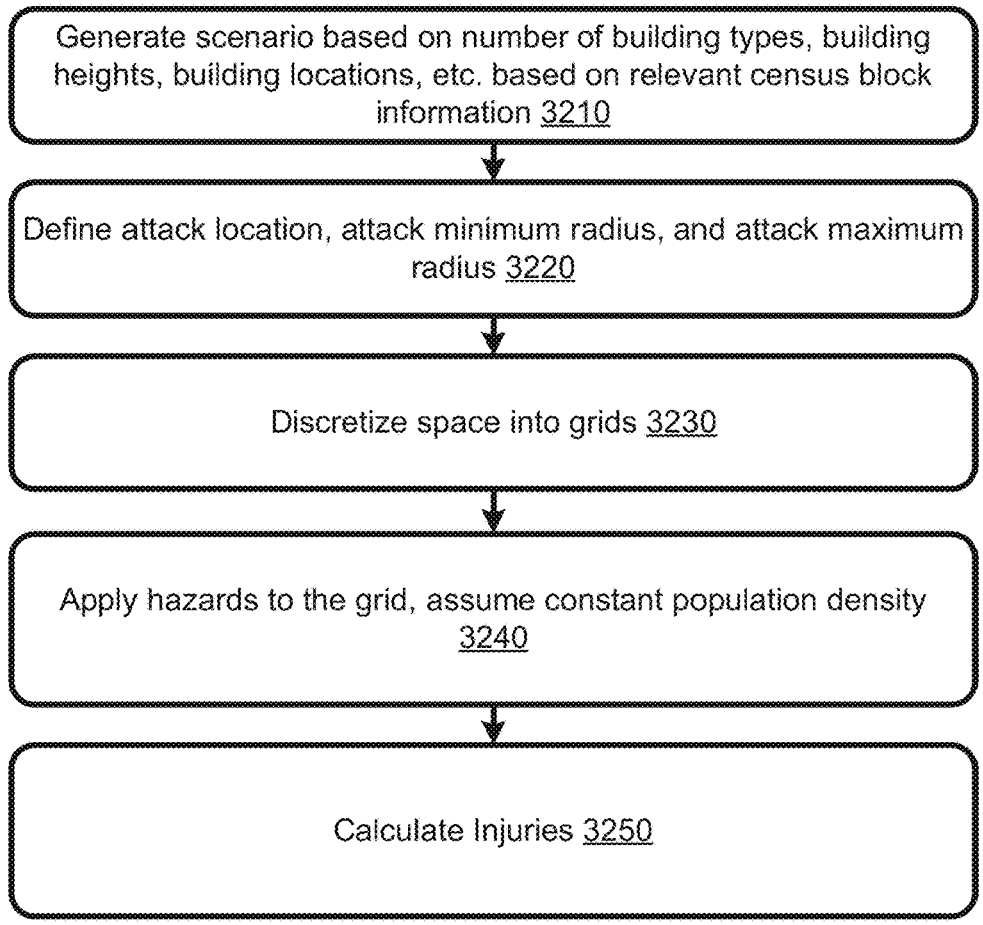
FIG. 32 illustrates a flowchart to calculate outdoor injuries according to an embodiment.

FIG. 32 illustrates a flowchart 3200 to calculate outdoor injuries according to an embodiment. At 3210, the computer system generates a scenario based on number of building types, building heights, building locations, etc. based on relevant census block information. For example, the computer system generates an entire outdoor cityscape of buildings corresponding to the general area using the census block information, without needing specific information about any particular building dimensions. At 3220, the computing system defines an attack location, attack minimum radius, and attack maximum radius. For example, the computer system prompts the user for such specific information, and if not provided, the computer system uses default values (e.g., located in a city center, with an attack minimum radius of one city block and maximum radius of ten city blocks). In an embodiment, the computing system collects security plan inputs. For example, the user inputs include details about security checkpoint locations and whether people passing through the security checkpoint are allowed to carry bags of a certain size. Such information allows the computing system to place additional constraints on parameter spaces, e.g., by constraining potential explosive device locations (cannot pass beyond the security checkpoint location) or sizes (cannot fit in bags of a certain size or smaller subject to the security checkpoint constraints). At 3230, the computer system discretizes the space of the scenario into grids. For example, the grid is based on isopleths corresponding to distance from the attack location. At 3240, the computer system applies hazards to the grid, assuming constant population density. For example, the computer system consults a table of population density for a given outdoor space, and uses that population density overlaid on the grid. At 3250, the computer system calculates injuries. For example, the computer system calculates a number of victims located in a given grid cell based on the population density overlaid on that given grid cell.

Interior Shockwave Propagation

The methodology for shockwave propagation is based on standard methodologies. Starting at the location of the explosive device, an air blast, or shockwave, expands linearly into all adjacent grids, illustrated in FIG. 33. When no barriers are in the path of the shockwave, the linear expansion of the shockwave continues unobstructed. The incident pressure and impulse are calculated using the distance from the shockwave source.

FIG. 33 illustrates Initial Blast Expansion 3300 according to an embodiment. Each accessible grid was "visited" by the shockwave a maximum of once. Grids are visited in order of increasing distance from the shockwave source. Grid propagation is illustrated below, in FIG. 34. FIG. 34 illustrates Shockwave Propagation Population 3400 according to an embodiment.

This algorithm effectively calculates the pressure and impulse as generated by a spherically symmetric shockwave originating at a point source, illustrated in FIG. 35. In the corner grids, the parameters are calculated using the diagonal linear distance from the blast. However, if there are barriers, then the value is calculated assuming diffraction around the barrier. FIG. 35 illustrates Spherical Shockwave 3500 according to an embodiment.

The shockwave is reflected by barriers in its path. Effects of first order reflections are tracked in the grid adjacent to the reflection but are not propagated recursively. Though this simplifies calculations, this may artificially reduce the effects of the shockwave.

Figure 36:
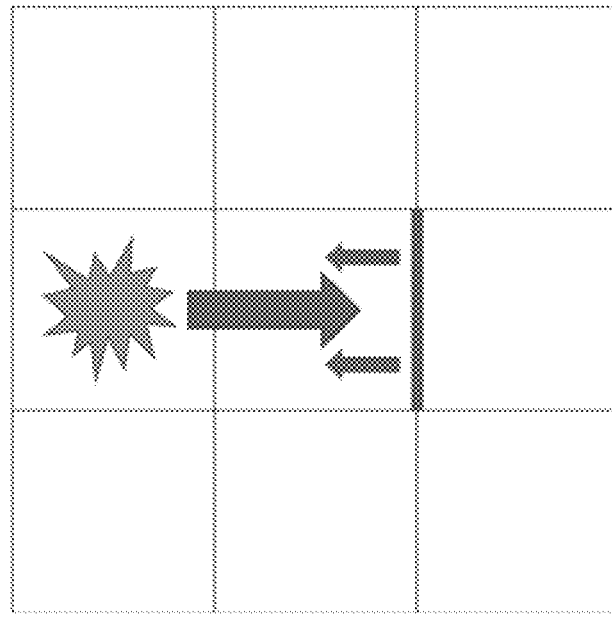
FIG. 36 illustrates No Barrier Failure according to an embodiment.

The reflected pressure and impulse are applied to the encountered barrier. If the materials comprising the barrier do not fail, the shockwave does not continue, displayed in FIG. 36. FIG. 36 illustrates No Barrier Failure 3600 according to an embodiment.

Figure 37:
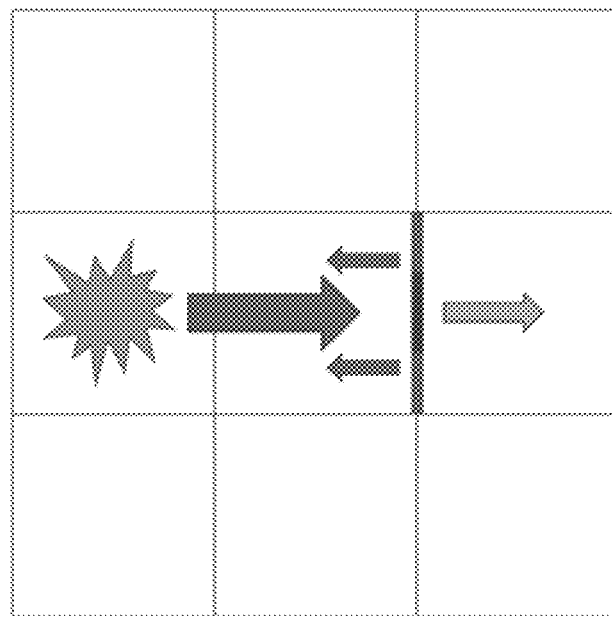
FIG. 37 illustrates Barrier Failure according to an embodiment.

If one or more of the materials that comprise the barrier fail, the shockwave may diffract through the created aperture, displayed in FIG. 37. FIG. 37 illustrates Barrier Failure 3700 according to an embodiment.

The diffracted shockwave is treated as a spherically symmetric wave originating at the point of diffraction and propagates identically to the first-order shockwave. The shockwave propagation algorithm continues recursively until no new diffractions exist or until a selected diffraction recursion-depth is exceeded.

The shockwave propagation model outputs the maximum pressure, impulse, and barrier failure level for each impacted grid. Isopleths are captured at the appropriate pressure and impulse thresholds for use in the injury model.

Interior Combustion Gas Propagation

After being initialized, combustion gases are vented throughout the building. The propagation stage then estimates decreases in quasi-static gas pressure and temperature due to venting and expansion using the ideal gas law. The IEM uses an iterative approach to simulate combustion gas propagation by calculating venting of gas between grids as steady isentropic flow through a perfect nozzle for both sonic and subsonic flow regimes until either pressure stabilizes or a maximum number of iterations is reached. This iteration allows for consideration of complex structures with arbitrary barriers and openings as the model is allowed to run until the gases have sufficient time to propagate throughout.

The venting process between two grids (with the direction of flow detailed by labeling a from grid and a to grid) is described by assuming the ideal gas law and subsequent relations. First, the average heat capacity ratio is estimated for the propagating gas mixture as Equation 15.

Heat Capacity Ratio Determination — Equation 15

$$\gamma = \frac{c_p}{c_p - R_0}$$

Where:

$\gamma$ is the average heat capacity ratio of the gas mixture.

$c_p$ is the heat capacity at constant pressure of the gas mixture weighted by the number of moles present of each gas.

$R_0$ is the ideal gas constant.

When pressure in the from grid is greater than the pressure in the to grid, venting occurs. When the ratio of the to pressure to the from pressure exceeds a critical ratio—described in Equation 16—then Equation 17 is used to determine the subsonic molar rate of flow. When the ratio is less than or equal to the critical ratio, Equation 18 is used to determine the sonic (choked) flow rate.

Critical Ratio Determination — Equation 16

$$R_{crit} = \left(\frac{2}{\gamma_{from} + 1}\right)^{\frac{\gamma_{from}}{\gamma_{from}-1}}$$

Subsonic Molar Rate of Flow — Equation 17

$$\frac{dn_{from}}{dt}\bigg|_{subsonic} = \left(\frac{\gamma_{from} g n_{from} P_{from}}{m_{from} V_{from}}\left(\frac{2}{\gamma_{from}-1}\right)\left[1 - \left(\frac{P_{to}}{P_{from}}\right)^{\frac{\gamma_{from}-1}{\gamma_{from}}}\right]\right)^{\frac{1}{2}}$$

Sonic Flow Rate — Equation 18

$$\frac{dn_{from}}{dt}\bigg|_{sonic} = A_0 \left[\gamma_{from}\left(\frac{2}{\gamma_{from}}\right)^{\frac{\gamma_{from}+1}{\gamma_{from}-1}} \frac{g n_{from} P_{from}}{m_{from} V_{from}}\right]^{\frac{1}{2}}$$

Where:

from is the label for the grid the venting gas originated from.

to is the label for the grid the gas was venting into.

$R_{crit}$ is the critical pressure ratio determining the type of flow between two grids.

$\gamma$ is the average heat capacity of the gas mixture.

dn/dt is the rate at which gas vented in moles per second.

g is the acceleration due to gravity at sea level.

n is the number of moles of gas in a grid.

P is the absolute pressure in a grid.

m is the molar ratio weighted average molecular mass for the gas mixture in a grid V is the volume of the grid.

$A_0$ is the area of the vent opening between the from grid and the to grid.

The vent duration is then calculated by examining the change in internal energy of the venting gas to derive the number of moles in total vented.

Vent Duration — Equation 19

$$\Delta U_{to} = U_{to} \frac{1 - \left(V_{to}^{\gamma_{to}-1} / V_{from}^{\gamma_{from}-1}\right)}{1 + \left(V_{to}^{\gamma_{to}-1} / V_{from}^{\gamma_{from}-1}\right)}$$

$$\Delta n_{to} = \Delta U_{to} \cdot \frac{n_{to}}{\gamma_{to} U_{to}}$$

$$\Delta t = \frac{\Delta n_{to}}{5 \cdot \frac{dn}{dt}}$$

Where:

from is the label for the grid the venting gas originated from.

to is the label for the grid the gas was venting into.

U is the internal energy of the gas.

$\Delta U$ is change in the internal energy of the gas.

$\Delta n$ is change in the number of moles of the gas present in the grid.

$\Delta t$ is the duration of venting.

The combustion gas model outputs the maximum pressure, impulse, barrier failure level, and temperature for each of the impacted grids due to heat and venting.

Interior Debris Propagation

Starting at the location of the explosive device, the casing and fragmentation enhancement debris is propagated to all adjacent grids. A quarter of the total number of available fragments were distributed in each initial direction. This process is illustrated in FIG. 38. FIG. 38 illustrates Initial Debris Expansion 3800 according to an embodiment.

For each subsequent step, half of the fragments propagated to the grid in the direction of the initial fragment vector. A quarter propagated to each grid in the direction perpendicular to the direction of motion, shown in FIG. 39. FIG. 39 illustrates Fragment Propagation 3900 according to an embodiment.

This algorithm approximately calculates debris distributed in a spherically symmetric manner originating at a point source, shown in FIG. 40. FIG. 40 illustrates Spherical Propagation 4000 according to an embodiment.

Figure 41:
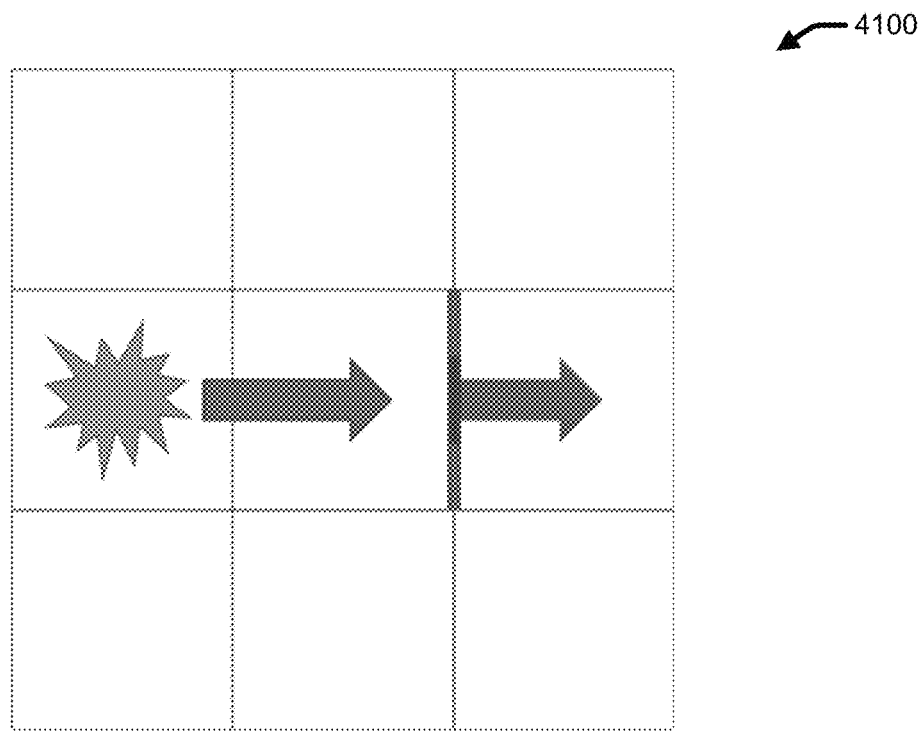
FIG. 41 illustrates Barrier Failure according to an embodiment.

If a barrier fails due to the shockwave, the broken barrier materials form fragments that are accelerated by applied shockwave pressure and impulse. FIG. 41 illustrates Barrier Failure 4100 according to an embodiment.

Figure 42:
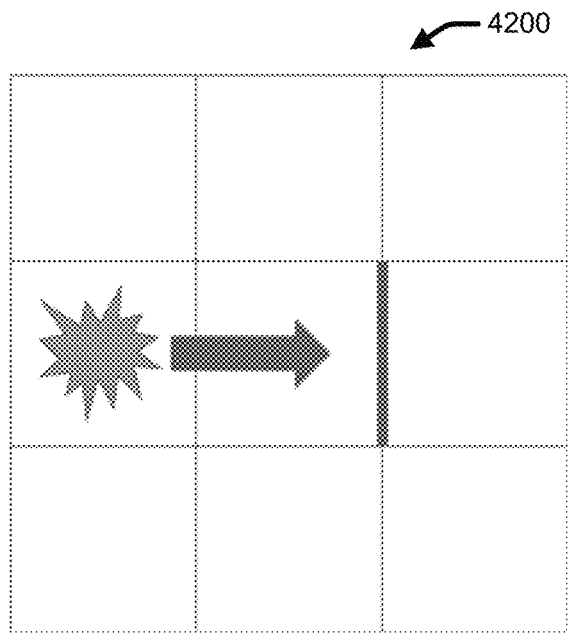
FIG. 42 illustrates No Barrier Failure according to an embodiment.

When debris encounters a barrier in the direction of propagation, the force of impact is compared to the barrier's failure curve. If the barrier does not fail, debris propagation is halted in that direction. FIG. 42 illustrates No Barrier Failure 4200 according to an embodiment.

Figure 43:
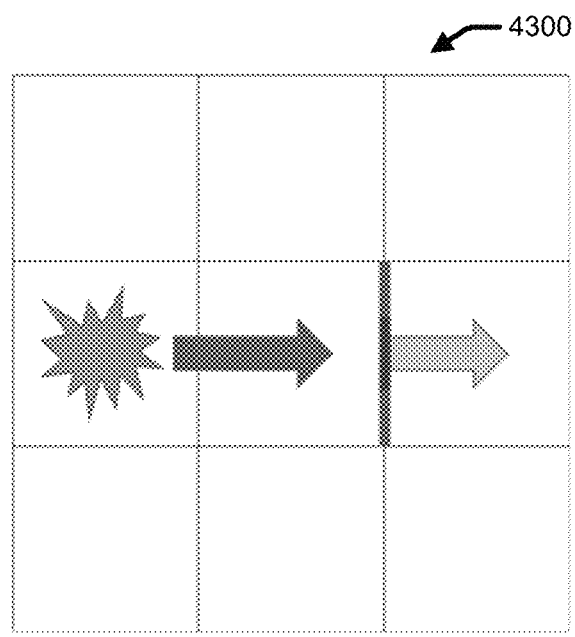
FIG. 43 illustrates Barrier Failure, Energy Reduction according to an embodiment.

If the barrier does fail, the kinetic energy of the fragments is reduced by the amount of energy required for the barrier to fail. Fragments with remaining energy greater than zero continue propagating past the destroyed barrier. FIG. 43 illustrates Barrier Failure, Energy Reduction 4300 according to an embodiment.

Mott's distribution is a semi-empirical framework that describes the number of fragments produced by the detonation of a naturally fragmenting bomb casing—i.e., a casing made of materials that expand plastically before rupture—derived from two experimental parameters: the average mass of fragments collected and the total fragment mass.

Two approaches based on Mott's distribution are used within the IEM to characterize fragment distributions due to casing and barrier destruction. In both approaches, the Mott's distribution is inverted and used to calculate fragment masses for percentile-based bins.

The distribution of casing fragmentation is determined through the following procedure:

Given a cylindrical casing's thickness, dimensions, and density, the casing mass is calculated.

$$m_c = \pi(t_o t_c - t_c^2) \cdot h_c \cdot \rho_c \quad \text{Equation 20: Casing Mass Calculation}$$

Where:
$m_c$ was the total casing mass.
$t_o$ is the outside diameter of the casing.
$h_c$ is the casing height.
$t_c$ is the casing thickness.
$\rho_c$ is the density of the casing material.

A fragment distribution parameter that is dependent on the explosive geometry and material is calculated.

Fragment Distribution Parameter  Equation 21

$$M_A = B \cdot t_c^{0.833} \cdot (t_o - 2t_c)^{0.333} \cdot \left(1 + \frac{t_c}{t_o - 2t_c}\right)$$

Where:
$M_A$ is the fragment distribution parameter.
B is the material explosive constant.
$t_o$ is the outside diameter of the casing.
$t_c$ is the casing thickness.

Explosive constant B is experimentally determined for a variety of materials. Through further analysis it is found to correlate with the Gurney characteristic velocity as in Equation 22.

$$B = -0.0014 \cdot G + 6.758 \quad \text{Equation 22: Explosive Constant Determination}$$

Where:
B is the material explosive constant.
G is the Gurney characteristic velocity.

The fragment mass distribution is then characterized as Equation 23.

Fragment Mass Distribution Characterization  Equation 23

$$\bar{m}_f = 2 M_A^2$$

$$N = \frac{m_c}{\bar{m}_f}$$

$$m_f = M_A^2 \cdot \ln^2\left(\frac{n_f}{N}\right) = M_A^2 \cdot \ln^2(p)$$

Where:
$\bar{m}_f$ is the average fragment mass.
$M_A$ is the fragment distribution parameter.
N is to total number of fragments created from the casing.
$m_c$ is the total casing mass.
$m_f$ is the mass such that some number $n_f$ or percentile of fragments was greater than $m_f$.
$n_f$ is the number of fragments greater than mass $m_f$.
p is the percentile of a fragment of mass $m_f$.

A different procedure is used to develop a fragment mass distribution for barriers destroyed by the air blast. The theory from Dehn generalizing the Mott's distribution is applied to the context of incident energy on destructible barriers. Equation 24 was derived by inverting Dehn's equation.

$$D(p) = (\ln(1 - p + p \cdot \exp(-u)))^2 \quad \text{Equation 24: Fragment Mass Distribution}$$

Where:
D(p) is the inverted Dehn's distribution function evaluated at percentile p.
p is the percentile of the distribution.
u is the proportion of the applied energy to the energy necessary to destroy the barrier.
$m_{min}$ is the imposed minimum fragment mass.
$\bar{m}_f$ is the average fragment mass, calculated with the energy proportion and total mass of the destroyed barrier as $$\bar{m}_f = \frac{m_{barrier}}{u^2} + m_{min}.$$

The fragment mass at some percentile is then determined using this distribution with Equation 25.

Fragment Mass at Percentile  Equation 25

$$m_f = \frac{D(p_{n+1}) - D(p_n)}{2}$$

Where:

D(p) is the inverted Dehn's distribution function evaluated at percentile p.

$p_n$ is the percentile of the nth mass bin.

$p_{n+1}$ is the percentile at the top of the nth mass bin.

The debris propagation model outputs the debris density and velocity levels for each impacted grid.

Exterior Shockwave Propagation

Shockwave propagation via Expansion, Reflection, and Diffraction are calculated using the simplified Kingery equations, similar to the approaches used by BlastX. All surfaces are treated as perfectly reflecting. Only first order reflections are considered; medium changes are assumed to be negligible.

Figure 44:
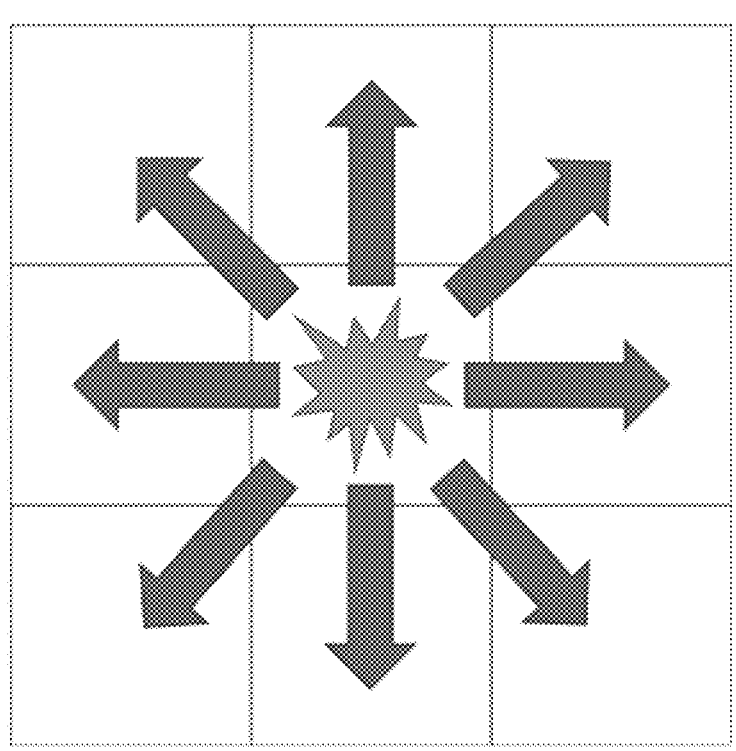
FIG. 44 illustrates Spherical Shockwave according to an embodiment.

Starting at the location of the explosive device, an air blast, or shockwave, expands linearly into all directions, illustrated in FIG. 44. FIG. 44 illustrates Spherical Shockwave 4400 according to an embodiment. The incident pressure and impulse are calculated using the distance from the shockwave source, which is then used to calculate the probability of pressure induced injuries.

Figure 45:
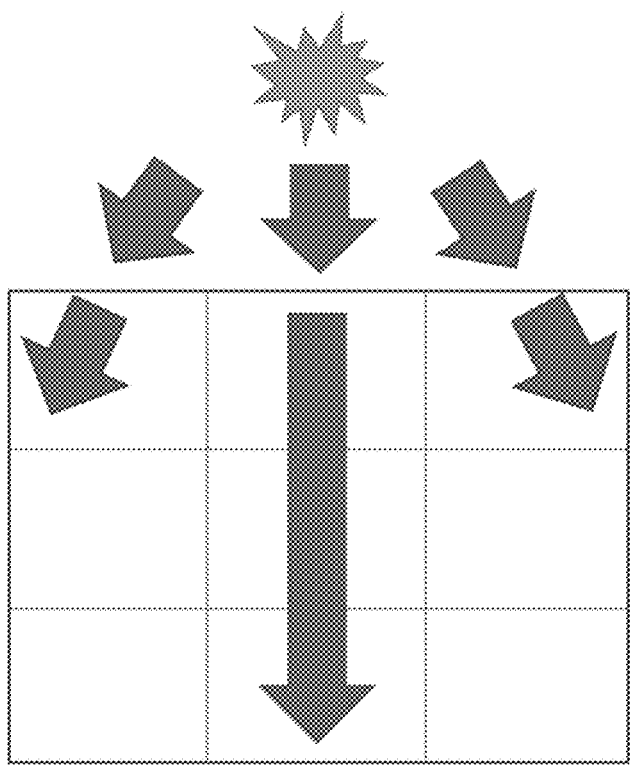
FIG. 45 illustrates Blast Propagating Through Building according to an embodiment.

The shockwave from the exterior-placed explosive propagates through buildings based on the location of the blast using the same methodology as previously described for propagation of a shock wave within a building. FIG. 45 illustrates Blast Propagating Through Building 4500 according to an embodiment.

For outdoor populations, only the distance from the blast is considered. Barrier reflection or failure is not considered.

Exterior Debris Propagation

The fragmentation creation and propagation for the population indoors are calculated using bins of mass and velocity, as described in the section, Interior Debris Propagation. Mott's distribution and Gurney characteristic velocity are used for casing fragments. Near-in impulse, mass, and drag coefficient are used to calculate velocity of added fragmentation. The Reynolds dependent drag coefficient is used for propagation calculations. Velocity of fragmentation from barrier failures is estimated using a general form of Mott's distribution.

Figure 46:
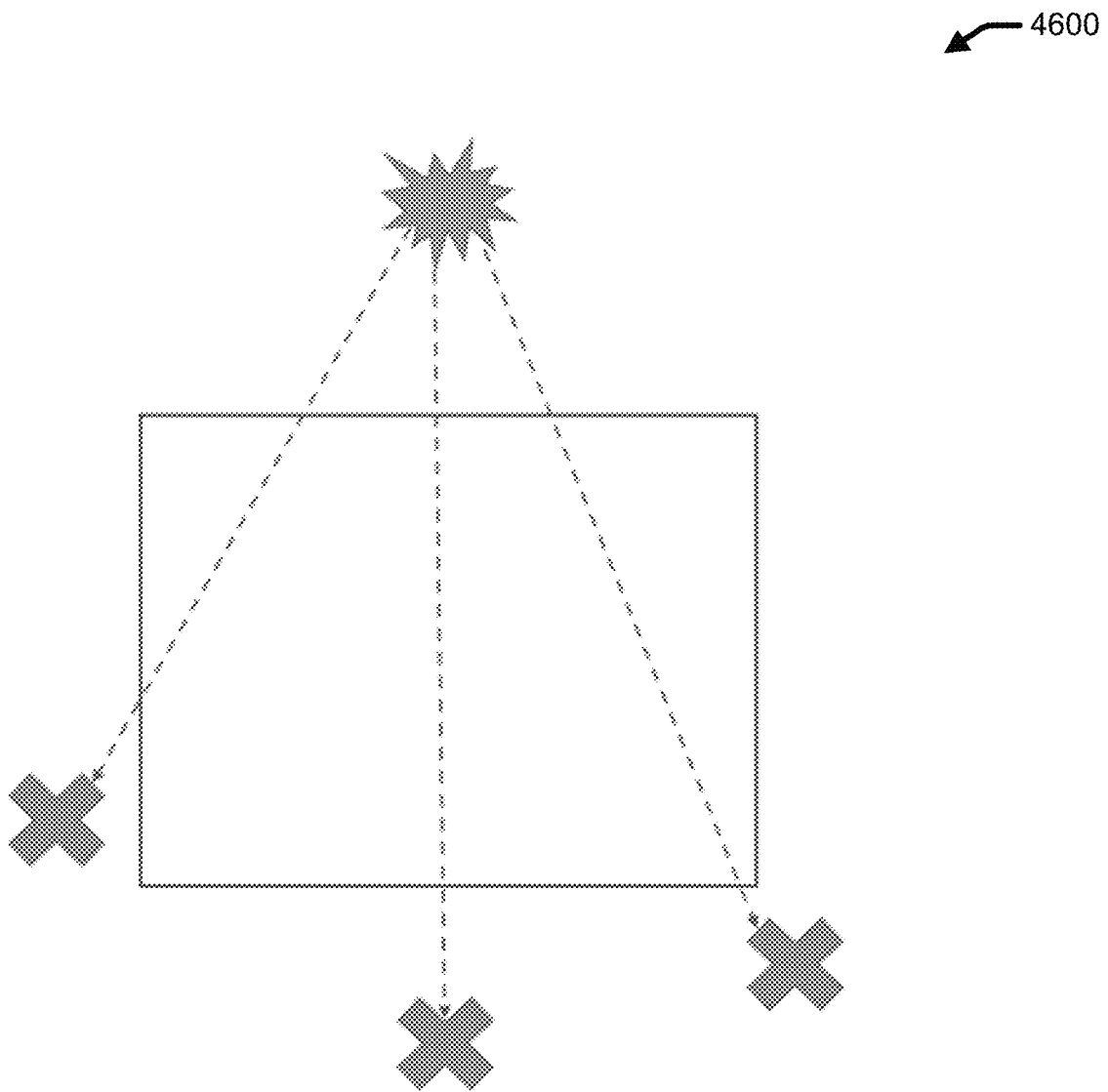
FIG. 46 illustrates Example Shielded Population according to an embodiment.

The Exterior Model also considers building shielding for debris calculations for the population outdoors. Based on building geometries and blast location, it can be determined whether a grid space is behind a building. Population that is outdoors but behind a building relative to the blast is "shielded" and is considered safe from debris and radiation related injuries (depicted in FIG. 46). FIG. 46 illustrates Example Shielded Population 4600 according to an embodiment. Analogously, if the blast is indoors but none of the phenomenon propagate past the building barriers, then all outdoor population is "shielded." Building shielding only protects against debris injuries and thermal radiation injuries however, and the population that is shielded is still subject to injuries due to the other phenomenon, such as shockwaves.

Exterior Combustion Gas Propagation

The thermal hazard is estimated by calculating the increase in gas temperature from the increased pressure and the heat evolved by combustion reactions. Combustion gases are calculated using prioritized reactions, similar to the BlastX model. Heating is estimated using the heat of formation for the molecules involved. A fireball is assumed to occur at temperatures of 1300° C. and above. The ideal gas law is assumed.

Radiant Heat Propagation

Unlike the IEM, the EEM considers radiant heat from rising fireballs as a result of combustion gas propagation.

Martinsen proposed a dynamic fireball model related to many of the methods given by TNO. The algorithm given leads to heat flux as a function of known values of heat of combustion, explosive mass, burst pressure, distance from the blast, and time. This is a significant improvement on Engelhard's proposed model as shown.

Figure 47:
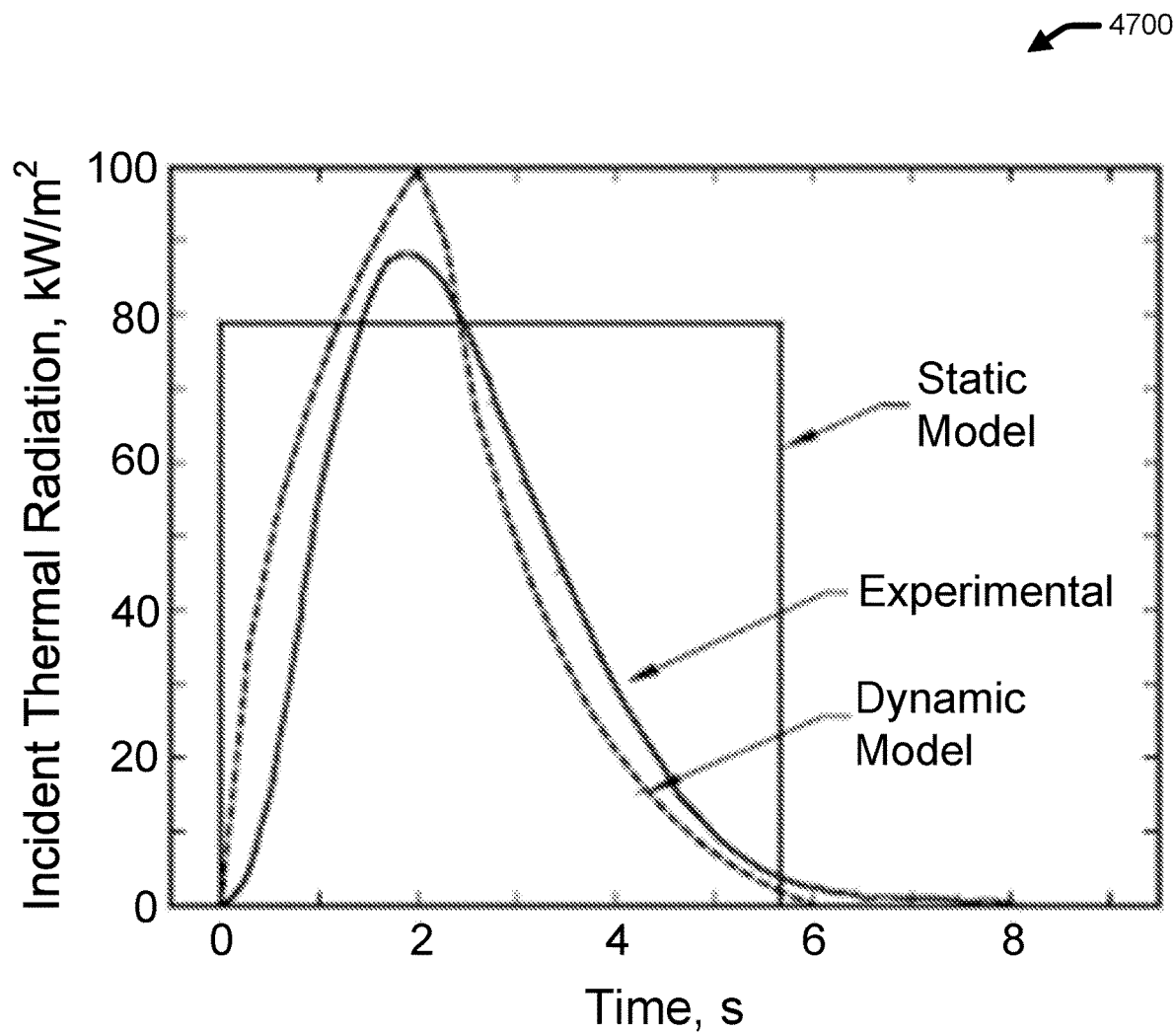
FIG. 47 illustrates Static vs Dynamic Thermal Radiation Model according to an embodiment.

FIG. 47 illustrates Static vs Dynamic Thermal Radiation Model 4700 according to an embodiment.

A series of equations, all taken from Martisen, are used in order to calculate the radiant heat flux from fireballs. The equations are provided below.

The first step is to calculate the fireball duration, using the equation below:

$$t_d = 0.9 \cdot M^{0.25} \qquad \text{Equation 26: Fireball Duration Calculation}$$

Where:

M is explosive mass in kg;

$t_d$ is the fireball duration;

Next, the liftoff time is calculated $$t_{lo} = t_d/3 \qquad \text{Equation 27: Liftoff Time Calculation}$$

Where:

$t_{lo}$ is the fireball duration;

The fireball diameter is calculated using the duration $$D(t) = 8.664 \cdot M^{1/4} \cdot t^{1/3} \text{ for } t \leq t_{lo}, \text{ constant} \qquad \text{Equation 28: Fireball Diameter}$$

Where:

D (t) is the fireball diameter;

The height of the fireball is calculated using the diameter and the duration.

Height Calculation $\qquad$ Equation 29

$$h(t) = 1.5 \cdot D(t_{lo}) \frac{(t - t_{lo})}{(t_d - t_{lo})} t \geq t_{lo}, \text{ constant } t \leq t_{lo}$$

Where:

h(t) is the fireball height;

The fraction of heat radiated is calculated using the burst pressure.

$$f = 0.27 \cdot P^{0.32} \qquad \text{Equation 30: Fraction of Heat Radiated}$$

Where:

P is burst pressure in N/m² f is the fraction of heat radiated

The surface emissive power is calculated.

Surface Emissive Power $\qquad$ Equation 31

$$q_s = \frac{f \cdot H_c \cdot M}{0.888 \cdot \pi \cdot D(t_d)^2 \cdot t_d}$$

Where:

$H_c$ is Heat of Combustion in J/kg;

$0.888 \cdot \pi \cdot D(t_d)^2$ is time averaged surface area;

$q_s$ is the surface emissive power

The view factor is calculated

View Factor $\qquad$ Equation 32

$$F(t, x) = \frac{D(t)^2}{4 \cdot (h(t)^2 + x^2)}$$

Where:
x is distance in m from the blast
F(t, x) is the view factor
The saturated water pressure is calculated in bar for the ambient temperature Saturated Water Pressure $$\log_{10} P_{H_2O} = 4.65430 - \frac{1435.264}{T - 64.848}$$ Equation 33

Where:
$P_{H_2O}$ is the saturated water pressure
The atmospheric absorption is calculated for a flame of 1500 K.

$$X(H_2O) = (R_H \cdot x \cdot P_{H_2O} \cdot 2.8865 \times 10^2)/T$$

$$X(CO_2) = 273 \cdot x/T$$

$$\tau_a(x) = 1.006 - 0.01171 \log_{10} X(H_2O) - 0.02368(\log_{10} X(H_2O))^2 - 0.03188$$

$$\log_{10} X(CO_2) + 0.001164(\log_{10} X(CO_2))^2$$ Equation 34: Atmospheric Absorption Where:
$R_H$ is relative humidity
$P_{H_2O}$ is Saturated Water Vapor Pressure in mmHg
T is ambient temperature in K
$X(H_2O)$ is the water along the length of the fireball
$X(CO_2)$ is the $CO_2$ along the length of the fireball
Finally, the heat flux is calculated.

$$q''(t,x) = q_s \cdot F(t,x) \cdot \tau_a(x)$$ Equation 35: Heat Flux

Where:
q"(t, x) is heat flux
The heat flux is used to calculate thermal injuries.

Calculating Injury Probability

The HExCAT models provide an estimation of human health outcomes following an attack with an explosive. Explosive events generate multiple hazards that can lead to various injury categories. The injury categories considered in the HExCAT are:

Lung injury caused by either the initial shockwave of the blast or combustion gases;
Traumatic brain injury (TBI) caused by the initial shockwave of the blast or combustion gases;
Whole body displacement (WBD) caused by the initial shockwave;
Thermal injury caused by heat generated from the combustion gases;
Debris injury caused by initial device fragmentation or failed barriers; and
Building collapse injury caused by structural failures.

Probit equations are used to convert physical properties of the blast (pressure, impulse, temperature, etc.) to probability of fatality, major injury, and minor injury.

In the Injury model, the severity for each of hazard-related injury for an individual is tracked using the Abbreviated Injury Scale (AIS). The AIS is a consensus-derived global severity scoring system developed by the Association for the Advancement of Automotive Medicine that classifies each type of injury onto a six-point scale. The AIS classifies individual injuries as either:

AIS 1—Minor, no chance of fatality;
AIS 2—Moderate, non-life threatening;
AIS 3—Severe, non-life threatening;
AIS 4—Serious, survival likely;
AIS 5—Critical, survival uncertain; or
AIS 6—Not survivable.

Translation from the language of fatal, major, and minor injury probabilities to the language of AIS used throughout the HExCAT requires a statistical treatment. First, the probability of injury is determined for each injury type through the use of a probit analysis. The probability is calculated as the area under the standard normal distribution to the left of the developed probit curve (usually indicated as $Y_{f(injury\ type)}^{-1}$) This probability is then converted to the probability of falling within the consequence category.

$$P_{fatality.category} = P_{fatality.event}$$

$$P_{major.category} = P_{fatality.category}(1 - P_{major.event})$$

$$P_{minor.category} = P_{minor.event}(1 - P_{fatality.category} - P_{major.category})$$

Equation 36: Injury Probability to Consequence Probability

The injury probability is then related to the mean of the category's distribution, as determined via linear regression:

$$\mu = m \cdot P + b$$ Equation 37: Injury Probability Regression Equation

Where:
μ is the mean of the consequence category distribution;
P is the probability of injury; and
m and b are regression parameters fit for each category.

TABLE 38

Linear Fit Parameters for AIS Score Conversion

| Category | m | b |
| --- | --- | --- |
| Fatal Injury | 1 | 5 |
| Major Injury | 1 | 3 |
| Minor Injury | 1 | 1 |

The variance is assumed to be 1 for each category. These means and variances are used to generate independent truncated normal distributions over the AIS range for each type of injury. As the AIS scale includes only integer values, the probability of any AIS value is taken as the cumulative probability ranging from half-integer below the AIS value to the half-integer above the MS value.

Injuries derived from different mechanisms (shockwave, fragmentation, thermal, building collapse) are then combined by calculating an aggregated Injury Severity Score (ISS) that considers the effects of multiple hazards on a single individual, and translates this to a generalized, descriptive injury scale.

Individual injury types are described in detail below:

Overpressure Injuries

Overpressure injuries encompass all injuries caused by excessive pressure and impulse as induced by the shockwave and venting hazards within the HExCAT. Three types of injuries fall into this category: lung rupture (soft tissue), whole body displacement, and skull fracture. The procedure to calculate these injuries was adapted from IME SAFER and APT research, which used a language of fatal, major, and minor injuries. In conjunction with APT research, a schema was devised that translated these categories to the AIS standard categories.

Soft Tissue

Lung damage, also known as soft tissue damage, occurs when a pressure difference arises between the inside and outside of the lungs. In overpressure situations, the thorax is pressed inwards due to a large exterior pressure. It has been experimentally shown that for short exposures to overpressure, the duration is only represented in the probability of injury through the calculation of total impulse.

Fatal lung injuries are calculated from of a probit curve, which is dependent on the scaled pressure and impulse as in Equation 38, adapted from the TNO Green Book.

Lung Injury Probit Curve                              Equation 38

$$P_{scaled} = \frac{P_{exposed}}{P_{STP}}$$

$$I_{scaled} = \frac{I_{exposed}}{\sqrt{P_{STP}} \cdot \sqrt[3]{m}}$$

$$Y_{f(lr)}^{-1} = -5.74 \cdot \ln\left(\frac{4.2}{P_{scaled}} + \frac{1.3}{I_{scaled}}\right)$$

Where:
$P_{scaled}$ is a measure of overpressure experienced by an individual;
$P_{exposed}$ is the absolute pressure experienced by an individual;
$P_{STP}$ is the ambient pressure at room temperature;
$I_{scaled}$ is a measure of overimpulse experienced by an individual;
$I_{exposed}$ is the absolute impulse experienced by an individual;
m is the average mass of an individual; and
$Y_{f(lr)}^{-1}$ is the inverse probit function that governs the probability of a fatal lung rupture injury.

Figure 48:
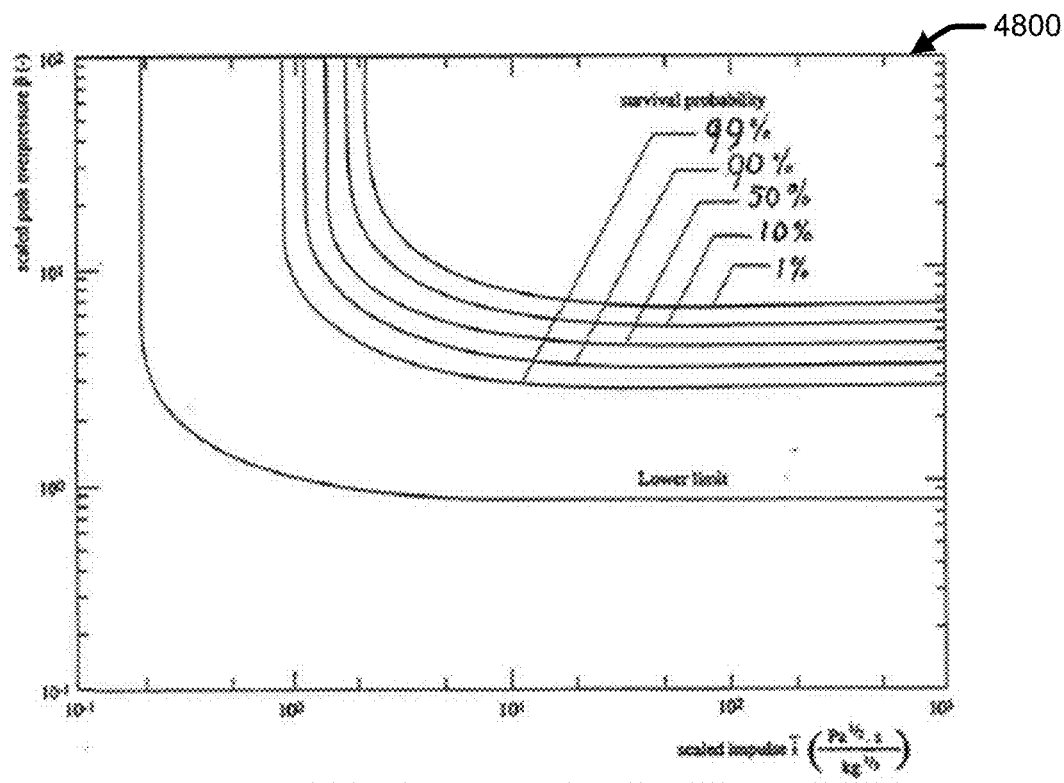
FIG. 48 illustrates Pressure-Impulse for Lung Damage/Soft Tissue Damage according to an embodiment.

FIG. 48 illustrates Pressure-Impulse for Lung Damage/Soft Tissue Damage 4800 according to an embodiment.

The probabilities of major and minor lung injuries are determined by curve fitting injury data to a linear function. (Note: the regression was originally computed in pressure units of pounds/square inch (psi), therefore a conversion factor of 6894.76 PSI/Pa remains in Equation 39.

Soft Tissue Probit Curve                              Equation 39

$$P_{maj(lr)} = 0.01 \cdot \frac{P_{expose}}{6894.76 \frac{PSI}{Pa}} - 0.18$$

$$P_{min(lr)} = 0.032 \cdot \frac{P_{expose}}{6894.76 \frac{PSI}{Pa}} - 0.046$$

The AIS score and injury descriptions for soft tissue injures are summarized in the table below, based on a number of sources.

TABLE 39

AIS Scores and Injury Descriptions: Soft Tissue

| Category | Description | AIS Score |
|---|---|---|
| Mild/Moderate | Bruises and ruptured eardrum. | 1 |
| Severe | Minor contusions of lungs. | 2-3 |
| Life-Threatening | Unilateral or Bilateral pulmonary peripheral hemorrhage. | 4-5 |
| Fatal | Lung damage with less than 1% chance of survivability | 6 |

Whole Body Displacement

Whole body displacement occurs when the air particles displaced by a blast pick up and displace an individual over some distance. During this displacement, injuries occur due to an individual tumbling and sliding over surfaces as well as colliding with fixed, rigid objects (i.e. furniture, walls, etc.). Fatal injuries caused by whole body displacement can be primarily attributed to these collisions.

A probit function was constructed, using existing literature, to determine the probability of fatality due to whole body displacement.

Fatality Probit Curve                              Equation 40

$$Y_{f(wbd)}^{-1} = -2.44 \cdot \ln\left(\frac{7280 \text{ Pa}}{P_{exposed}} + \frac{1.3 \cdot 10^9 \text{ Pa} \cdot N \cdot s}{P_{exposed} \cdot I_{exposed}}\right)$$

Figure 49:
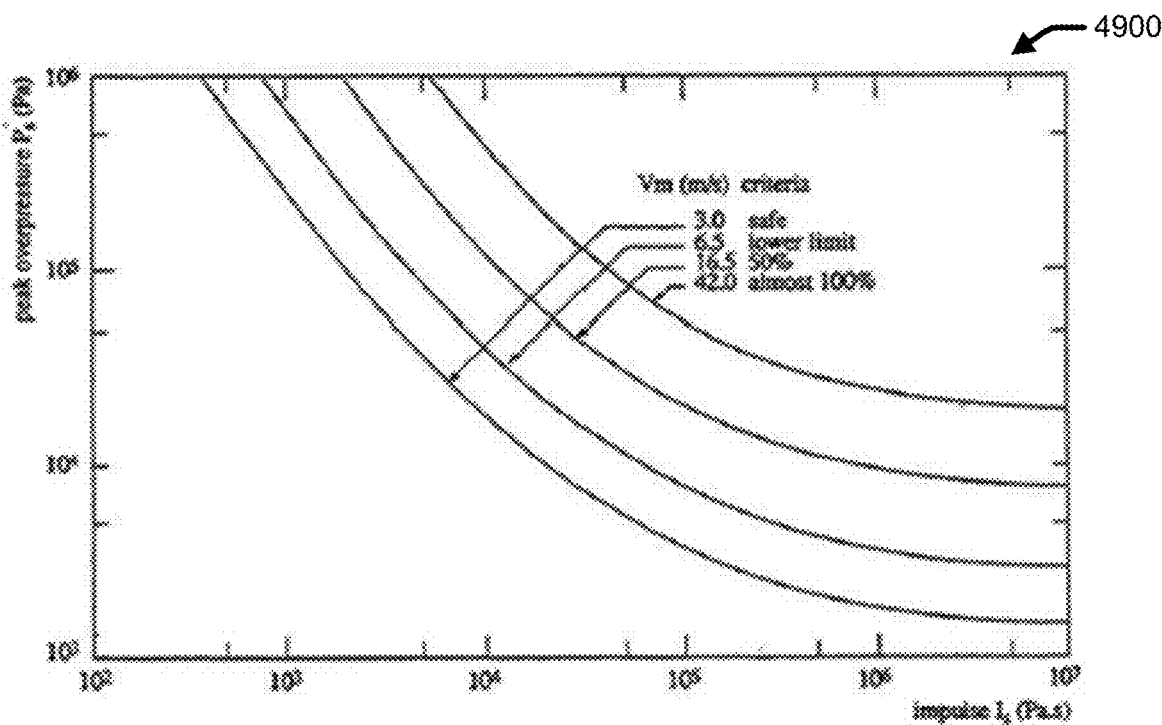
FIG. 49 illustrates Whole Body Displacement Probit Curve according to an embodiment.

The fatality probability is used to determine the probability of major $P_{maj(wbd)}$ and minor $P_{min(wbd)}$ injuries from whole body displacement.

$$P_{maj(wbd)} = 1 - \exp(-7 \cdot P_{f(wbd)})$$

$$P_{min(wbd)} = 1 - \exp(-7 \cdot P_{maj(wbd)})$$   Equation 41: Probability of a fatal whole body displacement injury FIG. 49 illustrates Whole Body Displacement Probit Curve 4900 according to an embodiment.

The AIS score and injury descriptions for whole body displacement are summarized in the table below.

TABLE 40

AIS Scores and Injury Descriptions: Whole Body Displacement

| Category | Description | AIS Score |
|---|---|---|
| Mild/Moderate | Wrist Sprain. | 1 |
| Severe | Open comminuted fracture to tibial shaft. | 2-3 |
| Life-Threatening | Vertical shear fracture to the left side of the pelvis. | 4-5 |
| Fatal | Crushed pelvis and/or extremities. | 6 |

Skull Fracture

During whole body displacement and displacement of rigid non-fixed objects by a shockwave hazard, it is possible for an individual to experience skull fracture. A probit function was constructed to determine the probability of fatality due to skull fracture.

Skull Fracture Probit Curve                              Equation 42

$$Y_{f(sf)}^{-1} = -8.49 \cdot \ln\left(\frac{2430 \text{ Pa}}{P_{exposed} - P_{STP}} + \frac{4.0 \cdot 10^8 \text{ Pa} \cdot N \cdot s}{(P_{exposed} - P_{STP}) \cdot I_{exposed}}\right)$$

The fatal probability is used to determine the probability of major $P_{maj(sf)}$ and y minor $P_{min(sf)}$ injuries from skull fracture.

Probability of Fatal Skull Fracture Injury  Equation 43

$$P_{maj(sf)} = \begin{cases} 0.25 \cdot P_{f(sf)}, & P_{f(sf)} < 0.01 \\ -1.34 \cdot P_{f(sf)}^2 + 2.09 \cdot P_{f(sf)} + 0.25, & P_{f(sf)} \geq 0.01 \end{cases}$$

$$P_{min(sf)} = \begin{cases} 10 \cdot P_{maj(sf)}, & P_{f(sf)} < 0.01 \\ -1.34 \cdot P_{maj(sf)}^2 + 2.09 \cdot P_{maj(sf)} + 0.25, & P_{f(sf)} \geq 0.01 \end{cases}$$

Figure 50:
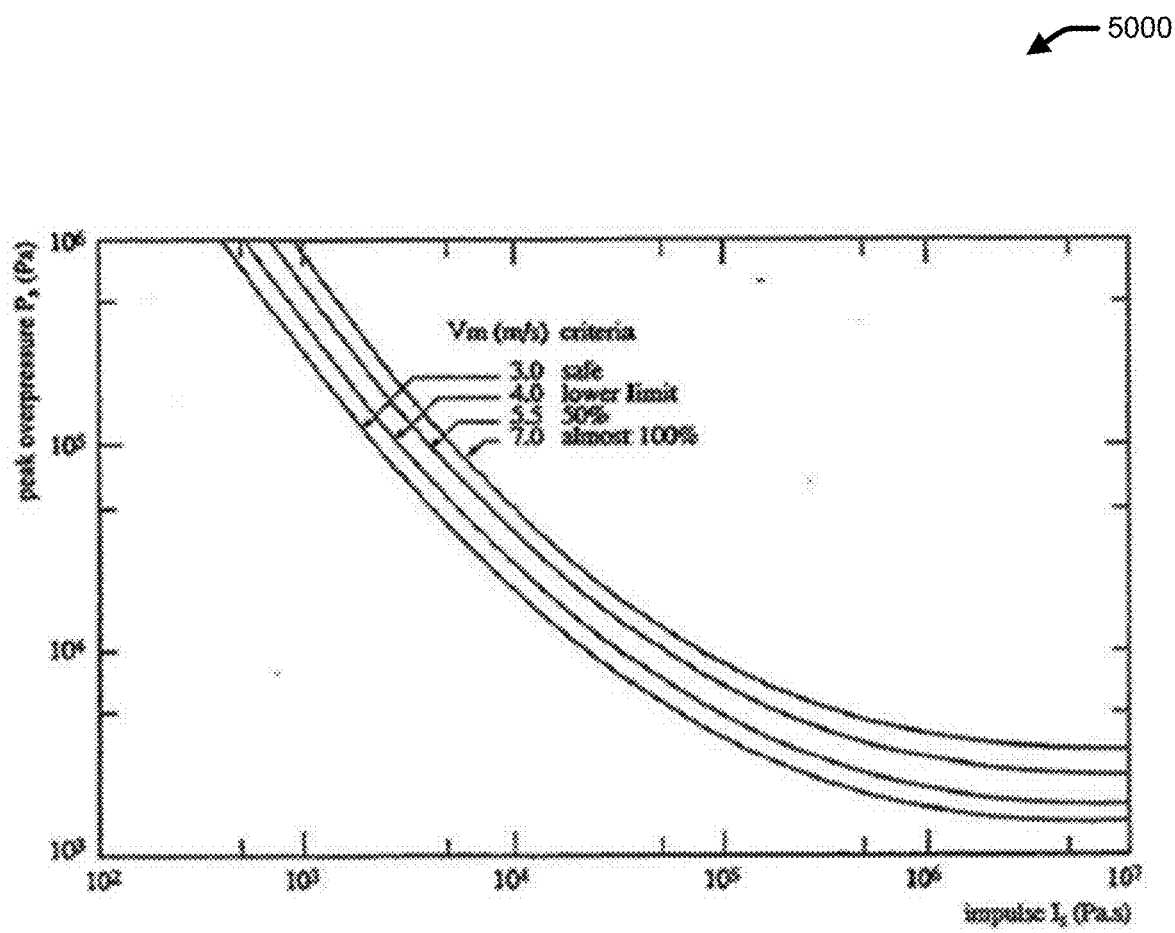
FIG. 50 illustrates Skull Fracture Probit according to an embodiment.

FIG. 50 illustrates Skull Fracture Probit 5000 according to an embodiment.

The AIS score and injury descriptions for skull fractures, which are used as an approximation for TBI, are summarized in the table below.

TABLE 41

AIS Scores and Injury Descriptions: Skull Fracture

| Category | Description | AIS Score |
|---|---|---|
| Mild/Moderate | Minor concussion | 1 |
| Severe | Fracture of skull, penetration less than 2 cm | 2-3 |
| Life-Threatening | Depressed skull fracture, penetration greater than 2 cm | 4-5 |
| Fatal | Massive brain stem crush | 6 |

Debris Injuries

Debris injuries occur when casing and enhancement fragmentation as well as fragmentation from barrier destruction contact individuals. The presence of fragments within a grid that contain a human is insufficient to declare that contact had occurred. Instead, the probability of striking a target within a grid is calculated based on the area and density of fragments as projected on a plane normal to the fragment trajectory, as in Equation 44.

Probability Fragment Strikes Human  Equation 44

$$q = \frac{N}{\left(\frac{A}{2\pi}\right)^2}$$

$$P_{strike} = 1 - \exp(-A_{target} \cdot q)$$

Where:
q is the areal density of incident fragments;
N is the total number of incident fragments;
A is the cross sectional area fragments are dispersed over;
$P_{strike}$ is the probability that a fragment would strike a human; and
$A_{target}$ is the cross sectional area of the strike target, here a human at assumed 0.58 m².

The severity of injury caused when an individual is struck by debris is dependent on the mass and velocity of the traveling fragment. A family of AIS correlation curves was used in the explosive models to estimate injuries of AIS score 2 and higher.

A separate method is used to provide a minimum mass and velocity relation for AIS 1 injuries. A 1978 Lewis study that investigated the probability of skin penetration for low density debris was adapted for this method. The Walker-Duncan method was utilized to perform a curve fit of two independent variables and given as an equation of form:

AIS 1 Determination  Equation 45

$$P(AIS \geq 1) = \frac{1}{1 + \exp(-(a + b \cdot \ln(mv^2/A)))}$$

Where:
P(AIS≥1) is the probability that the injury severity was at least AIS 1—i.e. skin penetration occurred;
a and b are curve fitting parameters;
m is the fragment mass;
v is the fragment velocity; and
A is the cross-sectional area of the fragment;

Parameters a and b are provided for bare skin, a two-layer cloth military garment, and a six-layer cloth military garment. It is assumed that a random draw between the probability of penetration for bare skin and the probability of penetration through a two-layer cloth garment adequately describe typical civilian clothing.

TABLE 42

Fit parameters for AIS 1 Injury Curve

| Target | a | b |
|---|---|---|
| Bare Skin | −28.42 | 2.94 |
| Two-Layer Uniform | −48.47 | 4.62 |

The AIS score and injury descriptions for debris injuries are summarized in Table 43 below.

TABLE 43

AIS Scores and Injury Descriptions: Debris Injuries

| Category | Description | AIS Score |
|---|---|---|
| Mild/Moderate | Some mild lacerations and contusions | 1 |
| Severe | Many lacerations or minor laceration of an artery | 2-3 |
| Life-Threatening | Leg amputation, major artery lacerations, or internal organ perforation. | 4-5 |
| Fatal | Major penetrating wound to the heart | 6 |

Thermal Injuries

An AIS Injury profile for thermal injuries is devised based on a combination of technical literature and modelling assumptions. Firstly, all population in grids with temperature greater than 1,573.45 K (1,200.45 C) are assigned an injury status of AIS 6.

Figure 51:
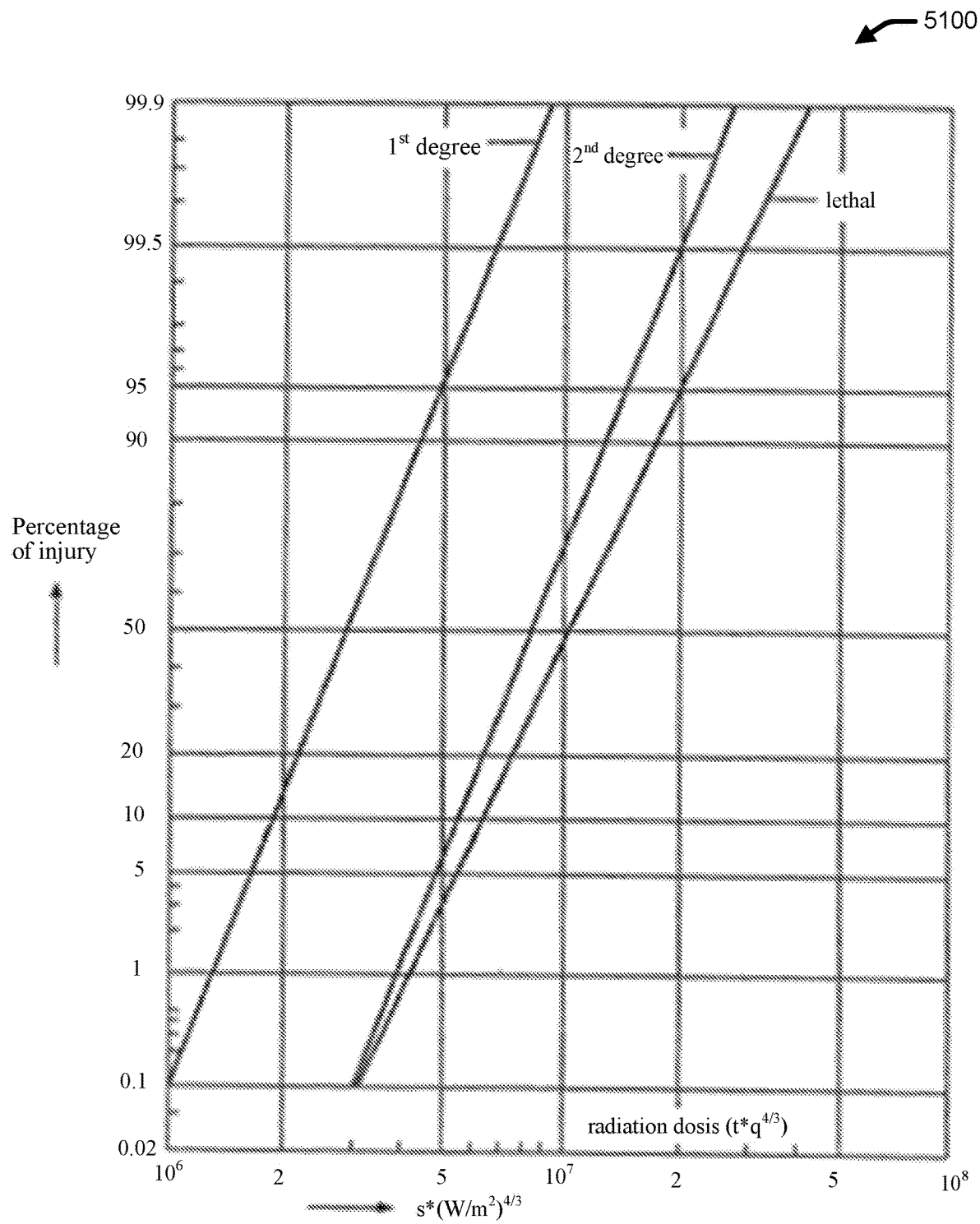
FIG. 51 illustrates Burn Probit according to an embodiment.

The remaining probit functions for injury to bare skin were derived by van den Bosch for "fires of hydrocarbons", which is used for determining burn injuries. The equations for each burn level are below, and the probit function is depicted in FIG. 51. FIG. 51 illustrates Burn Probit 5100 according to an embodiment:

$P_{1st(burn)} = -39.83 + 3.0186 \cdot \ln(t \cdot q^{4/3})$  Equation 46: First Degree Burn Probit Equation $P_{2nd(burn)} = -43.14 + 3.0186 \cdot \ln(t \cdot q^{4/3})$  Equation 47: Second Degree Burn Probit Equation $P_{fatal(burn)} = -36.38 + 2.56 \cdot \ln(t \cdot q^{4/3})$  Equation 48: Lethality Burn Probit Equation Where:
q is the flux density of radiation (J/m²)
t is the length of exposure to radiation flux q Clothing is also considered when calculating burn injuries. Clothing on average when exposed to thermal radiation reflects 50%, transmits 30%, and absorbs 20% of the thermal radiation. An average of data for Specific Mass(density), Specific Heat, and Mean Auto Ignition Temperature for 20 various clothing materials, with the absorption percentage was used to calculate the temperature of clothing over time was. Another important consideration is that clothing significantly reduces burns on the covered skin, almost exclusively igniting before serious burns occur to the area.

Using this information, a process was developed to convert the probit curves to the injury levels. The steps are as follows:

1. Calculate distance from center of fireball. If distance is less than radius of fireball, or grid is burned during venting, 100% fatality.
2. Calculate temperature of the "averaged" clothing. If temperature exceeds auto ignition temperature, 100% fatality. This assumption was based on the TNO Injury book.
3. Calculate the flux corrected for clothed and unclothed skin.
4. For a given flux and location, calculate the value of each probit function.
    a. Note the probabilities do not sum to 100% necessarily
    b. Percentage of skin with $2^{nd}$ degree burn is probability of skin with second degree burn and not a third-degree burn. In other words, multiply probability of $2^{nd}$ degree by 1−probability of $3^{rd}$ degree.
5. Add together percentage of skin burned for each burn category and translate to AIS score based on the midpoint of injury definition.
6. AIS 4—30% to 55% second- or third-degree burn Because the probit functions must be used to calculate each person's individual burn percentage and AIS score as opposed to the percentage of people with $1^{st}$ degree burns, all individuals in a single grid are assumed to have the same thermal injury.

The AIS score and injury descriptions for thermal injuries are summarized in the table below.

TABLE 44

AIS Scores and Injury Descriptions: Thermal Injuries

| Category | Description | AIS Score |
| --- | --- | --- |
| Mild/Moderate | $1^{st}$ degree burns or $2^{nd}$ degree burns covering less than 10% of the body | 1 |
| Severe | Any $3^{rd}$ degree burns or $2^{nd}$ degree burns covering 10-29% of the body | 2-3 |
| Life-Threatening | $2^{nd}$ or $3^{rd}$ degree burns covering 30-89% of the body. | 4-5 |
| Fatal | $2^{nd}$ or $3^{rd}$ degree burns covering at least 90% of the body. (AIS: 6)[1] | 6 |

Collapse Injuries

AIS Injury profiles for each collapse designation were assigned based on a combination of technical literature, SME input, and modelling assumptions.

Population in grids labeled collapsed are distributed as $\frac{1}{3}^{rd}$ AIS 6, $\frac{1}{6}^{th}$ AIS 5, $\frac{1}{6}^{th}$ AIS 4, and $\frac{1}{3}^{rd}$ AIS 3. This distribution is based on a combination of field studies, historical events in which victims had been unearthed and survived, and the perception that many of those victims would have died without treatment.

Population in grids labeled adjacent are distributed as ½ AIS 3 and ½ AIS 2 based on field studies and the assumption that building collapse will not cause a life-threatening injury in sections of the building that did not collapse.

Population in grids labeled impacted are distributed as ½ AIS 2 and ½ AIS 1 based on the assumption that only minor injuries are expected in areas of the building distant from the collapse.

Compound Injuries

It is possible (and even likely) for an individual to experience more than one type of injury as the result of an explosive event within the HExCAT. For instance, an individual close to the detonation site might have been thrown by a shockwave (experiencing whole body displacement) and received a skull fracture upon landing. This example victim then might have suffered perforation by casing fragmentation, severe burns from the thermal component of the explosive, and finally a collapse injury as the explosion destroyed supports at their location.

The HExCAT uses the Injury Severity Scale (ISS) as a metric for compound injuries to multiple body locations. An individual's ISS score is determined by summing over the squares of each separate injury. If the total ISS exceeds 60—e.g. via two AIS 5 injuries and an AIS 4 injury (25+25+16>60)—then the combined injuries are considered fatal. Additionally, the individual receives a fatal ISS if any of the individual injuries are fatal.

Figure 52:
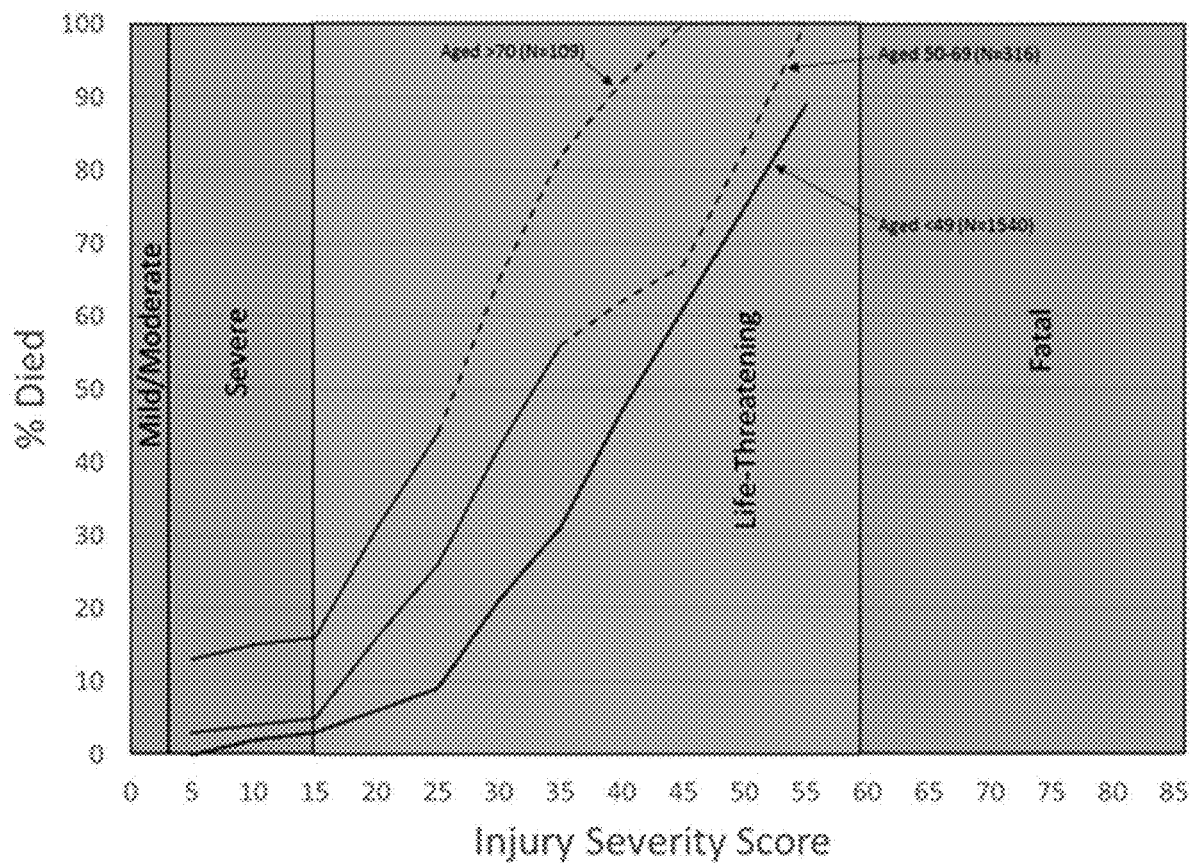
FIG. 52 illustrates Mortality by ISS for three age groups according to an embodiment.

The models output a translation of the compounded ISS scores to a more conventional language that classified consequences into Mild/Moderate, Severe, Life-threatening, and Fatal as shown in FIG. 52, and Table 45.

TABLE 45

Scale Translation of Injury Severities

| Injury Severity Score | Injury Classification |
| --- | --- |
| 0 | Uninjured |
| 1-3 | Mild/Moderate |
| 4-15 | Severe |
| 16-59 | Life-threatening |
| 60+ | Fatal |

FIG. 52 illustrates Mortality by ISS for three age groups 5200 according to an embodiment.

Medical Mitigation

If users had selected to run the medical mitigation model as part of their scenario, the results from the injury results from the explosive model are used as inputs to define the medical response. Each simulation has its own medical response simulated; if the user selected 1,000 simulations while defining the scenario, then 1,000 unique medical systems corresponding to the explosive model simulations will be constructed and the outputs will be generated for those 1,000 simulations. The purpose of medical mitigation is to simulate the efficacy of the medical response through simulation of the progression of victims and the impact of the medical treatments on those victims through parameterization of key events and activities. The outcome of the model is estimates for the number of victims that would be saved by or benefit from the actions of first responders, medical personnel, and local, state, and national authorities as well as estimate the hospital routing patterns and countermeasures consumed during treatment. Such a modeling capability allows HExCAT to account for the nation's ability to respond to explosive attacks, permits assessment of the existing medical response system, and provides a means of evaluating improved mitigation strategies to best prepare for a potential attack (e.g., increased countermeasure stockpiling).

An explosive-focused medical response model was developed to address injuries due to explosive attacks. The model included the identification of blast related injuries as well as their appropriate treatment pathways. The foundation for the Medical Mitigation Model is the concept of stock-and-flow modeling. Originating from system dynamics, a "technique for framing, understanding, and discussing complex issues and problems," the stock-and-flow approach is common when modeling intricate systems that change over time. For the Medical Mitigation Model, stocks are states or stages through which victims progress during a response. For example, initially all victims are located in the "Attack Site" stock. Flows represent rates of change, allowing victims to move from one stock (state) to another. Flows are typically manipulated or governed by events or actions. This same methodology is applied to other consumable resources, such as medical personnel, medical countermeasure, and facility resources.

Figure 53:
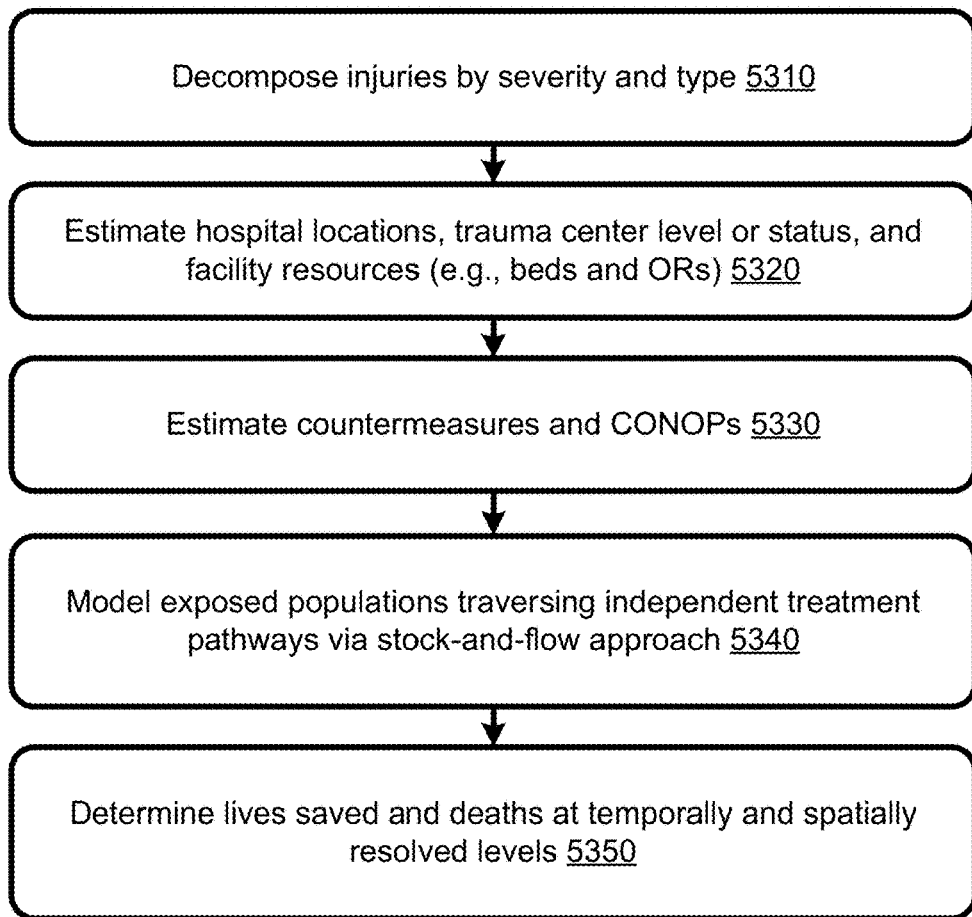
FIG. 53 illustrates a flowchart to determine lives saved and deaths using a stock and flow approach according to an embodiment.

FIG. 53 illustrates a flowchart 5300 to determine lives saved and deaths using a stock and flow approach according to an embodiment. At 5310, the computer system decomposes injuries by severity and type. For example, the computer system determines whether victims suffer from mild injury such as burns or severe injury such as collapsed lungs. At 5320, the computer system estimates hospital locations, trauma center level or status, and facility resources (e.g., beds and ORs). For example, the computer system consults a database to determine local medical resources within a given distance to the location of the device detonation. At 5330, the computer system estimates countermeasures and CONOPs. For example, the computer system estimates what medical countermeasure resources are available to help victims, and what the medical operations are for co-locating victims with medical assistance. At 5340, the computer system models exposed populations traversing independent treatment pathways via stock-and-flow approach. For example, victims are grouped by injury severity and the groups are independently flowed through the various stocks of treatment. At 5350, the computer system determines lives saved and deaths at temporally and spatially resolved levels. For example, the computer maintains information on the location of victims forming the groups for spatial resolution, and maintains timing information associated with the groups of victims flowing through the various stocks of treatment.

Figure 54:
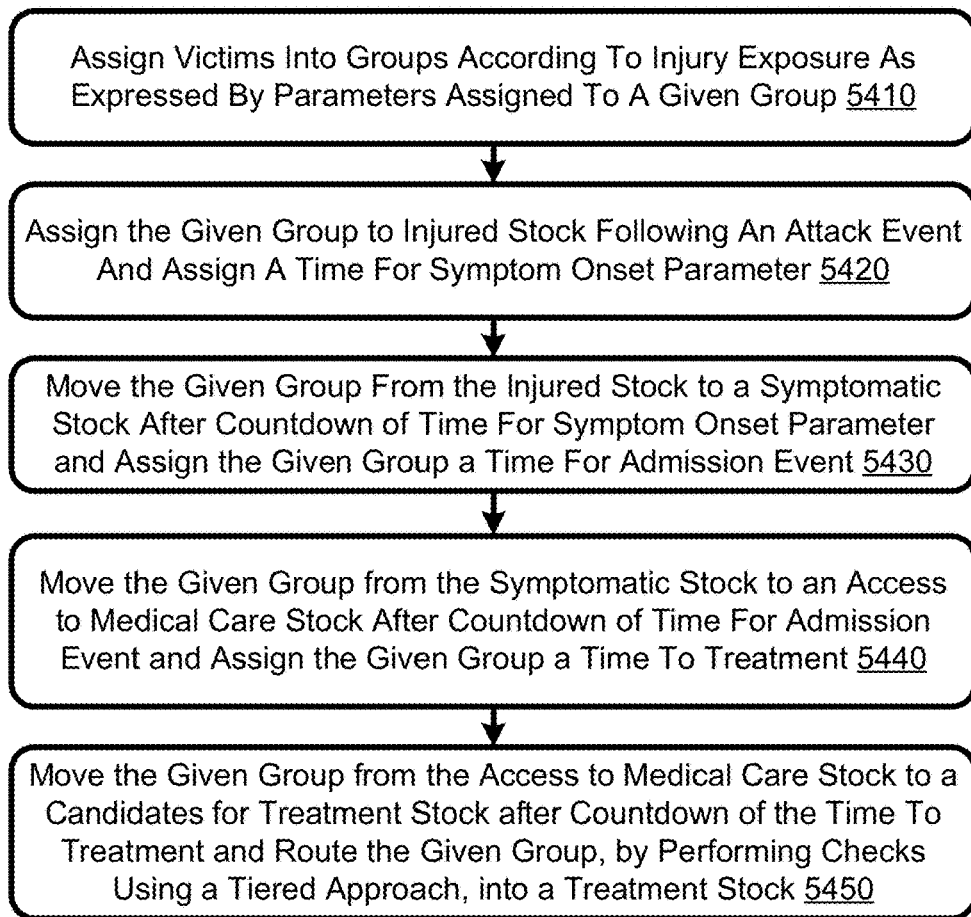
FIG. 54 illustrates a flowchart of stock-and-flow movement of groups to a treatment stock according to an embodiment.

FIG. 54 illustrates a flowchart 5400 of stock-and-flow movement of groups to a treatment stock according to an embodiment. At 5410, the computer assigns victims into groups according to injury exposure as expressed by parameters assigned to a given group. For example, a given group may be assigned victims having a parameter of burn injury. At 5420, the computer system assigns the given group to an injured stock following an attack event, and assigns a time for symptom onset parameter. For example, the given group of the injured stock may have lung damage that takes some time before the onset of symptoms (assigned a longer time), or may have burn damage whose onset of symptoms is immediate (assigned a shorter time). At 5430, the computer system moves the given group from the injured stock to a symptomatic stock after countdown of time for symptom onset parameter, and assigns the given group a time for admission event. For example, the computer system can assign the time for admission event as a function of available medical resources, expressed as a probabilistic range of time parameters. At 5440, the computer system moves the given group from the symptomatic stock to an access to medical care stock after countdown of time for admission event, and assigns the given group a time to treatment 5440. For example, the computer system simulates whether an admission event will occur, and determines a likely time before the victims receive treatment based on medical information available for the area. At 5450, the computer system moves the given group from the access to medical care stock to a candidates for treatment stock after countdown of the time to treatment, and routes the given group, by performing checks using a tiered approach, into a treatment stock. For example, the computer system can track many different available treatments, and assign a group to that type of treatment stock suited for the type of injury of the group.

Figure 55:
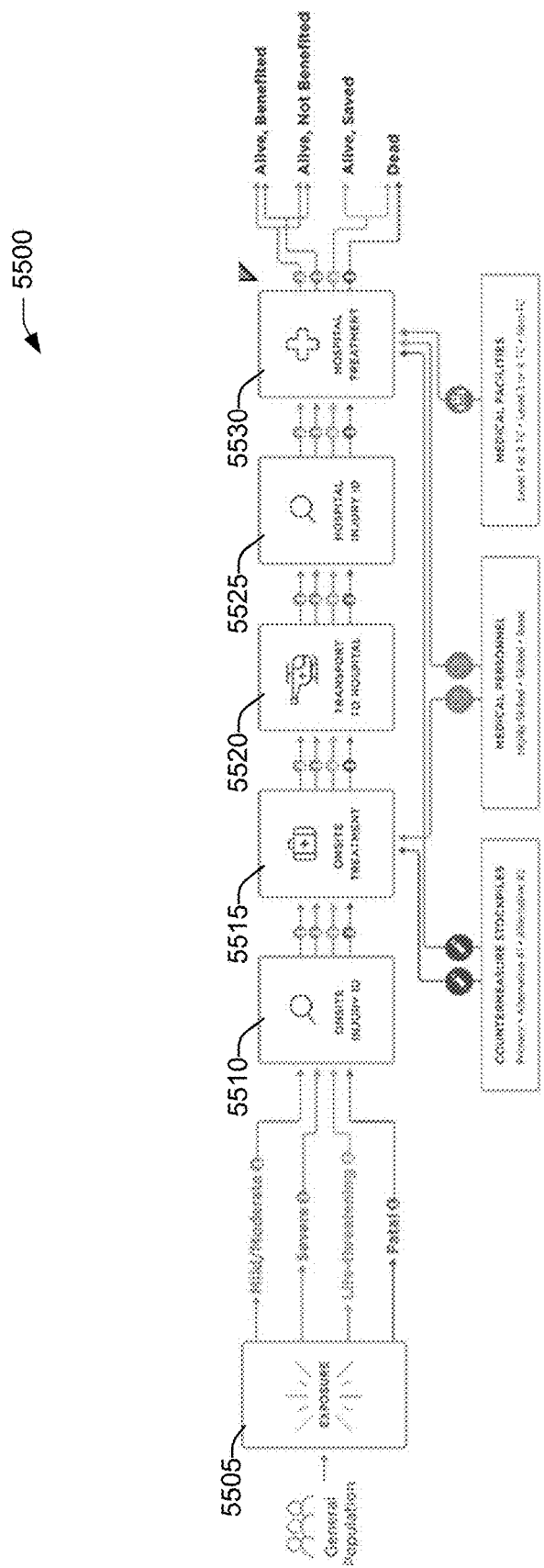
FIG. 55 illustrates a chart depicting dynamics between victims, medical countermeasures, medical personnel, and medical facilities according to an embodiment.

FIG. 55 illustrates a chart 5500 depicting dynamics between victims, medical countermeasures, medical personnel, and medical facilities according to an embodiment. The victims arise from the general population experiencing exposure 5505 to an attack. The victims traverse the chart 5500 horizontally left to right with four eventual outcomes: alive, benefited; alive, not benefited; alive, saved; and dead. The victims pass through various stocks or states including onsite injury identification 5510, onsite treatment 5515, transport to hospital 5520, hospital injury identification 5525, and hospital treatment 5530. Medical countermeasures (e.g., countermeasure stockpiles) corresponds to onsite treatment 5515 and hospital treatment 5530. Medical personnel corresponds to onsite treatment 5515 and hospital treatment 5530. Medical facilities corresponds to hospital treatment 5530. The computer system uses probabilistic methods to move the victims through the stocks or states, e.g., according to parameters weighted by injury severity shown as mild/moderate, severe, life-threatening, and fatal.

In the most extreme case, the Medical Mitigation Model resembles agent-based modeling in that each individual/victim in a scenario is simulated as an independent "agent," progressing through the system of stocks and flows separately. For the sake of computational efficiency, in an embodiment, individuals with similar exposures are pooled together into groups and their movement through the system is treated as identical. Individuals placed into the same group are assumed to have the same response (e.g., efficacy of treatment), receive the same treatments, and have the same final outcome (e.g., death). Groups are not permanent though, if a group of 10 is seeking a treatment with countermeasures for 5 doses, the group will split into two groups with only one group receiving treatment.

Parameters, such as that representing the delay for symptom onset, are generally defined as a distribution, allowing the model to account for variability and uncertainty surrounding victim attributes. The model samples from these distributions when parameters/attributes are assigned to the groups. Some parameters are sampled for each group and, thus, different groups in the same simulation are assigned different values for the same parameter. Therefore, while the individuals in any one group share the same set of values, the individuals in another group share a completely different set of values.

The stock-and-flow modeling approach permits assignment of unique attributes to the different groups of victims, and thus it is possible to directly link the attack scenario consequence simulation results with the medical mitigation simulations. For each consequence model simulation performed for HExCAT, there is one correlated medical mitigation simulation. Additionally, for each simulation, the responsible consequence model provides the number of injuries and other key details, such as the type and severity of each injury. Such correlation enables the HExCAT to reflect a realistic progression and outcome for each event.

Figure 56:
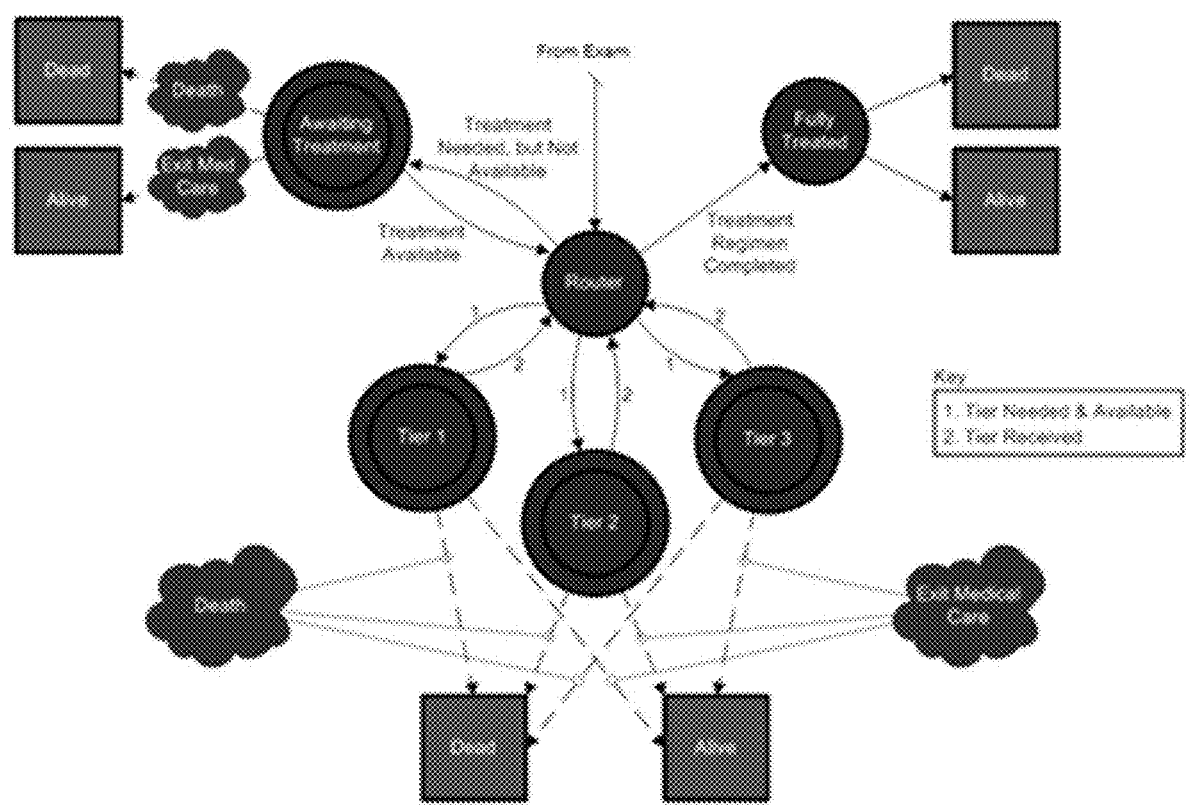
FIG. 56 illustrates a chart with stocks or states, and a router to move victims around the positions illustrated in the chart according to an embodiment.

FIG. 56 illustrates a chart 5600 with stocks or states, and a router to move victims around the positions illustrated in the chart 5600 according to an embodiment. The different states are associated with dead or alive outcomes. The alive outcome can be associated with an exit from medical care.

Following the attack event groups are placed into the injured stock. Here, each group samples a value from the appropriate distribution for the time for symptom onset parameter. The countdown for symptoms to appear begins immediately. When a group's time for symptom onset eventually elapses, the Symptom Onset event is executed, and the group is subsequently moved to the Symptomatic stock. Most injuries caused by explosives will have an immediate symptomology onset, but blast lung requires the quantification of symptom onset. Individuals suffering from blast lung may not show any symptoms immediately after the blast.

Upon entry into the Symptomatic stock, groups with life-threatening and fatal injuries sample a value from the time to die parameter distribution. The drawn time to die can be increased, based on the application of life-extension treatments. However, if a group's time to die elapses at any point prior to receiving an efficacious treatment, the group exits the simulation, and the group moves to the dead end-state.

Entrance into the Symptomatic stock signifies the start of victims seeking care for their injuries. To account for the delays in co-locating medical personnel with injured groups, a collocation time is considered. All groups sample multiple values from input distributions to form the collocation time. The collocation time depends on a variety of factors, including behavior parameters such as the speed of walking to triage, transport parameters and distance to hospitals and/or triage sites. When the group is collocated with medical personal, the admission event executes, and the group moves to the Access to Medical Care stock. The victims may be admitted either to a triage site, a triage site followed by a hospital, or directly to a hospital.

Victim group hospital routing is determined by vehicle type, more specifically whether or not the victims are being transported in a personal vehicle or emergency transport vehicle. For EMS transport the hospital selection is based on a probability draw that is a function of hospital distance, hospital trauma level, and resources available (stockpiles, staff, space).

When patients need to be transported to the hospital the hospital distribution decision parameters account for factors that govern hospital selection. Such parameters include distance to the hospital, hospital trauma level, and, in the case of emergency vehicles, whether or not the hospital has the resources to treat the victims. The parameters associated with the hospital distribution decision are defined below.

The distance limit is the maximum distance that victims will be transported to a hospital. For example, if the maximum distance is 50 km, then hospitals outside the 50 km radius from the attack have a 0 percent chance of victims being transported there for treatment. The maximum distance value is also used to define the linear relationship between distance and hospital routing probability.

The injury trauma level restriction is a binary value that specifies whether or not an injury severity prevents victims from seeking out certain trauma levels. Here, true indicates that the severity restricts the victim from being routed to the designated trauma levels.

Victims with more severe injuries are more likely to seek larger, better equipped better known hospitals (i.e., Trauma Level 1 and 2). The trauma level contribution accounts for this by allowing weights to be set for each trauma level (Trauma 1 through Non-Trauma) for each given severity level.

The distance, resources, and trauma level factors that affect hospital routing decisions are combined in a linear combination for each victim and hospital combination. With the hospital distribution decision weights, one is able to specify what parameters are the driving factors when impacting routing. For each of the three factors, a multiplicative weight is uniquely defined.

Before calculating the probability given a hospital's trauma level or distance, if transport is through EMS the hospital selector determines whether or not hospitals within the area of interest have the available resources needed to treat the victim group. If a hospital has the resources, then for all vehicles it moves to the probability calculator to determine the probability that the victim group will be routed to that hospital. Distance and hospital selection have a linear relationship with the probability of routing to a hospital decreasing the farther away it is from the attack location. The trauma level contribution varies and is further described below. In general victim groups with life-threatening injuries have a greater probability of being transported to a better equipped hospital for trauma injuries than if the victim group had mild/moderate injuries.

The victims then experience a delay, known as the time to treatment ID, for medical personnel to determine the injury and severity level of the group. Both the on-site and hospital locations have unique distributions associated with the time to treatment ID. This in turn governs the treatment pathway that the group will then receive. The time delay begins to elapse immediately upon co-location. After the time to treatment ID elapses, the group moves to the Candidates for Treatment stock. The Exam stock records the number of groups that pass through and their size.

Figure 57:
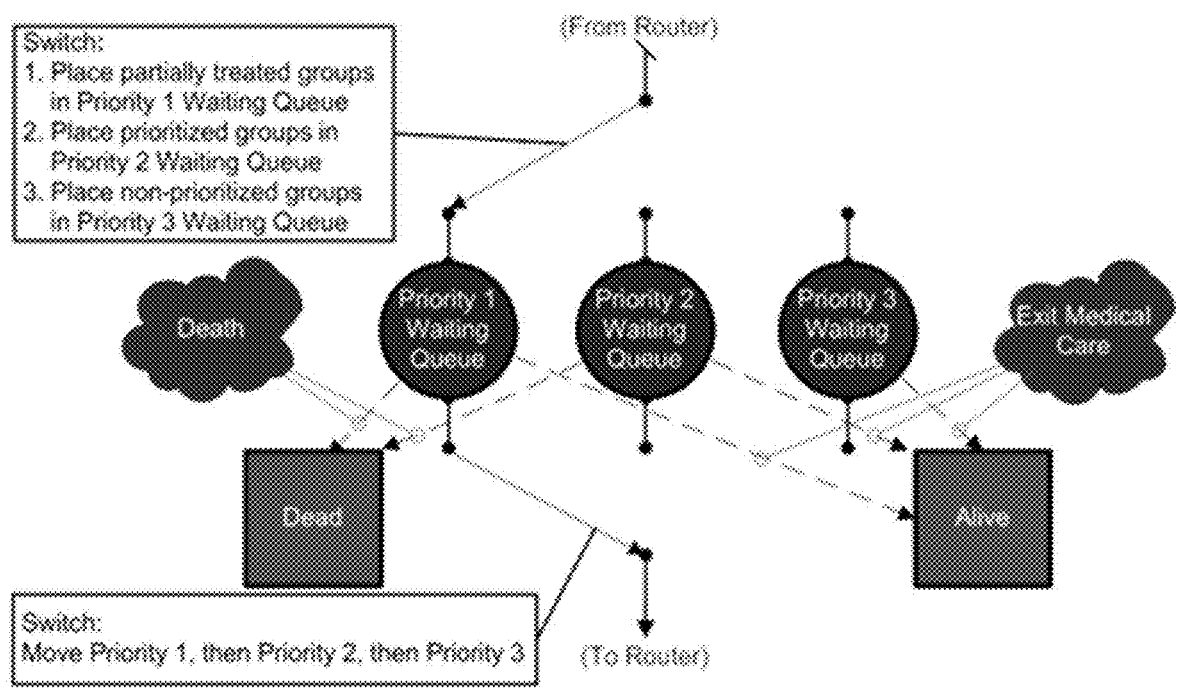
FIG. 57 illustrates a chart with dead or alive outcomes, and switches to direct victims to different queues illustrated in the chart according to an embodiment.

FIG. 57 illustrates a chart 5700 with dead or alive outcomes, and switches to direct victims to different queues illustrated in the chart 5700 according to an embodiment. The different waiting queues correspond to victims grouped according to whether they are partially treated, prioritized, or non-prioritized. The queues are fed by the router.

When a group enters the Candidates for Treatment stock, it is instantly pushed into the Router. The Router then tries to place the incoming group into one of the treatment stocks (e.g., Tier 1). FIG. 57 is simplified to show only 3 treatment stocks. Though in the model, a treatment stock exists for every unique treatment used across all injury types and severities. If victim types share a treatment, they also share that treatment stock. To ensure that treatment competition and delays were accurately captured, each treatment stock has a treatment capacity limited by stuff (countermeasures), staff (medical personnel), and space (beds, operating rooms, etc.). Groups can only be treated in parallel if they can be accommodated by the response system.

When trying to place a group into a treatment stock, the Router makes the following checks:
Tier 1:
    A higher priority group is not present in the Awaiting Treatment stock;
    The treatment stock us not already fully occupied by other groups;

A restriction factor (i.e., the benefited restriction factor [BRF] or the side effect or availability restriction factor [SEARF]) does not prevent the group from being a candidate for that particular countermeasure;

The group has not already received this tier (primary or alternative); and

The countermeasure is available (primary or alternative), medical personnel are available to administer it, and there is an operating room or bed available in which to administer the countermeasure or perform the procedure.

Tier 2
All Tier 1 checks; and
The group has already received the Tier 1 treatment or if Tier 1 is not required, the group must not be able to receive Tier 1 treatment.

Tier 3
All Tier 2 checks; and
The group has already received the Tier 2 treatment or if Tier 2 is not required, the group must not be able to receive Tier 2 treatment.

If a group is unable to be placed into any of the treatment stocks because of a restriction factor, the group is moved to the appropriate end-state via the Fully Treated stock. If a group is unable to be placed into a treatment stock because of any of the other checks, it is moved into the Awaiting Treatment stock. The Router continually re-attempts to place the groups in the Awaiting Treatment stock into a Treatment stock. Once the above checks are satisfied and the group is inside one of the prescribed treatment stocks, the administration of that treatment is modeled.

The Awaiting Treatment stock is structured to allow for prioritization based on the triage efficacy parameter. This parameter considers both on-site and hospital efficacy when prioritizing victim groups. Although this parameter is configurable, both efficacy parameters are set to 1 indicating that victim severity will be prioritized over arrival every time when queuing for treatment.

Groups entering the Awaiting Treatment stock are sorted based on the group combined injury severity or Injury Severity Scale score (ISS). Second to severity priority, is the arrival time. After assessing severity priority, when the groups have equivalent severity, they are then prioritized based on arrival.

For example, Priority 1 Waiting Queue would consist of severely injured groups who arrived earliest to triage or the hospital. Whereas the Priority 2 Waiting Queue would consist of severely injured victims who arrived later. Priority 3 would then contain mild/moderate injured groups regardless of the time they arrived for treatment. Any victim without life-threatening injury could not have a higher priority and hinder the progression of victims with life threatening injuries.

When the required countermeasures are available and capacity exists to administer them, the bottom Switch (see FIG. 57) sends any groups in the Priority 1 Waiting Queue to the Router (to be subsequently sent to a treatment stock). If the Priority 1 Waiting Queue is empty, groups from the Priority 2 Waiting Queue are sent to the Router solely by order of appearance. Groups from the Priority 3 Waiting Queue are only sent to the Router when the Priority 2 Waiting Queue is empty.

The rate at which an available treatment is administered is determined by its administration time. Upon treatment initiation, the definitive treatment efficacy of the treatment is also calculated. Definitive treatment efficacy is uniquely defined for every allowed combination of countermeasure, injury type, and severity as a function of time. It is widely recognized that the efficacies of most medical interventions are highly dependent on how quickly they can be administered to patients in need. Time zero in the definitive treatment efficacy versus time relationship is defined as the point at which the victim became symptomatic. Furthermore, for each time, the function returns a uniform distribution band, as illustrated by the vertical slice in FIG. 6. Defining definitive treatment efficacy as a band allows the model to account for variability and uncertainty surrounding this parameter.

Figure 58:
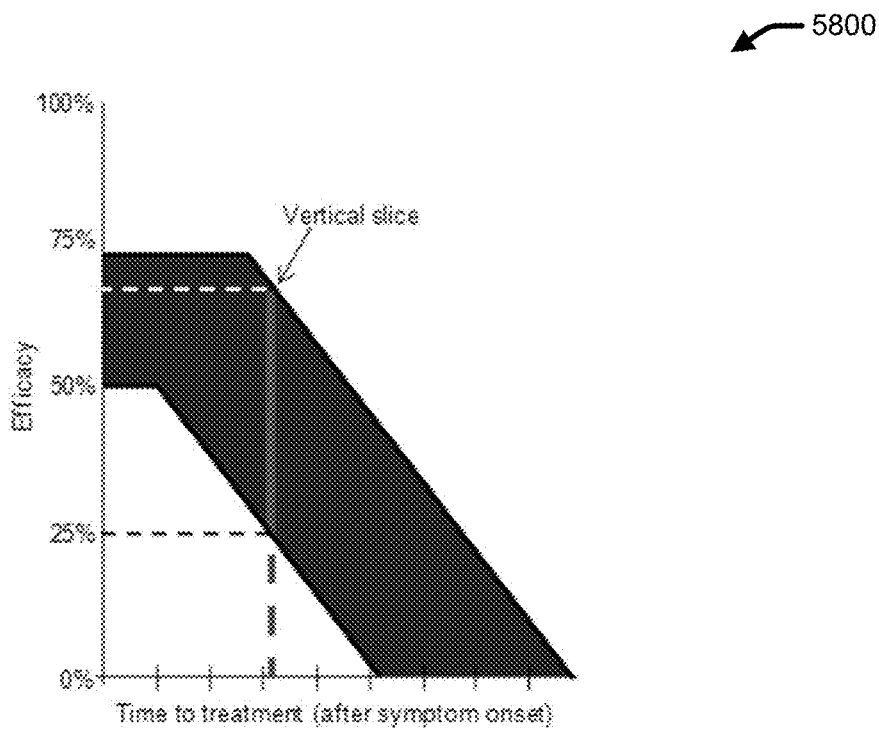
FIG. 58 illustrates a chart of a Hypothetical Example of a Treatment's Efficacy Definition according to an embodiment.

FIG. 58 illustrates a chart 5800 of a Hypothetical Example of a Treatment's Efficacy as a function of time Definition according to an embodiment.

Consider the time to treatment and the corresponding range of efficacy identified in FIG. 58 by the light blue, vertical slice in the efficacy band. The bounds on the vertical slice suggest that the receipt of treatment at that point in time yielded a success rate between 25% and 70%. The model treats the specified range as a uniform distribution and samples a single efficacy value from that range. It then performs a binary draw using the sampled efficacy to determine success or failure. Suppose in this example that the model sampled 60% from the vertical slice. The model then performs a binary draw for success or failure, with a 60% chance of choosing success. The outcome of the binary draw is applied to the entire group, groups cannot be partially saved. The model repeats this process for each group every time a potentially lifesaving treatment is applied, adjusting the definitive treatment efficacy function and time-to-treatment based on the treatment's defined efficacy and the actual treatment time.

Although a successful lifesaving does automatically save a group, failed treatments do not automatically remove a group. If a group with life-threatening injuries receives a failed treatment, the model still allows for the group to experience a temporary benefit. Specifically, a time increase is drawn from the treatment life extending efficacy distribution which provides the group with more time to receive later efficacious treatment. Regardless of success or failure, in the tiered approach to treatment, a group that receives treatment is returned to the Router in FIG. 56 to pursue another of its prescribed treatments.

When appropriate, one of two restriction factors, BRF or SEARF, can be used to prevent groups from becoming candidates for treatments. The BRF is used to prevent previously saved or benefited victims from becoming candidates for future treatment (and thus applied only to Tier 2 and Tier 3 treatments). The BRF exists to account for cases in which subsequent treatment is not needed due to previous successful treatment. As an example, if a patient was responding well to oxygen and bronchodilators, medical personnel would decide against placing them on a ventilator.

The SEARF exists to account for cases in which the treatment pathway presents potential side effects or supply concerns. For example, blood and blood product use is restricted to account for members of the population who do not allow blood transfusions due to religious beliefs. The SEARF prevents victims from becoming candidates for treatment, regardless of tier or earlier receipt of efficacious treatment.

The value of each restriction factor can range from 0 to 1, with 0 preventing all victims from becoming candidates for treatment and 1 preventing no victims from becoming candidates for treatment. Values between 0 and 1 restrict a fraction of the victims. For example, a SEARF of 0.3 restricts 70% victims from becoming candidates for a specific treatment. These values are selected to restrict the previously benefited victims from becoming candidates and represent the prevalence of drug sensitivities and pre-existing conditions.

In the case of BRF, only debris injuries have BRF values less than 100% with thermal, blunt force trauma, and lung all preventing other treatments following a successful pathway. This is likely due to the nature of debris injuries in which wound packing may be successful but other treatments such as a tourniquet are also going to be required. Victims are subjected to a unique set of restriction factors prior to becoming a candidate for any tier in their treatment regimen.

Specific treatments, such as tourniquets, can have varied efficacy based on whether or not they were properly applied. To account for this, in applicable treatment pathways, there exists a parameter for the probability that the treatment was applied correctly. This probability is modeled as a uniform distribution specific to each designated treatment. A value is drawn for each group upon entering the receiving treatment stock to determine whether or not the treatment was applied correctly. Depending on whether a successful application was drawn or not, the group will have the corresponding life extending efficacy applied—either one for incorrect application or one for the correct application.

While the Router attempts to use treatments in the preferred order, it places groups into the first treatment stock that meets the required checks. A model assumption is that when the efficacy of latter tiers is dependent on receipt of former required tiers, the former tier is considered required. Thus, if Tier 1 treatment is required, a victim will remain in the waiting for treatment stock until they receive the Tier 1 treatment. Though, for some injury types and treatment regimens in HExCAT, receiving a treatment out of order would, in reality, have some efficacy. If such a treatment is defined as a Tier 2 treatment, it could be received as the out of order only if the Tier 1 treatment is not required and still have definitive treatment efficacy or life extending treatment efficacy.

If a treatment is received out of order (e.g., Tier 2 received before Tier 1), it is still possible for the group to return to the Router and receive the former treatment (Tier 1 in this example) at a later time if the treatment did not result in the victim being saved. When this situation occurs, the benefit of having both treatments results in another opportunity for the victim to be saved or an increase in time to die via life extending efficacy.

The availability of countermeasures depends on stockpile quantities and arrival times. This countermeasure availability is the determining factor in both the treatment stock used by the Router and dictates the treatment pathway used by the Switch in FIG. 57. The delivery of local countermeasures is initiated when the need is identified. More specifically, once the time to treatment ID parameter elapses for a given group indicating the treatment required has been determined, the delivery of the required local countermeasure supplies is initiated. By default, the treatment identification results in the delivery of all countermeasures required in the victim's treatment regimen, including all tiers and alternatives.

The delivery of regional and national supplies is initiated upon sufficient consumption of the previous stockpile with "sufficient" being governed by the regional and national countermeasure release limit parameters for each countermeasure.

The quantities of treatments available in each stockpile are defined for each countermeasure as governed by the countermeasure quantity parameter. Quantities are defined as distributions and specified on a per capita basis, as a bulk supply, or both. Physical delivery times, also specific to each countermeasure and stockpile, describe and bound arrival times.

Figure 59:
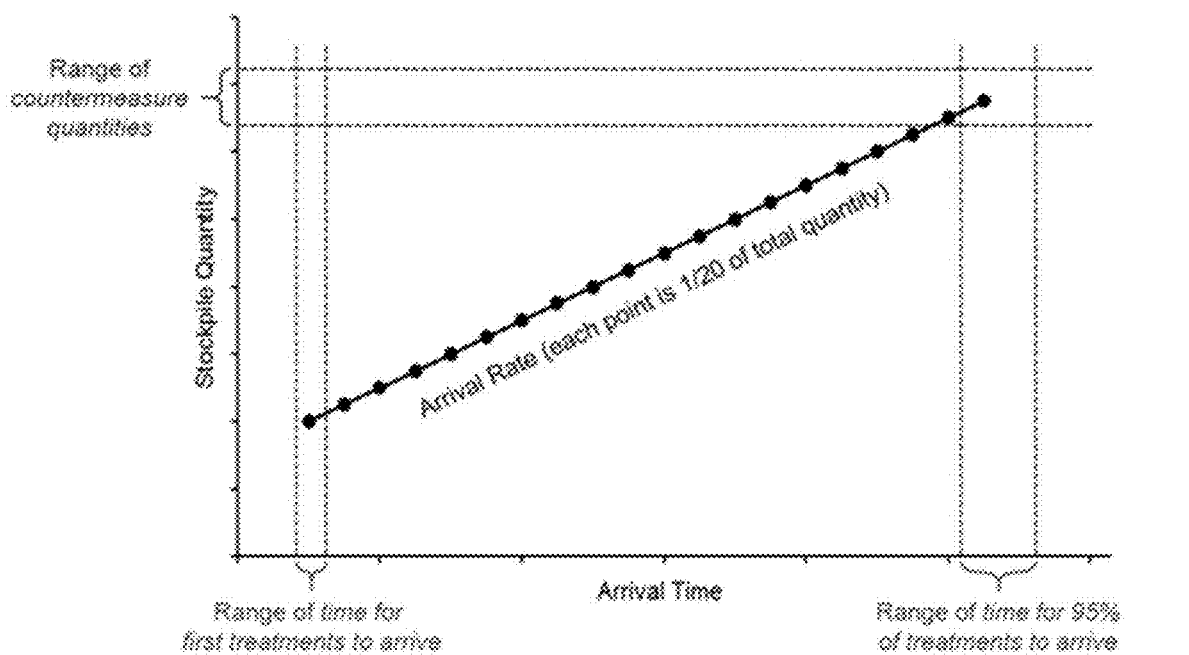
FIG. 59 illustrates a chart of Determination of Countermeasure Arrival Rate according to an embodiment.

FIG. 59 illustrates a chart 5900 of Determination of Countermeasure Arrival Rate according to an embodiment. As illustrated in FIG. 59, the model samples from separate distributions (first arrival time and the 95% arrival time) to obtain the arrival time for each delivery, shown as points along the line in FIG. 59; the latter value is correlated with the stockpile size (y-axis), which is obtained through sampling of quantity-related parameters. Using this information, the model assumes a linear relationship to yield an estimated arrival rate. Countermeasure deliveries are sampled uniformly across the allowed arrival times with each delivery having 1/20 the total countermeasure quantity. In this example, all deliveries are evenly spaced.

The square nodes labeled Dead and Alive in the figures throughout this section represent the two main end-states broken down by sub state. The six, sub end-states (and the victim types applicable to each state) include:

Dead, Untreated (life-threatening victims that are not treated, includes victims with fatal injuries);

Dead, Not Saved (life-threatening victims that are treated, but not saved, includes victims with fatal injuries);

Alive, Untreated (severe and mild/moderate that are not treated);

Alive, Saved (life-threatening victims that are saved by treatment);

Alive, Not Benefited (severe and mild/moderate that are treated but treatment was not efficacious); and Alive, Benefited (severe and mild/moderate that are treated and treatment was efficacious).

These six, sub end-states are located within the two generalized states (Dead and Alive) and accurately capture the outcome for each group.

Part of the model is parameterizing the medical response for injured individuals, based on the injuries they receive. Medical response is parameterized by dividing the response into a series of discrete events and giving each discrete event a quantifiable model parameter.

The first step in parameterizing the medical response was to define individual treatment pathways for a single injury to a victim. Treatment pathways needed to be defined for each injury type. Treatment pathways were also defined in a tiered approach. An example of an input sheet is provided in Table 46.

TABLE 46

SME Treatment Pathway Input Example

| Injury Type | AIS Score / Severity | Tier 1 Primary | Tier 1 Alt 1 | Tier 1 Alt 2 | Tier 2 Primary | Tier 2 Alt 1 | Tier 2 Alt 2 | Tier 3 Primary | Tier 3 Alt 1 | Tier 3 Alt 2 | Time to Die (No Treatment) |
|---|---|---|---|---|---|---|---|---|---|---|---|
| Debris | 6 / Fatal | Major penetrating wound to the heart. Blood loss is so severe that no treatment can save the victim | | | | | | | | | Min-Max |
| | 4-5 / Life-Threatening | First treatment option | Next option if Alt1 is unavaliable | Next option if Alt1 is unavaliable | First treatment following tier 1, if necessary | Next option if primary is unavaliable | Next option if Alt1 is unavaliable | First treatment following tier 2, if necessary | Next option if primary is unavaliable | Next option if Alt1 is unavaliable | Min-Max |
| | | Internal organ perforation | | | | | | | | | |
| | 2-3 / Severe | First treatment option | Next option if Alt1 is unavaliable | Next option if Alt1 is unavaliable | First treatment following tier 1, if necessary | Next option if primary is unavaliable | Next option if Alt1 is unavaliable | First treatment following tier 2, if necessary | Next option if primary is unavaliable | Next option if Alt1 is unavaliable | N/A |
| | | Many lacerations or minor laceration of an artery | | | | | | | | | |
| | 1 / Mild Moderate | First treatment option | Next option if Alt1 is unavaliable | Next option if Alt1 is unavaliable | First treatment following tier 1, if necessary | Next option if primary is unavaliable | Next option if Alt1 is unavaliable | First treatment following tier 2, if necessary | Next option if primary is unavaliable | Next option if Alt1 is unavaliable | N/A |
| | | Some mild lacerations | | | | | | | | | |
| | | First treatment option | Next option if Alt1 is unavaliable | Next option if Alt1 is unavaliable | First treatment following tier 1, if necessary | Next option if primary is unavaliable | Next option if Alt1 is unavaliable | First treatment following tier 2, if necessary | Next option if primary is unavaliable | Next option if Alt1 is unavaliable | |

Behavior related parameters describe the typical victim behaviors that would occur at the onset of an explosive attack. They include walking speeds and well as times that victims would likely depart to the hospital to seek medical attention.

The assisted walking speed parameter is defined as the speed at which injured victims, who cannot transport themselves, can walk to the triage site given assistance. Values are sampled for each group in the simulation.

The depart for hospital parameter is the time after the incident at which victims initiates personal travel to the hospital. This value is based on the injury type, where different injury levels can depart to the hospital at different times, however in all cases if triage is setting up or set up, victims will no longer initiate personal transport. Values are sampled for each group in the simulation.

The walking speed parameter is defined as the speed at which victims can walk to the triage site. This parameter is defined based on the severity of injury experienced by the victim; more severe victims will move slower. Values are sampled for each group in the simulation.

Once at the hospital, patients continue to receive treatments and often receive treatment that cannot be administered at a triage site. The parameters associated with victims moving to and receiving hospital care are defined below.

Once at the hospital, patients continue to receive treatments and often receive treatment that cannot be administered at a triage site. The parameters associated with victims moving to and receiving hospital care are defined below.

The assessment bandwidth parameter is defined as the number of victims that can be assessed at the hospital at a time, bandwidth is consumed by every victim currently undergoing an assessment. Once the victim's symptoms have been identified, they can be assigned to a treatment pathway and no longer consume assessment bandwidth. Values for bandwidth depend on available personnel.

The bed turnover time parameter is defined as the time it takes for each bed to become unoccupied after a victim's treatment is completed. This parameter is intended to model extra time between treating victims, such as cleanup of the room, or restocking room supplies. Values vary based on treatment efficacies, bed type, and available personnel.

The occupancy rate parameter is defined as the ratio of staff and hospital beds that are occupied to the total number at the hospital. A unique value for each bed type and personnel skill level is defined between 0 and 1. Hospital treatments can only be administered to victims who have been assigned a bed and have the required medical personnel to administer the treatment, therefore if all of the beds are full or if all the staff are occupied, additional victims cannot be treated until the ones occupying hospital beds have been treated or staff become available. This factor is intended to model a baseline occupancy before the exposure event occurs.

The occupied surge factor is the percentage of occupied personnel or beds that are made available as a direct reaction to the exposure event. For example, if there are 100 skilled personnel and 20% (20) of them are occupied, the addition of an occupied surge factor of 50% would result in 10 skilled personal becoming available. A unique surge factor can be applied to each personnel skill level and bed type. This parameter models hospitals' reaction to news of a mass casualty event.

The personnel per bed parameter is defined as the number of personnel a hospital has available per hospital bed. Values for each personnel skill type can be set independently.

The personnel per ICU bed parameter is defined as the number of personnel capable of providing ICU care. This parameter differs from the personnel per bed in that only personnel who are capable of administering ICU care are considered, as this is a specialized type of care. Values for each personnel skill type can be set independently.

There are two surge factor parameters that the model takes into account: bed surge factor and personnel surge factor. The bed surge factor accounts for the percent increase in general beds, ICU beds, and operating theaters given a mass casualty event, for example makeshift basic beds in the hallway of the emergency ward. Each of the three types of beds have unique surge factor parameters. The personnel surge factor parameter is defined as a factor that accounts for an increase in staff upon the realization of a mass casualty event. The parameter is set as a percent increase that is applied to the hospital specific staff numbers in the simulation. A unique surge factor can be applied to each personnel skill level.

The surge time parameter is the time it takes for the personnel surge to complete. There are two aspects to this parameter—the first is initial personnel surge time (i.e., the arrival time of the first extra emergency personnel) and the second is the 95% surge time (i.e., when 95% of surge personnel have arrived). A uniform distribution is created between the two times, and each wave of surge personnel draws a unique arrival time from the distribution excepting the initial wave.

Another essential piece of the treatment pathways as described above is the parameterization of the resources necessary to administer the treatments. Treatments can only be administered if the necessary equipment and staff are available to administer them. Therefore, part of the model includes defining how many resources are available for treatments. There are three types of resources, as follows: Countermeasure Stockpiles, Medical Personnel, and Medical Facilities.

Countermeasures are consumable items used in treatment and stockpiles are the amounts of available at each site. Each treatment uses a certain amount of a countermeasure (e.g., one syringe, 500 mL of blood, etc.). Once the treatment is administered to a patient, the countermeasure is no longer available in the model and the amount in the stockpile is decreased. These parameters were determined from publicly available data or extrapolated from such sources. Local and national response programs also provided some information.

Countermeasure availability was defined for on-site, ambulance, and hospital settings. For on-site settings, countermeasure availability was quantified in bulk (i.e., the total amount on-site) or in relative terms (i.e., per person). For ambulances, supply was described simply as per ambulance. For hospital settings, countermeasure availability could additionally be described per hospital bed.

Stockpiles are also defined on the local, regional, and national level. The local level comprises of sources immediately surrounding the area of the incident, largely local hospitals. The regional level is defined as sources in the surrounding geopolitical area, such as state level stockpiles or additional hospitals not considered local. The national level is defined as any resources that are deployed countrywide, such as a national stockpile or a national response team. Relative stockpiles (e.g., per person) are defined only at the local level, while bulk stockpiles are defined for the local, regional, and national levels.

The time required for 95% of treatments to arrive onsite parameter is defined as the time required for 95% of the countermeasures from a specific stockpile to arrive at the treatment location. This time delay begins once the need for the countermeasures is recognized by the model and ends when 95% (i.e., nearly all) of the treatments are available for the medical personnel to administer. The time for physical delivery and distribution at the site/hospital is included in this value, but delays associated with the arrival of medical personnel or factors which delay initial assessment of injuries are not. This parameter was uniquely defined for stockpiles local, regional, and national stockpiles originating from, for example, hospitals, regional response programs, as well as bulk supplies. The 95% arrival time parameter is sampled once per simulation for each countermeasure/stockpile source combination.

The onsite first arrival time parameter defines the time required for the first countermeasures from a specific stockpile of countermeasures to arrive at the treatment location. This time delay begins once the need for the countermeasure is recognized by the model and ends when the first treatment is available for medical personnel to administer. The time for physical delivery and distribution at the treatment location is included in this value. Delays associated with the arrival of medical personnel or determining which countermeasure is needed are not included in this estimate. This parameter was uniquely defined for stockpiles local, regional, and national stockpiles originating from, for example, hospitals, regional response programs, as well as bulk supplies. The first arrival time parameter is sampled once per simulation for each countermeasure/stockpile source combination.

Medical facilities are the locations necessary for patient treatment but unlike countermeasure stockpiles, they can be reused. Medical facilities are used for a certain period of time, depending on their purpose, and then become available to the model again for another patients once that time is up. Medical facilities include basic medical beds, which are beds available for less complex treatments, and ICU beds, which are beds in intensive care medical or surgical. These beds are typically used by patients from when they finish assessment at the hospital to when they are discharged from that unit.

Medical facilities also include operating theaters, which are operating suites used for surgical procedures. Because operating theaters may only be used for surgical procedures, unlike beds, operating theaters are used as long as the patient is undergoing the surgical procedure, and then become available for another patient.

Medical personnel are people who administer the treatments as defined in the treatment pathways. Unlike countermeasure stockpiles, personnel in the model can be used more than once. A medical person is unavailable for as long as it takes to administer the treatment, and then becomes available in the model again to administer another treatment. Medical personnel are defined for by either on-site or hospital settings, and for both settings personnel were considered to be either basic skilled, skilled, or highly skilled.

In on-site scenarios, a basic-skilled person is a bystander or other person with no medical training, a skilled person is an emergency medical technician (EMT) or equivalent, and a highly skilled person is someone from a surgical field team or other form of specialized medical response. In hospital settings, basic-skilled personnel are non-clinical hospital personnel, skilled personnel are emergency or surgical nurses and non-trauma providers, and highly skilled personnel are emergency and surgical department clinical staff.

Symptom related parameters describe the actual symptoms that victims would face as a result of an explosive event and their injuries. These include the symptom onset time and the time to die (if the injury was lethal). Although many symptom specific treatment parameters are defined, such as the identification of the treatment necessary as well as the sequence of treatments used, these are considered treatment parameters.

The symptom onset time parameter is defined as the duration between the explosive event and the point in time that the victims both display severe enough symptoms that medical attention is warranted and decide to seek care (or someone decides to seek care for them). Delays associated with receiving the dose or being collocated with medical personnel are not included in this parameter. The symptom onset time values depend on victim type and are sampled for each group in the simulation. While symptoms related from many injuries related to explosions are near instantaneous, there are some injuries where symptoms are delayed.

The time to die parameter is defined as the duration between symptom onset and death for victim and only exists for victims with life-threatening or fatal injuries. This parameter is sampled at the initial onset of symptoms. As victims go through the model and receive treatments, the time to die parameter value can be extended.

After patients are assessed at triage, most will need transport to a hospital for further assessment or treatment. Patients who do not have severe injuries are capable of personal transport to a hospital, either alone or through "buddy transport", and may do so before, during, or after triage care. Patients with more severe injuries need to be transported to the hospital by EMS. Parameters related to the transportation account for the number of vehicles (both personal and emergency) available as well as the relevant parameters associated with each. Vehicle specific parameters include the speed, how many victims can be transported per vehicle, and how many, if any, medical personnel are riding in each vehicle. Transportation also accounts for some parameters which are not vehicle specific, such as the arrival times of personnel and travel times to get to the triage site.

The dispatch initial delay is the time between the start of the simulation and the departure time of the initial ambulance wave from their station.

The dispatch travel time is the amount of time that it takes for the emergency response vehicles to travel from their station to the triage site.

The time when 95% of available vehicles arrive at the scene. Using this parameter and the initial arrival time, calculated from the sum of the initial dispatch delay and the dispatch travel time, a distribution of arrival times for any vehicle is created. This distribution is sampled once for each vehicle excepting the initial arrival.

The on-site personnel arrival parameter is the time when on-site personnel start to set up triage. If there is a value for triage initial personnel, then an on-site personnel arrival time of 0 s will result in the immediate setup of triage. However, if no personnel are on-site then this value corresponds with the initial ambulance arrival time and must be greater than or equal to that value.

The vehicle library consists of various emergency and personal vehicles and is modular in the fact that new vehicles can be added easily. Currently the vehicles in the library consist of ambulances, personal vehicles, and helicopters. Each vehicle has sub parameters that specify: the number of vehicles available, the vehicle speed, the victims per vehicle, restock time, and personnel. Each parameter is described below in more detail.

The personnel per vehicle parameter is defined as the number of personnel an emergency vehicle has available. Values are determined based on the skill level of personnel. The vehicles available parameter defines the number of vehicles available for each vehicle type. The victims per vehicle parameter defines the number of victims that can be held in each vehicle type. The vehicle speed parameter defines the average speed at which vehicles travels to the hospital. The vehicle restock time parameter defines the amount of time it takes to stock each of the medical emergency with medical supplies.

Treatment related parameters are related to the treatments administered to victims rather than the symptoms experienced. Parameters include time for treatment to be identified, time for treatment to be administered, time for treatment to improve symptoms, treatment efficacy, and treatment hierarchy. Treatment parameters will account for one or more of these factors, depending on the parameter. Of note, treatment parameters are not considered to include the treatment definitions themselves, which are a combination of the countermeasures used, the personnel required, and in some cases, the facility required to administer the treatment.

The bulk supply parameter refers to the total amount of a treatment available. There is a bulk supply available for on-site as well as per ambulance. Each of these parameters also has unique location-based value for the local, regional, and national level.

The relative supply parameter refers to the amount of a treatment available per 1000 people. There are multiple, unique instances of the relative parameter such as relative supply per bed, relative supply on-site, and relative supply for response programs. Each of these individual parameters also has unique location-based values for the local, regional, and national level.

Treatment pathways were defined in a tiered approach. The tiered approach allows for multiple rounds of treatment, to account for the complexities of treating injuries. Tiered treatments should be considered as steps in a treatment process, where Tier 1 is administered to a patient followed by Tier 2 depending on the efficacy of Tier 1. For example, a patient with a severe debris injury may be treated on-site by applying pressure to the wound, followed by the administration of a tourniquet. If the Tier 1 treatment is not available, the Tier 2 treatment may still be administered provided the previous tier was not required.

Each treatment tier may also identify some alternative treatments. Unlike tiers, an alternative treatment is a way of treating a patient only if the first suggested treatment is unavailable. For example, if a patient reaches Tier 2 treatment and a tourniquet is not available, a skilled makeshift tourniquet may be administered instead. However, if the tourniquet is available, then a skilled makeshift tourniquet is not needed, no matter the efficacy of the original Tier 2 treatment.

Once single injury pathways were defined, the focus was shifted to how a patient would be treated if they received injuries across multiple injury types. The goal with defining treatment for multiple injuries was to utilize as much of the work already completed for single estimates as possible. However, in some cases a combination of multiple injury types resulted in modifications to how treatments need to be administered.

To address the issue of multiple injuries, the amount of possible injury combinations had to be calculated and categorized into an effect severity. To be considered a case of multiple injuries, the patient would have to receive injuries across at least two injury types. To avoid overcomplicating the model, it was assumed that no patient would receive more than three injury types. In total, there are 820 possible injury combinations. A combination of each injury's AIS score determines the final severity, these combinations are broken down by final severity in Table 47.

TABLE 47

Possible Injury Severity Combinations

| Final Severity | Number of Combinations |
|---|---|
| Mild/Moderate | 25 |
| Severe | 80 |

TABLE 47-continued

Possible Injury Severity Combinations

| Final Severity | Number of Combinations |
|---|---|
| Life-Threatening | 275 |
| Fatal | 440 |
| Total | 820 |

When combining injury types, the model then has to choose between multiple treatment pathways. Based on the severity of the combined injury, some modifications to the treatment pathways may be necessary. These modifications and the expected treatment outcomes are outlined in Table 48.

TABLE 48

Modifications to Treatment Pathways as a Result of a Victim Sustaining Multiple Injuries

| Injury Type 1 | Injury Type 2 | Modifications to Treatment Pathway | Treatment Outcome |
|---|---|---|---|
| Mild/Moderate | Mild/Moderate | None | Patient is considered benefitted after efficacious treatment for at least one injury |
| Severe | Mild/Moderate | None | Patient is considered benefitted after efficacious treatment for the severe injury |
| Severe | Severe | In some cases, multiple severe injuries should be upgraded to life-threatening | Patient is considered benefitted after efficacious treatment for at least one severe injury (even if they are both upgraded to life-threatening) |
| Life-Threatening | Mild/Moderate | Treated like a single life-threatening injury, although the victim can receive treatments for both injury types | Patient is only saved after efficacious treatment for the life-threatening injury |
| Life-Threatening | Severe | Comorbidity factor introduces a 10% reduction in efficacy and life-extension factor per additional severe injury | Patient is only saved after efficacious treatment for at least one of the injuries |
| Life-Threatening | Life-Threatening | Comorbidity factor introduces a 25% reduction in efficacy and life-extension factor per additional life-threatening injury | Patient is only saved after efficacious treatment for both life-threatening injuries |
| Fatal | Mild/Moderate | Treated like a single fatal injury | Patient dies when the fatal injury's "time to die" is reached |
| Fatal | Severe | Comorbidity factor introduces a 10% reduction in the life-extension factor per additional severe injury | Patient dies when the fatal injury's "time to die" is reached |
| Fatal | Life-Threatening | Comorbidity factor introduces a 25% reduction in the life-extension factor per additional life-threatening injury | Patient dies whenever the shortest "time to die" is reached |
| Fatal | Fatal | Comorbidity factor introduces a 50% reduction in the life-extension factor per additional fatal injury | Patient dies whenever the shortest "time to die" is reached |

The definitive treatment efficacy parameter is defined as the probability of success of a treatment. It is defined as a band (i.e., a range) as a function of time, with time zero corresponding to the time of symptom onset. When applied to victims with life-threatening injuries, definitive efficacy refers to the probability that the countermeasure saves the life of the victim. When applied to victims with severe or mild/moderate injuries, definitive efficacy refers to the probability that the countermeasure benefits the victim. Note that a victim is considered benefited if the victim experiences improvement in symptoms or outcomes such as an improved quality of life, quicker recovery, or reduced suffering. A benefit does not imply a reduction in the severity of the injury category.

This parameter value depends on the treatment's countermeasure applied to the victim as well as the victim type. Victims with fatal injuries do not have a definitive treatment efficacy parameter, as they cannot be saved and therefore there is no definitive treatment efficacy.

This parameter is sampled for each group in the simulation based on the group's time of treatment. When assigning an exact efficacy value for the group's treatment, the range of efficacy values at the time of treatment is treated as a uniform distribution.

The life extending treatment efficacy parameter is defined as a uniform distribution from which a value is drawn for each group to specify the increase in the time to die value in minutes. The increase in time to die may result of a victim with life-threatening injuries receiving a field treatment or a victim with fatal injuries receiving any treatment (as they cannot be saved). The logic behind this parameter is that while a treatment may not save the victim's life, it can benefit the victim in extending the amount of time the patient has left to live. Therefore, this parameter only applies to victims who are in danger of dying (i.e., victims with fatal or life-threatening injuries) and is not defined for patients with severe or mild/moderate injuries. The parameter value depends on the victim type, countermeasure, and treatment tier, and is sampled for each group in the simulation each time they receive a treatment.

The treatment sequence parameter is defined as the sequence of treatments applied to the victim. The values for this parameter vary based on location, injury type, and injury severity. Further, the values for this parameter follow a treatment hierarchy. The treatment sequence might be further modified if the victim experiences multiple injuries. While the treatment sequence is considered a symptom related parameter, as the treatments are directly based on the symptoms experienced by the victim, additional parameters are then defined based on the treatment sequence.

The time to treatment, or administration time parameter is defined as the time required to administer a specific countermeasure to a single victim. This delay begins after the required treatment was identified and the victim, treatment, and medical personnel are collocated. This parameter is defined for each countermeasure and is sampled for each group in the simulation.

The time to treatment ID (identification) parameter is defined as the time required for medical personnel to determine a victim's necessary treatment sequence. This time delay begins once symptomatic victims and medical personnel are physically together and ends when the appropriate treatment pathways are identified. Delays associated with the victims becoming symptomatic, victims being collocated with medical personnel, or the delivery and receipt of the needed treatment are not considered in this parameter. The parameter value is dependent on victim injury type and severity and is sampled for each group in the simulation.

As first responders arrive on-site, they need to set up a triage site so they can administer care to victims at the location of the event. After triage is set up, victims who are capable can "self-transport" to the triage site and begin to receive care. First responders also transport victims who cannot move themselves to the triage location. After receiving treatment at a triage site, victims then progress to hospital treatment or exit medical care. The parameters associated with victims moving to and receiving treatment at triage sites are defined below. There can be an initial number of medical personnel on-site at t=0 s as well. If this is the case, then the triage setup will begin immediately.

The assessment bandwidth parameter is defined as the number of victims that can be assessed at triage site at a time, bandwidth is consumed by every victim currently undergoing an assessment. Once the victim's symptoms have been identified, they can be assigned to a treatment pathway and no longer consume assessment bandwidth. Values for bandwidth depend on available personnel.

The setup time parameter is defined as the time required for triage to be set up. More specifically, it is the time from which there are first responders on-site until the triage is ready to treat patients (and therefore "set up"). This time period does not include delays for treatment identification. The setup time parameter does not have any dependencies and is sampled once for each realization in the simulation.

The setup distance parameter is defined as the distance between the event and where triage is set up. Triage cannot be set up at the site of the event due to safety reasons, and first responders have a responsibility to set up the triage site in a safe location. Values depend on event location and can be modeled as a distribution for simulation cases that consist of multiple runs or realizations.

The triage efficacy parameter is defined as the probability that victim groups are able to be prioritized in a manner that optimizes treatment success. Efficacious triaging is considered perfect prioritization by injury severity, while inefficacious triaging will prioritize treatment in order of arrival regardless of injury. There are four categories within this parameter to account for both locations, on-site and in hospital, as well as both pre-admission and post-admission. The values range from 0.0 to 1.0, with values of 1.0 indicating 100% efficacious triage. As an example, a value of 0.5 corresponds with priority based on injury severity half of the time and victim arrival time the other half the time.

The initial medical personnel on-site at the time of the attack. This parameter contains distributions of basic skilled, skilled, and highly skilled medical personnel on-site.

The model outputs a number of parameters describing victim end states, how they came to be, and how treatments countermeasures were consumed in the process. Table 49 provides a list and descriptions of the outputs produced by the Medical Mitigation Model. All of the outputs fall into one of two categories: victim summaries and countermeasure tracking.

TABLE 49

Model Outputs

| Parameter | Description |
| --- | --- |
| Amount of Countermeasure consumed during model execution at triage | The number of countermeasure treatments that were consumed during the medical mitigation process at triage |
| Amount of Countermeasure consumed during model execution at the hospital | The number of countermeasure treatments that were consumed at the hospital during the medical mitigation process |
| Amount of Countermeasure released during model execution at triage | The total number of countermeasure treatments that were ever available at triage during the medical mitigation process. This number includes consumed countermeasures |
| Amount of Countermeasure released during model execution at the hospital | The total number of countermeasure treatments that were ever released at the hospital during the medical mitigation process This number includes consumed countermeasures |
| Hospital Admissions | The number of patient admissions at each hospital |
| Lives Saved | The number of people with life-threatening injuries that did not die due to medical mitigation |
| Number of individuals who died and did not receive treatment | The number of people with life-threatening or fatal injuries that died before treatment could be administered |
| Number of individuals who died and received treatment | The number of people with life-threatening or fatal injuries that died after treatment was administered |
| Number of individuals who received efficacious treatment | The number of people with life-threatening or fatal injuries that received treatment that was effective |
| Number of non-life-threatening individuals who benefitted from treatment | The number of people with non-life-threatening injuries that received treatment that was effective |
| Number of non-life-threatening individuals who did not benefit from treatment | The number of people with non-life-threatening injuries that received treatment that was not effective |
| Treatments Consumed at the hospital | The number of countermeasure treatments that were used at the hospital during medical mitigation |
| Treatments Consumed at triage | The number of countermeasure treatments that were used during medical mitigation |
| Victims Benefited | The number of people with non-life-threatening injuries who were given medical mitigation that resulted in a reduction in injuries |

Figure 60:
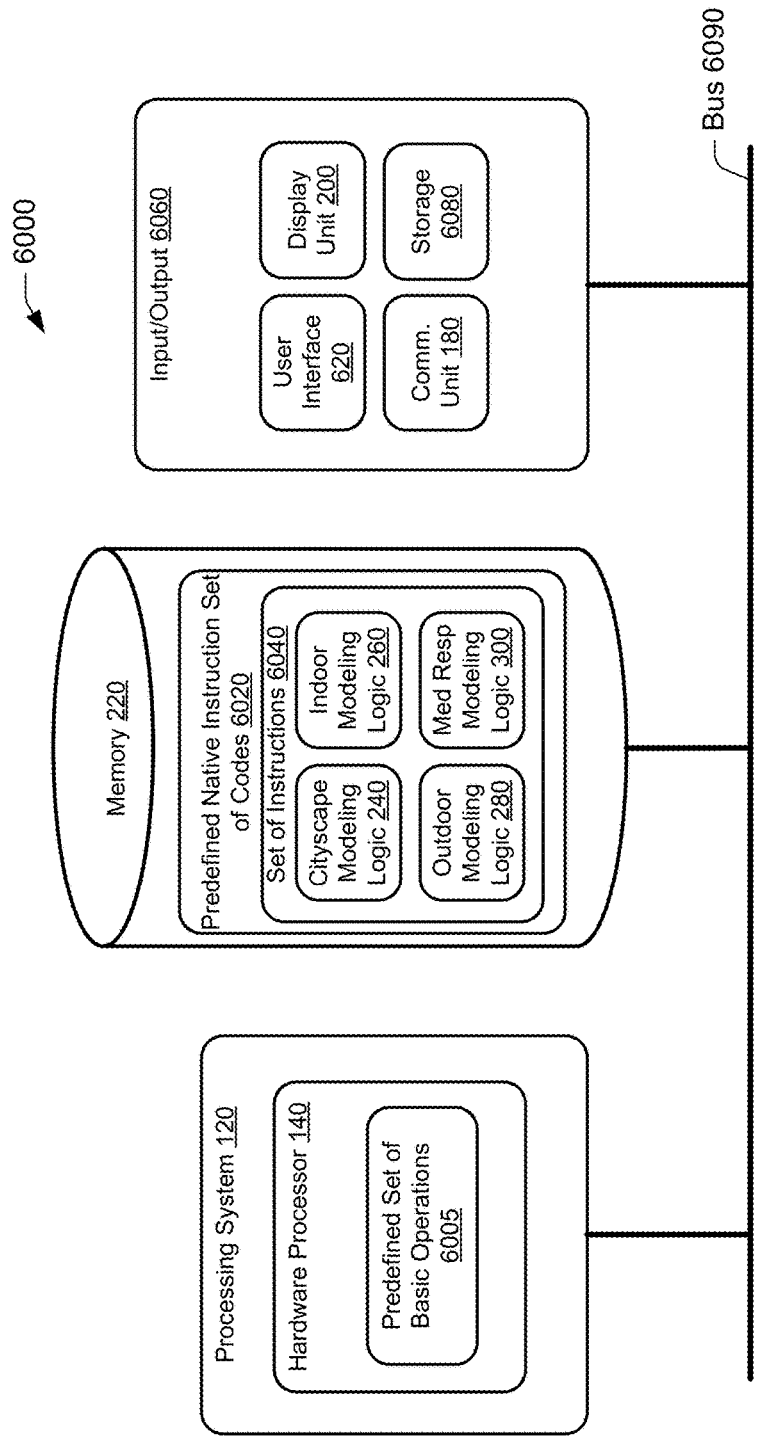
FIG. 60 illustrates a diagram of a computer system according to an embodiment.

FIG. 60 illustrates a diagram of a computer system 6000 according to an embodiment. The computer system 6000 includes a processing system 120, memory 220, and input/output module 6060 communicatively coupled via bus 6090. The processing system 120 includes hardware processor 140. The hardware processor 140 includes predefined set of basic operations 6005. The memory 220 includes predefined native instruction set of codes 6020. The predefined native instruction set of codes 6020 includes a set of instructions 6040. The set of instructions 6040 includes cityscape modeling logic 240, indoor modeling logic 260, outdoor modeling logic 280, and medical response modeling logic 300. The input/output 6060 includes user interface 620, display unit 200, communication unit 180, and storage 6080. In an embodiment, such components may serve as the computer system including the logic that carries out the methods described herein.

Certain attributes, functions, steps of methods, or sub-steps of methods described herein may be associated with physical structures or components, such as a module of a physical device that, in implementations in accordance with this disclosure, make use of instructions (e.g., computer executable instructions) that are embodied in hardware, such as an application specific integrated circuit, computer-readable instructions that cause a computer (e.g., a general-purpose computer) executing the instructions to have defined characteristics, a combination of hardware and software such as processor implementing firmware, software, and so forth so as to function as a special purpose computer with the ascribed characteristics. For example, in embodiments a module may comprise a functional hardware unit (such as a self-contained hardware or software or a combination thereof) designed to interface the other components of a system such as through use of an API. In embodiments, a module is structured to perform a function or set of functions, such as in accordance with a described algorithm. This disclosure may use nomenclature that associates a component or module with a function, purpose, step, or sub-step to identify the corresponding structure which, in instances, includes hardware and/or software that function for a specific purpose. For any computer-implemented embodiment, "means plus function" elements will use the term "means;" the terms "logic" and "module" and the like have the meaning ascribed to them above, if any, and are not to be construed as means.

The claims define the invention and form part of the specification. Limitations from the written description are not to be read into the claims.

An interpretation under 35 U.S.C. § 112(f) is desired only where this description and/or the claims use specific terminology historically recognized to invoke the benefit of interpretation, such as "means," and the structure corresponding to a recited function, to include the equivalents thereof, as permitted to the fullest extent of the law and this written description, may include the disclosure, the accompanying claims, and the drawings, as they would be understood by one of skill in the art.

To the extent the subject matter has been described in language specific to structural features and/or methodological steps, it is to be understood that the subject matter defined in the appended claims is not necessarily limited to the specific features or steps described. Rather, the specific features and steps are disclosed as example forms of implementing the claimed subject matter. To the extent headings are used, they are provided for the convenience of the reader and are not be taken as limiting or restricting the systems, techniques, approaches, methods, devices to those appearing in any section. Rather, the teachings and disclosures herein can be combined, rearranged, with other portions of this disclosure and the knowledge of one of ordinary skill in the art. It is the intention of this disclosure to encompass and include such variation. To the extent any elements or steps are described as "optional," it does not indicate that all or any other elements or steps are mandatory.

What is claimed is:

1. A computerized method to model consequences of an explosion, comprising:
   (a) receiving, by a computing system, user input including parameters for generating and modeling a scenario, explosion device model, and propagation of hazards and injuries;
   (b) generating, by the computing system, the scenario based on the user input and an iterative subset of scenario parameters, the user input indicating an indoor explosion target or an outdoor explosion target, the generating the scenario further comprising communicating, by the computing system, with geospatial databases, retrieving geospatial data from the geospatial databases, and modeling the geospatial data based on a three-dimensional grid of cells, the computing system discretizing space representing the scenario into the three-dimensional grid of cells;
   (c) generating, by the computing system, an explosive device model based on the user input and an iterative subset of explosive device parameters;
   (d) modeling, by the computing system, propagation of hazards into the scenario based on the user input and an iterative subset of hazard parameters, the computing system applying the hazard parameters to the three-dimensional grid of cells, the hazards corresponding to detonation of the explosive device model;
   (e) modeling, by the computing system, injuries corresponding to the modeling propagation of hazards into the scenario, based on an iterative subset of injury parameters, the modeling injuries comprising applying population density to the three-dimensional grid of cells;
   scenario parameters, the explosive device parameters, the hazard parameters, and the injury parameters being distributions applied to Monte-Carlo probabilistic simulations to generate and model the scenario, the explosion device model, and the propagation of hazards and injuries;
   (f) iterating, by the computing system, based on the iterative subsets of scenario parameters, the explosive device parameters, the hazard parameters, and the injury parameters until the discretized space representing the scenario is covered, thereby generating the scenario, generating the explosive device model, modeling propagation of hazards, and modeling injuries; and
   (g) generating, by the computing system, an injury record based on the modeling of injuries corresponding to the iterating.

2. The method of claim 1, further comprising:
   modeling a medical mitigation response based on the modeling injuries and an iterative subset of medical mitigation parameters, wherein a computing system models the medical mitigation with a stock-and-flow simulation comprising assigning attributes to different groups of victims.

3. The method of claim 1, wherein iterating comprises selecting additional iterative subsets according to at least one of probabilistic risk assessment (PRA), game theory, multi-attribute utility, and Monte Carlo methods.

4. The method of claim 1, further comprising probabilistically generating the scenario parameters for an indoor consequence model based on Hazus data to determine material information and population information for targets.

5. The method of claim 1, wherein the scenario comprises parameters representing buildings wherein the buildings are represented with a three-dimensional grid of cells.

6. The method of claim 5, wherein modeling propagation of hazards into the scenario further comprises modeling shockwave, debris, combustion gases, and building collapse based on the three-dimensional grid of cells thereby simulating a continuous phenomena of detonation of the explosive device model.

7. The method of claim 5, wherein modeling injuries further comprises calculating injuries of individuals in a population density, in the three-dimensional grid of cells based on performing calculations on a block-by-block basis.

8. The method of claim 5, wherein generating parameters representing buildings is further based on a plurality of parameters representing barriers, wherein a given barrier is locatable between adjacent grid cells and comprises parameters representing building materials with corresponding structural properties.

9. The method of claim 8, wherein the given barrier is a structural support barrier comprising a number of grids positioned above the structural support barrier, and to which building collapse is applied when the structural support barrier fails due to propagation of hazards into the scenario.

10. The method of claim 1, further comprising querying for user input corresponding to a location of the explosive device model, including a target city, a target latitude and target longitude, and a radius around the target latitude and target longitude within which the explosive device model can be located.

11. The method of claim 1, further comprising accessing a first database to identify building types for an area of the scenario, accessing a second database for population density for the area of the scenario, and distributing the population density across the area of the scenario according to the building types.

12. The method of claim 1, wherein generating the scenario further comprises performing cityscape generation to characterize type and occupancy of buildings surrounding a location of the explosive device model.

13. The method of claim 12, wherein the cityscape generation is based on a plurality of datasets including an HSIP population dataset, a GRiD database, and HAZUS census block level information.

14. The method of claim 12, wherein the cityscape generation generates a realization of potential building types and construction by probabilistically assigning types of buildings at a census block level and estimating building construction, based on probabilistic shapefiles that describe approximate locations and approximate dimensions of buildings to generate a realization of potential buildings and different building heights corresponding to a total square footage.

15. The method of claim 14, wherein the cityscape generation generates buildings probabilistically by dividing a census block into parcels based on ratios of surface area for building types, and by then placing buildings in a center of a corresponding given parcel, with a number of floors for a given building being sampled from a correlation distribution generated from fully defined areas.

16. The method of claim 1, wherein generating the explosive device model is based on the user input designating an explosive device material, and parameters representing a fuel for those explosive device materials using fuels for detonation.

17. The method of claim 16, wherein generating the explosive device model is based on the user input designating at least one of fragmentation enhancements, casing enhancements, or thermal enhancements to the explosive device model.

18. The method of claim 1, wherein modeling propagation of hazards into the scenario comprises:
   determining that the user input indicates an indoor explosion target; and
   propagating parameters corresponding to interior shockwaves, interior combustion gases, and interior debris into the scenario based on the discretized space of the three-dimensional grid of cells representing the scenario.

19. The method of claim 1, wherein modeling propagation of hazards into the scenario comprises:
   determining that the user input indicates an outdoor explosion target; and
   propagating into the scenario parameters corresponding to exterior shockwaves accounting for distance from blast location and exterior debris, based on isopleths.

20. The method of claim 1, wherein modeling injuries comprises:
   calculating, for a plurality of population groups, a plurality of respective levels of injury corresponding to pressure, impulse, temperature, and fragmentation; and
   calculating, for the plurality of population groups, a plurality of respective building injuries from an amount of building collapse.

21. The method of claim 20, wherein a given population group corresponds to a grid cell for indoor spaces and an isopleth for outdoor spaces.

22. The method of claim 2, wherein modeling the medical mitigation response comprises assigning victims into groups according to injury exposure as expressed by parameters assigned to a given group.

23. The method of claim 22, further comprising modeling the medical mitigation response using stock-and-flow modeling by moving the given group through a plurality of stocks according to parameters assigned to the given group.

24. The method of claim 5, wherein a resolution of the three-dimensional grid of cells is specified by a user.

25. The method of claim 5, wherein a user inputs a width, a depth, and a height of the cells in the grid of cells.

* * * * *